(12) United States Patent
Wu et al.

(10) Patent No.: US 9,718,823 B2
(45) Date of Patent: Aug. 1, 2017

(54) 2, 6-DI-NITROGEN-CONTAINING SUBSTITUTED PURINE DERIVATIVE, AND PREPARATION METHOD, PHARMACEUTICAL COMPOSITION AND USE THEREOF

(71) Applicant: Zhejiang Medicine Co., Ltd. Xinchang Pharmaceutical Factory, Xinchang County (CN)

(72) Inventors: Guofeng Wu, Xinchang County (CN); Yongmei Xu, Xinchang County (TW); Wei Mao, Xinchang County (CN); Chunlin Chen, Xinchang County (CN); Zhanggui Wu, Xinchang County (CN); Xiaoqin Lin, Xinchang County (CN); Jun Wang, Xinchang County (CN); Jinna Cai, Xinchang County (CN); Sen Xiao, Xinchang County (CN); Lili Lv, Xinchang County (CN)

(73) Assignee: ZHEJIANG MEDICINE CO., LTD. XINCHANG PHARMACEUTICAL FACTORY, Xinchang County (CN)

(*) Notice: Subject to any disclaimer, the term of this patent is extended or adjusted under 35 U.S.C. 154(b) by 0 days.

(21) Appl. No.: 14/914,674

(22) PCT Filed: Aug. 27, 2014

(86) PCT No.: PCT/CN2014/000799
§ 371 (c)(1),
(2) Date: Feb. 26, 2016

(87) PCT Pub. No.: WO2015/027667
PCT Pub. Date: Mar. 5, 2015

(65) Prior Publication Data
US 2016/0207924 A1    Jul. 21, 2016

(30) Foreign Application Priority Data

Aug. 30, 2013 (CN) .......................... 2013 1 0388308
Aug. 22, 2014 (CN) .......................... 2014 1 0417725

(51) Int. Cl.
| | | |
|---|---|---|
| A01N 43/90 | (2006.01) |
| A61K 31/52 | (2006.01) |
| C07D 473/00 | (2006.01) |
| C07D 473/18 | (2006.01) |
| A61K 31/5377 | (2006.01) |
| C07D 473/16 | (2006.01) |

(52) U.S. Cl.
CPC ............ *C07D 473/18* (2013.01); *A61K 31/52* (2013.01); *A61K 31/5377* (2013.01); *C07D 473/16* (2013.01)

(58) Field of Classification Search
None
See application file for complete search history.

*Primary Examiner* — Jeffrey H Murray
(74) *Attorney, Agent, or Firm* — Ash Tankha; Lipton, Weinberger & Husick

(57) ABSTRACT

The present invention provides a 2, 6-di-nitrogen-containing substituted purine derivative having a formula (I) structure, or pharmaceutical salt or hydrate thereof, and preparation method and use thereof. The compound is broad spectrum anticancer, low toxicity, high anticancer activity and good stability.

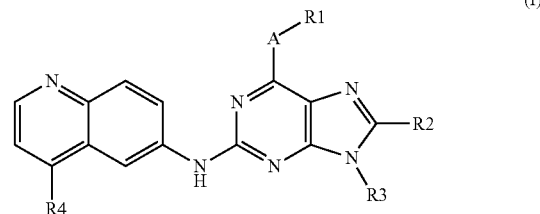

12 Claims, No Drawings

2, 6-DI-NITROGEN-CONTAINING SUBSTITUTED PURINE DERIVATIVE, AND PREPARATION METHOD, PHARMACEUTICAL COMPOSITION AND USE THEREOF

CROSS-REFERENCE TO RELATED APPLICATIONS

This application is a national phase application of the PCT international application number PCT/CN2014/000799 titled "2, 6-DI-NITROGEN-CONTAINING SUBSTITUTED PURINE DERIVATIVE, AND PREPARATION METHOD, PHARMACEUTICAL COMPOSITION AND USE THEREOF", filed in the State Intellectual Property Office of the People's Republic of China on Aug. 27, 2014, which claims priority to and the benefit of Chinese patent application number 201310388308.3, filed in the State Intellectual Property Office of the People's Republic of China on Aug. 30, 2013, and Chinese patent application number 201410417725.0, filed in the State Intellectual Property Office of the People's Republic of China on Aug. 22, 2014. The specifications of the above referenced patent applications are incorporated herein by reference in their entirety.

FIELD OF THE INVENTION

The invention relates to fields of compound preparation, specially relates to 2,6-dinitrogen-containing substituted purine derivatives, method for preparing the same, pharmaceutical compositions and uses thereof.

BACKGROUND OF THE INVENTION

Malignant tumor (cancer) is one of the main diseases to seriously influence human health and threaten human life currently. More than 5 million people die of cancer all over the world every year. Although there already have some therapeutic means such as surgery, radiotherapy, chemotherapy and so on, their cure rate is generally not high. Wherein, the chemotherapy is the main treatment means, however it exists some deficiencies such as poor selectivity, severe side effects and the like. Therefore, it is becoming a research hotspot to find antitumor medicament having lower toxicity, mild side effect, higher anticancer activity and good stability, etc.

PI3K is a complicated large family, is also one of targets of targeting anti-tumor pharmaceutical, including type I, type II and type III. Type I of PI3K is divided into two subtypes as IA and IB, which respectively transmit signals from tyrosine kinase linked receptor and G protein linked receptor, and its effect is to catalyze phosphorylation of phosphatidyl inositol (P1) at D3 position, and convert substrate PIP2 into PIP3. P13K of Type IA is a dimer protein consist of catalytic subunit P110 and regulatory subunit P85, with double activities of lipoid kinase and protein kinase. The activity of P13K is strictly controlled by many mechanisms in normal cells. It is generally believed that inactive P85-P110 composition in resting cells is ubiquitous in cytoplasm, and waiting for appropriate signal to be activated. P13K is activated by two ways. Firstly, one of the two ways is to interact with growth factor receptor having phosphorylation tyrosine residues or to connexin, to cause conformational changes of P85-P110 dimers, and then P13K is activated. For RTK, the signal comes from activation of kinase mediated by ligand, to make tyrosine residues on the inner surface of the cell membrane produce phosphorylation. The tyrosine residues of phosphorylation immediately become binding sites of intracellular signaling proteins, and are activated by combinating with $SH_2$ structure domain of P85 to make P85-P110 compounds gathered on the cell membrane, the second way is to combine Ras with P110 directly to make P13K activation.

After PI3K is activated, the second messenger PIPa is generated on cell membranes, PIPa is combined with a signal protein Akt containing PH structure domain and phosphoinositide dependent kinase-1 (PDK1) in cells, to make PDK1 phosphorylated Ser473 and Thr308 of Akt protein, and make Akt activation. Akt is also referred to as protein kinase B (PKB), is serine/threonine kinase with relative molecular mass of 60 000, and is a homologue of v-akt, and has the similarity with protein kinase A (PKA) and protein kinase C (PKC). Akt can directly phosphorylate various transcription factors, and can inhibit expression of apoptosis gene and enhance expression of anti-apoptotic gene by regulating the transcription factors, so as to promote cell survival. For example, transcription factor FKHRLI can promote transcription of apoptosis gene Fas-1 and Bim, Akt is transferred from cell membrane to cell nucleus and phosphorylates FKHRL1 after being activated. Phosphorylated FKHRL1 is transported out of the cell nucleus and chelated with cytoplasmic protein 14-3-3 together, and then lost transcription function to target genes. In addition, Akt can also positively regulate two transcription factors such as NF-κB and Bc1-2. NF-κB has something to do with cell differentiation, apoptosis and survival caused by many cytokines and growth factors. Under normal conditions, NF-κB is combined with its inhibitory factor I-κB in cytoplasm, and loses transcriptional activity. Akt can activate IKK (the kinase of 1-κB) by phosphorylation, and results in phosphorylation and, degradation of I-κB, and separates with NF-κB, and then the released NF-κB is translocated into the cell nucleus and induces expression of target gene. Akt1KK is necessary for mediating degradation of I-κB and activation of NF-κB, and is the key regulator in the process of NF-κB dependent gene transcription, and plays an important role in promoting tumor cell survival.

In addition to the expression of influencing apoptosis and anti-apoptotic genes, Akt can also promote cell survival directly by phosphorylating pro-apoptosis protein Bad. Bad is an apoptotic protein in EC1-2 family, and can promote cell apoptosis by combining and antagonising the Bc1-2 and the EC1-K. Akt can phosphorylate the Ser136 residues of Bad directly or by Raf-1 and P65PAK, to make the Bad chelate with the 14-3-3 protein in cytoplasm, to terminate the antagonism of Bad to the Bc1-2 or the Bc1-XI on mitochondrial membrane, and to make the released Bc1-2 or Bc1-XI restore the anti-apoptosis function. Besides, Akt can directly inhibit activities of cysteine aspartase-9 (caspase-9). Pro-caspase-9 loses its activity after being phosphorylated by Akt, and the downstream signal is interrupted.

WO0103456, WO2003072557, WO2005113554, WO2006122806, WO2006046040, WO2007044729, WO2008144463 and WO200911824 disclose compounds with PI3K inhibitors and antitumor activity thereof.

$N^6$ disubstituted purine derivatives used for treating the allergic disease are disclosed in U.S. Pat. No. 4,853,386; 6-cyclopropylamino-9H-purine derivatives having antiviral activity are disclosed in JP2003-55377A and JP 2003-119197A. Glycosylated purine derivatives having anti-inflammatory effects are disclosed in J. Org. Chem., pages 3212~3215, Vol. 69, 2004. $N^2$-butylphenyl-2'-deoxy purine derivatives having activities of DNA α polymerase of eukaryotic cells are disclosed in J. Med. Chem. pages 175~181, vol. 27, 1984. 2,6,9-trisubstituted purine derivatives are disclosed in Tetraheron Letters/1827~1830, vol. 39, 1998. N²-quinoline or isoquinoline substituted purine derivatives having antitumour activity and the preparation thereof, as XC302, are disclosed in CN1880315A. 2, 6-dinitrogen-containing substituted purine derivatives having antitumor activity and its preparation method are disclosed in CN101289449A.

SUMMARY OF THE INVENTION

The purpose of present invention is to provide a 2, 6-dinitrogen-containing substituted purine derivatives of formula (I) or its pharmaceutical salts or hydrates thereof,

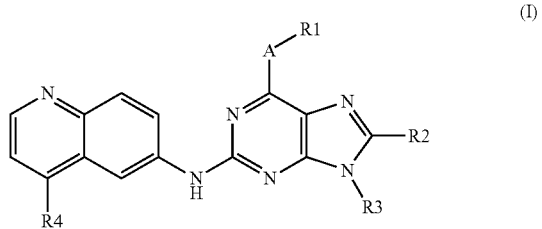

(I)

Wherein, R1 is selected from any one of unsubstituted C1~C6 straight or branched alkyl; or C1~C6 straight or branched alkyl substituted by methoxyl, C3~C6-cycloalkyl, hydroxyl or amino; or unsubstituted C3~C6-cycloalkyl; or C3~C6-cycloalkyl substituted by carboxylic carbomethoxy or carboxylic; or phenyl substituted by methoxy; unsubstituted morpholinyl; unsubstituted piperazinyl; unsubstituted piperidyl; unsubstituted pyrrolidinyl; piperidyl substituted by hydroxyl or acylamino;

R2 is H;

R3 is selected from H, tetrahydropyrane, trifluoroethyl or piperidyl;

R4 is selected from H; unsubstituted C1~C6 straight alkyl; unsubstituted C3~C6 cycloalkyl; unsubstituted phenyl, phenyl substituted by carboxylic carbomethoxy, C1~C6 straight alkoxy, bis C1~C6 straight alkoxy, C1~C6 straight alkyl sulphanyl or halogen atoms; 1,3-benzodioxol; unsubstituted morpholinyl; unsubstituted piperazinyl; or piperazinyl substituted by methyl.

A is N or O; but A is N, R4 is not equal to H.

In the preferred solution of the present invention, R4 is selected from any one of methyl, ethyl, cyclopentylmethyl, cyclopropyl, phenyl, p-methylbenzoate group, m-methylbenzoate group, o-methoxyphenyl, m-methoxyphenyl, p-methoxyphenyl, m-ethoxyphenyl, dimethoxyphenyl, o-methylthiophenyl, m-methylthiophenyl, m-fluorophenyl, p-fluorophenyl, 1,3-benzodioxol, morpholinyl, piperazinyl and methyl piperazinyl.

In the preferred solution of the present invention, the pharmaceutical salt is selected from any one of acidic addition salts produced by organic acid or inorganic acid, or alkaline addition salts produced by organic alkali or inorganic alkali, preferably the acid is selected from any one of hydrochloric acid, sulfuric acid, hydrobromic acid, methanesulfonic acid, benzenesulfonic acid, p-toluenesulfonic acid, maleic acid, fumaric acid, lactic acid, citric acid.

In the preferred solution of the present invention, the compounds of formula (I) are selected from the following compounds:
1) N6-cyclopropyl-N2-(4-morpholinyl quinoline-6-yl)-9H-purine-2,6-diamine;
2) N6-cyclopropyl-N2-(4-(piperazin-1-yl) quinoline-6-yl)-9H-purine-2, 6-diamine;
3) N-(6-isopropoxy-9H-purine-2-yl) quinoline-6-amine;
4) N-(6-Cyclopentyloxy-9H-purine-2-yl) quinoline-6-amine;
5) N-(6-isopropoxy-9H-purine-2-yl)-4-(phenyl-1-yl) quinoline-6-amine;
6) N-(6-isopropoxy-9H-purine-2-yl)-4-(phenyl-1-yl) quinoline-6-amine-methanesulfonate;
7) N6-cyclopropyl-N2-(4-methylquinoline-6-yl)-9H-purine-2, 6-diamine dihydrate dimethanesulfonate;
8) N6-cyclopropyl-N2-(4-ethylquinoline-6-yl)-9H-purine-2, 6-diamine dihydrate dimethanesulfonate;
9) N6-cyclopropyl-N2-(4-cyclopropyl quinoline-6-yl)-9H-purine-2, 6-diamine dihydrate dimethanesulfonate;
10) 2-(4-(4-methoxyphenyl) quinoline-6-yl amino)-9H-purine-6-ol-methanesulfonate;
11) 4-[1,3]benzodioxol-5-yl)-N-(6-isopropoxy-9H-purine-2-yl) quinoline-6-amine-methanesulfonate;
12) 2-(4-(3-methoxy phenyl) quinoline-6-yl amino) 9H-purine-6-ol-methanesulfonate;
13) 4-(3-fluorophenyl)-N-(6-isopropoxy-9H-purine-2-yl) quinoline-6-amine-methanesulfonate;
14) 4-(4-fluorophenyl)-N-(6-isopropoxy-9H-purine-2-yl) quinoline-6-amine-methanesulfonate;
15) 4-(3, 4-dimethoxy phenyl)-N-(6-isopropoxy-9H-purine-2-yl) quinoline-6-amine-methanesulfonate;
16) 2-(4-([1,3]benzodioxol-5-yl) quinoline-6-yl amino)-9H-purine-6-ol-methanesulfonate;
17) N-(6-isopropoxy-9H-purine-2-yl)-4-(piperazine-1-yl) quinoline-6-amine-methanesulfonate;
18) N-(6-isopropoxy-9H-purine-2-yl)-4-(4-methyl piperazine-1-yl) quinoline-6-amine-methanesulfonate;
19) 1-(2-(4-phenyl quinoline-6-yl amino)-9H-purine-6-yl) piperidine-4-ol;
20) 1-(2-(4-phenyl quinoline-6-yl amino)-9H-purine-6-yl) piperidine-3-amide;
21) 1-(2-(4-phenyl quinoline-6-yl amino)-9H-purine-6-yl amino)cyclopropane carboxylic acid methyl ester;
22) 1-(2-(4-phenyl quinoline-6-yl amino)-9H-purine-6-yl amino)cyclopropane carboxylic acid;
23) N6-cyclopropyl-N2-(4-phenyl quinoline-6-yl)-9H-purine-2,6 diamine;
24) N-(6-phenoxy-9H-purine-2-yl)-4-(piperazine-1-yl) quinoline-6-amine;
25) N-(6-isopropoxy-9H-purine-2-yl)-4-(piperazine-1-yl) quinoline-6-amine;
26) 4-(6-(6-(cyclopropyl amino)-9H-purine-2-yl amino) quinoline-4-yl) p-methyl benzoate;
27) 4-(6-(6-(cyclopropyl amino)-9H-purine-2-yl amino) quinoline-4-yl) m-methyl benzoate;
28) N6-cyclopropyl-N2-(4-(3-methoxy phenyl) quinoline-6-yl)-9H-purine-2, 6-diamine;
29) N6-cyclopropyl-N2-(4-(4-methoxy phenyl) quinoline-6-yl)-9H-purine-2, 6-diamine;
30) N6-cyclopropyl-N2-(4-(3-fluorophenyl) quinoline-6-yl)-9H-purine-2, 6-diamine;
31) N6-cyclopropyl-N2-(4-phenyl quinoline-6-yl)-9-(2, 2, 2-trifluoroethyl)-9H-purine-2, 6-diamine;
32) N6-cyclopropyl-N2-(4-phenyl quinoline-6-yl)-9-(piperidine-4-yl)-9H-purine-2, 6-diamine;
33) N6-(3-methoxy propyl)-N2-(4-phenyl quinoline-6-yl)-9H-purine-2, 6-diamine;
34) N6-(2-methoxy ethyl)-N2-(4-phenyl quinoline-6-yl)-9H-purine-2, 6-diamine;
35) 2-(2-(4-phenyl quinoline-6-yl amino)-9H-purine-6-yl amino) ethanol;

36) N6-(2-aminoethyl)-N2-(4-phenyl quinoline-6-yl)-9H-purine-2, 6-diamine;
37) N6-cyclobutyl-N2-(4-(3-methoxy phenyl) quinoline-6-yl)-9H-purine-2, 6-diamine;
38) N6-cyclobutyl-N2-(4-(4-fluorophenyl) quinoline-6-yl)-9H-purine-2, 6-diamine;
39) 3-(2-(4-phenyl quinoline-6-yl amino)-9H-purine-6-yl amino) propyl-1-ol;
40) N6-cyclobutyl-N2-(4-phenyl quinoline-6-yl)-9H-purine-2, 6-diamine;
41) N6-cyclopropyl-N2-(4-(3-ethoxy phenyl) quinoline-6-yl)-9H-purine-2, 6-diamine;
42) N6-cyclopropyl-N2-(4-(3, 4-dimethoxy phenyl) quinoline-6-yl)-9H-purine-2, 6-diamine;
43) N2-(4-(benzo[1,3]dioxole-5-yl) quinoline-6-yl)-N6-cyclopropane-9H-purine-2, 6-diamine;
44) N6-cyclopropyl-N2-(4-(2-methoxy phenyl) quinoline-6-yl)-9H-purine-2, 6-diamine;
45) N6-cyclopropyl-N2-(4-(2-(methylthio)phenyl) quinoline-6-yl)-9H-purine-2, 6-diamine;
46) N6-cyclopropyl-N2-(4-(3-(methylthio)phenyl) quinoline-6-yl)-9H-purine-2, 6-diamine;
47) N6-cyclopropyl-N2-(4-phenyl quinoline-6-yl)-9H-purine-2, 6-diammonium salt dihydrate dimethanesulfonate;
48) N-(6-cyclobutyl-9H-purine-2-yl) quinoline-6-amine;
49) N-(6-cyclobutyl-9H-purine-2-yl)-4-phenyl quinoline-6-amine;
50) N6-(cyclopentyl methyl)-N2-(4-phenyl quinoline-6-yl)-9H-purine-2, 6-diamine;
51) N6-isopropyl-N2-(4-phenyl quinoline-6-yl)-9H-purine-2, 6-diamine;
52) 4-phenyl-N-(6-(pyrrolidine-1-yl)-9H-purine-2-yl) quinoline-6-amine;
53) N-(6-isopropoxy-9H-purine-2-yl) quinoline-6-amine;
54) N-(6-(pentyl-3-yl oxyl)-9H-purine-2-yl)-4-phenyl quinoline-6-amine;
55) N6-cyclopentyl-N2-(4-phenyl quinoline-6-yl)-9H-purine-2, 6-diamine;
56) N-(6-cyclohexyloxy-9H-purine-2-yl)-4-phenyl quinoline-6-amine;
57) N-(6-isopropoxy-9H-purine-2-yl)-4-phenyl quinoline-6-amine dihydrate dimethanesulfonate;
58) N-(6-morpholine-9H-purine-2-yl)-4-phenyl quinoline-6-amine;
59) N-(6-morpholine-9H-purine-2-yl)-4-phenyl quinoline-6-amine dihydrate dimethanesulfonate;
60) 2-(4-phenyl quinoline-6-yl amino)-9H-purine-6-ol.

It is another purpose of the present invention to provide a pharmaceutical composition composed of 2, 6-dinitrogen-containing substituted purine derivative of formula (I) or pharmaceutical salt or hydrate and pharmaceutical acceptable carrier thereof.

In the preferred solution of the present invention, the dosage form of the pharmaceutical composition is selected from any one of a tablet, a capsule, a pill, an oral liquid preparation, a granule, a powder, an injection, an implant or an external preparation.

In the preferred solution of the present invention, the pharmaceutical composition is selected from any one of injection, transfusion, freeze-dried powder injection, oral liquid preparation, tablet, capsule, granule, pill, powder, syrup, mixture, sprays, distillate formula, medical tea, gels, paste, liniment, lotion, daub, fumigants, suppositories, emplastrum, condensate paste and ointments.

The pharmaceutical composition of the present invention can be obtained by any of preparations technical means known very well in the art.

If necessary, the pharmaceutical composition of the present invention also includes a pharmaceutically acceptable carrier, the dosages and types of the pharmaceutical acceptable carrier is determined according to the factors of physicochemical properties and contents of effective components in Chinese medicine composition, formulation types and so on.

The pharmaceutically acceptable carriers of the present invention are conventional excipients or adjuvants for preparing the preparations in the art. The conventional excipients or adjuvants include but not limit to filler (diluent), lubricants (glidants or antitack agent), dispersant, humectant, adhesive, modifier, solubilizer, antioxidant, bacteriostat, emulsifier, etc. Wherein, the adhesive, such as syrup, arabic gum, gelatin, sorbitol, tragacanth, cellulose or its derivatives, gelatin mucilage, starch slurry or polyvinylpyrrolidone, preferably the cellulose derivative is selected from any one of microcrystalline cellulose, sodium carboxymethylcellulose, ethylcellulose or hydroxypropyl methylcellulose, preferably the starch derivative is selected from any one or its combination of sodium carboxymethyl starch, sodium starch glycolate, pregelatinized starch, modified starch, hydroxypropyl starch, corn starch; the filler such as lactose, powdered sugar, dextrin, starch or its derivatives, cellulose or its derivatives, inorganic calcium salt, sorbitol or glycine etc. preferably the inorganic calcium salt is selected from any one of calcium sulfate, calcium phosphate, calcium hydrogenphosphate, sedimentary calcium carbonate, preferably the cellulose derivatives are selected from any one of microcrystalline cellulose, sodium carboxymethyl cellulose, ethyl cellulose or hydroxypropyl methyl cellulose, preferably the starch derivatives are selected from any one or its combination of sodium carboxymethyl starch, sodium starch glycolate, pregelatinized starch, modified starch, hydroxypropyl starch, corn starch; lubricant such as aerosil, magnesium stearate, talcum powder, aluminum hydroxide, boric acid, hydrogenated vegetable oil, polyethylene glycol, etc.; disintegrating agent, such as starch or its derivatives, polyvinylpyrrolidone or microcrystalline cellulose, preferably the starch derivatives are selected from any one or its combination of sodium carboxymethyl starch, sodium starch glycolate, pregelatinized starch, modified starch, hydroxypropyl starch, corn starch; humectant such as sodium dodecyl sulfate, water or alcohol, etc.; antioxidants such as sodium sulfite, sodium bisulfite, sodium metabisulfite, dibutyl benzoic acid, etc.; bacteriostat such as 0.5% phenol, 0.3% cresol, and 0.5% chloretone etc.; acid-base regulator such as hydrochloric acid, citric acid, potassium (sodium) hydroxide, sodium citrate, sodium dihydrogen phosphate, disodium hydrogen phosphate, etc; emulsifier, such as polysorbate-80, sorbitan oleate, Pluronic F-68, lecithin and soybean phospholipids etc.; solubilizer such as tween-80, bile and glycerin etc.

Another purpose of the present invention is to provide an application for 2, 6-dinitrogen-containing substituted purine derivatives of formula (I) or pharmaceutical salts or hydrates or pharmaceutical composition in preparation of a medicament for treatment or prophylaxis of tumor diseases.

In the preferred solution of the present invention, the tumor diseases are selected from any one or its combination of lung cancer, liver cancer, leukemia, osteocarcinoma, pancreas cancer, skin cancer, melanoma, metrocarcinoma, oophoroma, rectal carcinoma, gastric carcinoma, colon cancer, breast carcinoma, salpingo carcinoma, endometrium carcinoma, cervix carcinoma, vagina carcinoma, carcinoma of vulva, esophagus carcinoma, small intestine carcinoma, endocrinium carcinoma, soft tissue sarcoma, urethra carcinoma, prostatic cancer, lymphocytoma, bladder cancer, kidney or ureter cancer, tumors of vertebral column, tumors in the neuroglia of the brain, and pituitary adenoma.

Another purpose of the present invention is to provide the method for preparing 2, 6-dinitrogen-containing substituted purine derivatives of formula (I) or the pharmaceutical salts or hydrate thereof, including the following steps:

1) reacting compound (a) with R3 under catalysis of catalyst p-toluene sulfonic acid or pyridine salt of p-toluene sulfonic acid, and then condensating with HA-R1 to obtain compound (b) at temperature of 20~100° C. in the presence of depickling solvent such as triethylamine, sodium carbonate, potassium carbonate or sodium bicarbonate;

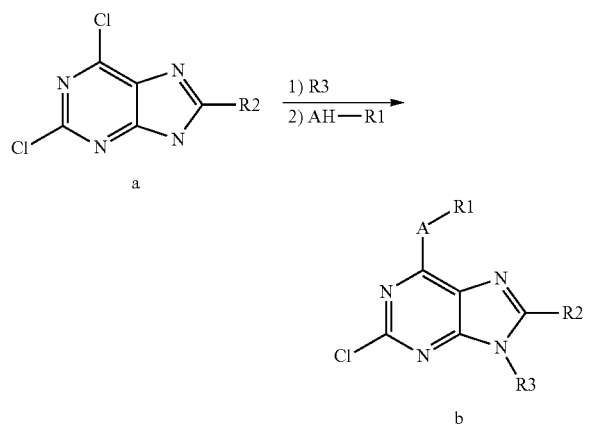

2) undergoing catalytic coupling reaction of compounds (b) and (c) with catalyst, ligand, alkali (base), aprotic solvent at temperature of 15~150° C. and then forming salts with acids to obtain compound (d),

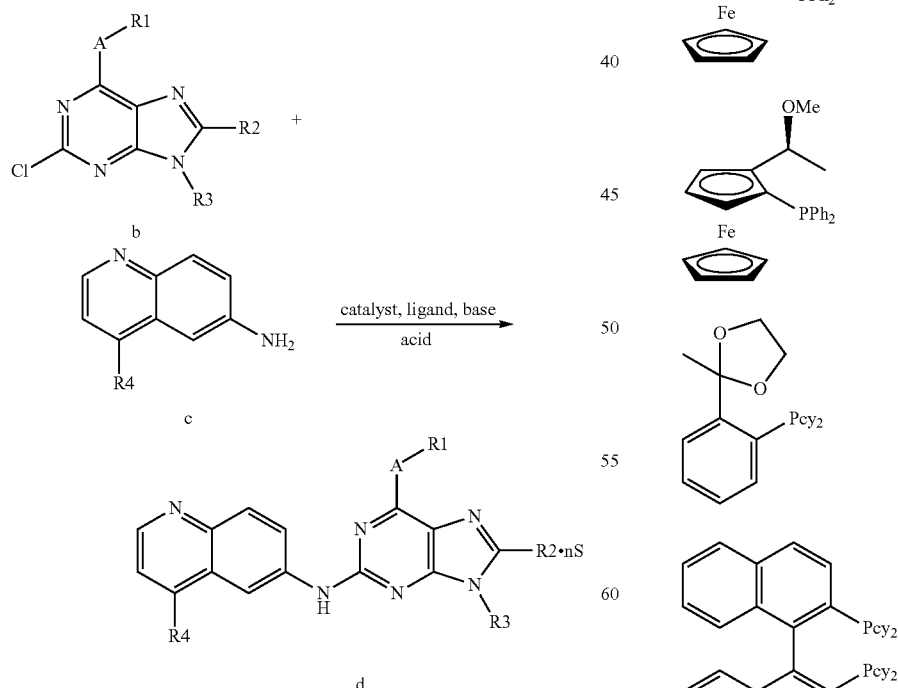

wherein, in the catalytic coupling reaction, the ligand is selected from any one of tri-o-tolylphosphine (P(o-tolyl)3), tri-tert-butylphosphine (P(Bu-t)3), 2,2'-diphenylphosphine-1,1'-binaphthalene (BINAP), 1,1'-diphenylphosphine-ferrocene (DPPF), bis(2-diphenylphosphinophenyl) ether (DPEphos), 9,9-dimethyl-4,5-diphenylphosphine xanthone (Xantphos), compounds of ligand formula (1) to formula (11),

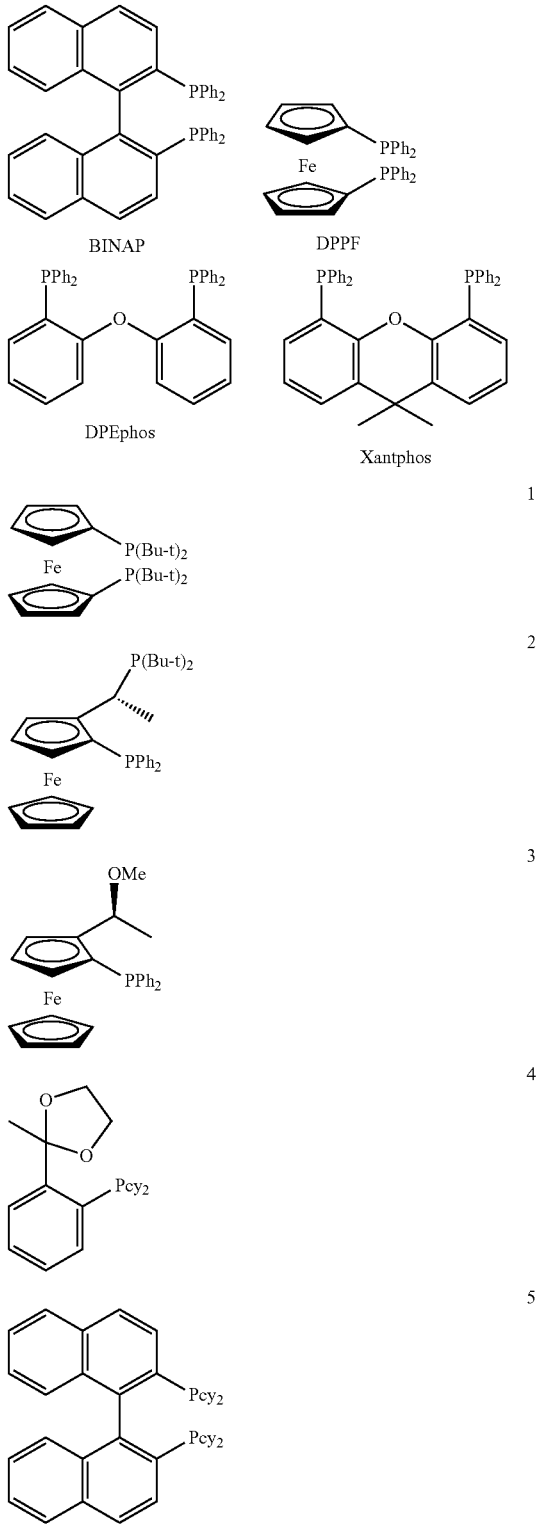

-continued

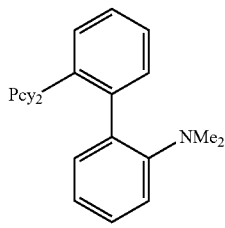

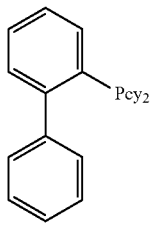

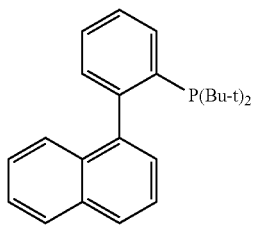

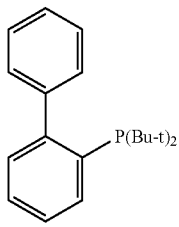

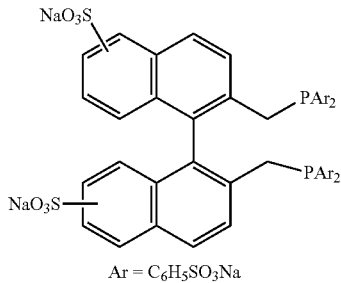

Ar = C₆H₅SO₃Na

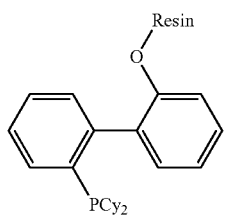

The catalyst is transition metal catalysts palladium or nickel such as PdCl₂, Pd(OAc)₂, Pd₂(dba)₃, Ni(OAc)₂ or Ni/C.

The alkali (base) is selected from any one or its combination of sodium tert-butoxide, potassium tert-butoxide, potassium carbonate, cesium carbonate and tripotassium phosphate;

The acid in salt-forming with acids is selected from any one or its combination of hydrochloric acid, sulphuric acid, hydrobromic acid, methanesulfonic acid, benzenesulfonic acid, paratoluenesulfonic acid, maleic acid, fumaric acid, lactic acid, citric acid;

3) Neutralizing compound (d) with sodium carbonate, potassium carbonate, sodium hydroxide or potassium hydroxide, to produce compound (I);

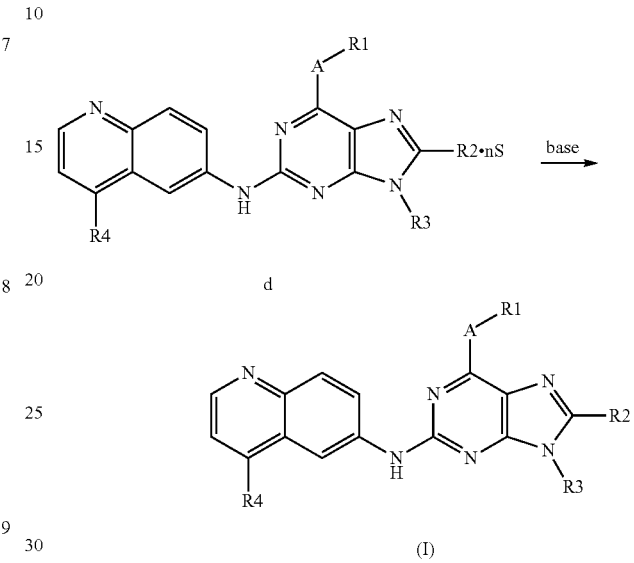

Wherein, R1 is unsubstituted C1~C6 straight or branched alkyl; or C1~C6 straight or branched alkyl substituted by methoxyl, C3~C6-cycloalkyl, hydroxyl or amino; or unsubstituted C3~C6-cycloalkyl; or C3~C6-cycloalkyl substituted by carboxylic carbomethoxy or carboxylic; or phenyl substituted by methoxy; unsubstituted morpholinyl; unsubstituted piperazinyl; unsubstituted piperidyl; piperidyl substituted by hydroxyl or acylamino; unsubstituted pyrrolidinyl;

R2 is H;

R3 is H, 2,3-dihydropyrane, trifluoroethyl or piperidyl;

R4 is H; unsubstituted C1~C6 straight alkyl; unsubstituted C3~C6 cycloalkyl; unsubstituted phenyl; phenyl substituted by carboxylic carbomethoxy, C1~C6 straight alkoxy, bis C1~C6 straight alkoxy, C1~C6 straight alkyl sulphanyl or halogen atoms; 1, 3-benzodioxol; unsubstituted morpholinyl; unsubstituted piperazinyl; or piperazinyl substituted by methyl;

A is N or O; when A is N, R4 is not equal to H.

In the preferred solution of the present invention, the reacting molar ratio of compound (a) to R3 is 1:1~5, preferably the molar ratio of the compound (a) to HA-R1 is 1:1~5, more preferably the temperature of condensation reaction is 40~60° C.

In the preferred solution of the present invention, the molar ratio of compound (b) to compound (c) is 1:0.5~2.

In the preferred solution of the present invention, the temperature of coupling reaction is 55~120° C., preferably using microwave heating.

In the preferred solution of the present invention, the aprotic solvents is selected from any one or its combination of tetrahydrofuran, isopropyl ether, glycol dimethyl ether, dioxane, pyridine, 1-methyl-2-pyrrolidone (NMP), 1,3-dimethyltrimethylene urea (DMPU), toluene or xylene.

In the preferred solution of the present invention, the molar ratio of compound (b) to acid is 1:1~10.

In the preferred solution of the present invention, the acid is selected from any one or its combination of hydrochloric acid, sulfuric acid, hydrobromic acid, methanesulfonic acid, benzene sulfonic acid, paratoluenesulfonic acid, maleic acid, fumaric acid, lactic acid, citric acid;

In order to clearly illustrate the protected scope of the present invention, the compounds of the structure of formula (I) and their serial numbers are as follows.

| No | Name of the compounds |
|---|---|
| MED1007-32 | N6-cyclopropyl-N2-(4-morpholine quinoline-6-yl)-9H-purine-2,6-diamine |
| MED1007-33 | N6-cyclopropyl-N2-(4-(piperazin-1-yl) quinoline-6-yl)-9H-purine-2,6-diamine |
| MED1007-34 | N-(6-isopropyl-9H-purine-2-yl) quinoline-6-amine |
| MED1007-35 | N-(6-cyclopentyloxy-9H-purine-2-yl) quinoline-6-amine |
| MED1007-51 | N-(6-isopropoxy-9H-purine-2-yl)-4-(phenyl-1-yl) quinoline-6-amine |
| MED1007-108 | N-(6-isopropoxy-9H-purine-2-yl)-4-(phenyl-1-yl) quinoline-6-amine-methanesulfonate |
| MED1007-113 | N6-cyclopropyl-N2-(4-methyl quinoline-6-yl)-9H-purine-2,6-diamine dihydrate dimethanesulfonate |
| MED1007-114 | N6-cyclopropyl-N2-(4-ethyl quinoline-6-yl)-9H-purine-2,6-diamine dihydrate dimethanesulfonate |
| MED1007-115 | N6-cyclopropyl-N2-(4-cyclopropyl quinoline-6-yl)-9H-purine-2,6-diamine dihydrate dimethanesulfonate |
| MED1007-132 | 2-(4-(4-methoxy phenyl) quinoline-6-yl amino)-9H-purine-6-ol-methanesulfonate |
| MED1007-133 | 4-([1,3] benzodioxol-5-yl)-N-(6-isopropoxy-9H-purine-2-yl) quinoline-6-amine-methanesulfonate |
| MED1007-134 | 2-(4-(3-methoxy phenyl) quinoline-6-yl amino) 9H-purine-6-ol-methanesulfonate |
| MED1007-135 | 4-(3-fluorophenyl)-N-(6-isopropoxy-9H-purine-2-yl) quinoline-6-amine-methanesulfonate |
| MED1007-136 | 4-(4-fluorophenyl)-N-(6-isopropoxy-9H-purine-2-yl) quinoline-6-amine-methanesulfonate |
| MED1007-137 | 4-(3,4-dimethoxy phenyl)-N-(6-isopropoxy-9H-purine-2-yl) quinoline-6-amine-methanesulfonate |
| MED1007-139 | 2-(4-([1,3] benzodioxol-5-yl) quinoline-6-yl amino)-9H-purine-6-ol-methanesulfonate |
| MED1007-142 | N-(6-isopropoxy-9H-purine-2-yl)-4-(piperazine-1-yl) quinoline-6-amine-methanesulfonate |
| MED1007-143 | N-(6-isopropoxy-9H-purine-2-yl)-4-(4-methyl piperazine-1-yl) quinoline-6-amine-methanesulfonate |
| MED1007-148 | 1-(2-(4-phenyl quinoline-6-yl amino)-9H-purine-6-yl) piperidine-4-ol |
| MED1007-149 | 1-(2-(4-phenyl quinoline-6-yl amino)-9H-purine-6-yl) piperidine-3-amide |
| MED1007-15 | 1-(2-(4-phenyl quinoline-6-yl amino)-9H-purine-6-yl amino) cyclopropane carboxylic acid methyl ester |
| MED1007-152 | 1-(2-(4-phenyl quinoline-6-yl amino)-9H-purine-6-yl amino) cyclopropane carboxylic acid |
| MED1007-31 | N6-cyclopropyl-N2-(4-phenyl quinoline-6-yl)-9H-purine-2,6 diamine |
| MED1007-54 | N-(6-phenoxy-9H-purine-2-yl)-4-(piperazine-1-yl) quinoline-6-amine |
| MED1007-58 | N-(6-isopropoxy-9H-purine-2-yl)-4-(piperazine-1-yl) quinoline-6-amine |
| MED1007-59 | 4-(6-(6-(cyclopropyl amino)-9H-purine-2-yl amino) quinoline-4-yl) p-methyl benzoate |
| MED1007-60 | 4-(6-(6-(cyclopropyl amino)-9H-purine-2-yl amino) quinoline-4-yl) m-methyl benzoate |
| MED1007-61 | N6-cyclopropyl-N2-(4-(3-methoxy phenyl) quinoline-6-yl)-9H-purine-2,6-diamine |
| MED1007-63 | N6-cyclopropyl-N2-(4-(4-methoxy phenyl) quinoline-6-yl)-9H-purine-2,6-diamine |
| MED1007-64 | N6-cyclopropyl-N2-(4-(3-fluoro phenyl) quinoline-6-yl)-9H-purine-2,6-diamine |
| MED1007-65 | N6-cyclopropyl-N2-(4-phenyl quinoline-6-yl)-9-(2,2,2-trifluoroethyl)-9H-purine-2,6-diamine |
| MED1007-66 | N6-cyclopropyl-N2-(4-phenyl quinoline-6-yl)-9-(piperidine-4-yl)-9H-purine-2,6-diamine |
| MED1007-67 | N6-(3-methoxy propyl)-N2-(4-phenyl quinoline-6-yl)-9H-purine-2,6-diamine |
| MED1007-68 | N6-(2-methoxy ethyl)-N2-(4-phenyl quinoline-6-yl)-9H-purine-2,6-diamine |

| No | Name of the compounds |
|---|---|
| MED1007-69 | 2-(2-(4-phenyl quinoline-6-yl amino)-9H-purine-6-yl amino) ethanol |
| MED1007-70 | N6-(2-aminoethyl)-N2-(4-phenyl quinoline-6-yl)-9H-purine-2,6-diamine |
| MED1007-71 | N6-cyclobutyl-N2-(4-(3-methoxy phenyl) quinoline-6-yl)-9H-purine-2,6-diamine |
| MED1007-72 | N6-cyclobutyl-N2-(4-(4-fluorophenyl) quinoline-6-yl)-9H-purine-2,6-diamine |
| MED1007-73 | 3-(2-(4-phenyl quinoline-6-yl amino)-9H-purine-6-yl amino) propyl-1-ol |
| MED1007-75 | N6-cyclobutyl-N2-(4-phenyl quinoline-6-yl)-9H-purine-2,6-diamine |
| MED1007-83 | N6-cyclopropyl-N2-(4-(3-ethoxy phenyl) quinoline-6-yl)-9H-purine-2,6-diamine |
| MED1007-84 | N6-cyclopropyl-N2-(4-(3,4-dimethoxy phenyl) quinoline-6-yl)-9H-purine-2,6-diamine |
| MED1007-85 | N2-(4-([1,3] benzodioxol-5-yl) quinoline-6-yl)-N6-cyclopropane-9H-purine-2,6-diamine |
| MED1007-86 | N6-cyclopropyl-N2-(4-(2-methoxy phenyl) quinoline-6-yl)-9H-purine-2,6-diamine |
| MED1007-87 | N6-cyclopropyl-N2-(4-(2-(methylthio) phenyl) quinoline-6-yl)-9H-purine-2,6-diamine |
| MED1007-88 | N6-cyclopropyl-N2-(4-(3-(methylthio) phenyl) quinoline-6-yl)-9H-purine-2,6-diamine |
| MED1007-91 | N6-cyclopropyl-N2-(4-phenyl quinoline-6-yl)-9H-purine-2,6-diammonium salt dihydrate dimethanesulfonate |
| MED1007-97 | N-(6-cyclobutyl-9H-purine-2-yl) quinoline-6-amine |
| MED1007-98 | N-(6-cyclobutyl-9H-purine-2-yl)-4-phenyl quinoline-6-amine |
| MED1007-99 | N6-(cyclopentyl methyl)-N2-(4-phenyl quinoline-6-yl)-9H-purine-2,6-diamine |
| MED1007-101 | N6-isopropyl-N2-(4-phenyl quinoline-6-yl)-9H-purine-2,6-diamine |
| MED1007-103 | 4-phenyl-N-(6-(pyrrolidine-1-yl)-9H-purine-2-yl) quinoline-6-amine |
| MED1007-104 | N-(6-isopropoxy-9H-purine-2-yl) quinoline-6-amine |
| MED1007-105 | N-(6-(pentyl-3-yl oxy)-9H-purine-2-yl)-4-phenyl quinoline-6-amine |
| MED1007-106 | N6-cyclopentyl-N2-(4-phenyl quinoline-6-yl)-9H-purine-2,6-diamine |
| MED1007-107 | N-(6-cyclohexyloxy-9H-purine-2-yl)-4-phenyl quinoline-6-amine |
| MED1007-108 | N-(6-isopropoxy-9H-purine-2-yl)-4-phenyl quinoline-6-amine dihydrate dimethanesulfonate |
| MED1007-109 | N-(6-morpholine-9H-purine-2-yl)-4-phenyl quinoline-6-amine |
| MED1007-109S | N-(6-morpholine-9H-purine-2-yl)-4-phenyl quinoline-6-amine dihydrate dimethanesulfonate |
| MED1007-110 | 2-(4-phenyl quinoline-6-yl amino)-9H-purine-6-ol |

Unless other description, the percentage is volume/volume percent if the present invention has something to do with the percentage between the liquid and liquid; the percentage is the volume/weight percent if the invention has something to do with the percentage between liquid and solid; the percentage is weight/volume percent if the present invention has something to do with the percentage between solid and liquid; and the rest is weight/weight percent.

The $N^2,N^6$-disubstituted purine derivatives of the present invention has the inhibitory activity to PI3K, and also has the advantage such as lower toxicity, broader spectrum anticancer, higher anticancer activity and good stability and so on.

DETAILED DESCRIPTION AND PREFERRED EMBODIMENTS THEREOF

Hereafter, the present invention will specifically be described with reference to examples. The examples are given only for illustration of the technical solution of the present invention and should not be construed to limit the present invention.

Example 1

Preparation of N-(6-isopropoxy-9H-purine-2-yl)-4-(phenyl-1-yl) quinoline-6-amine

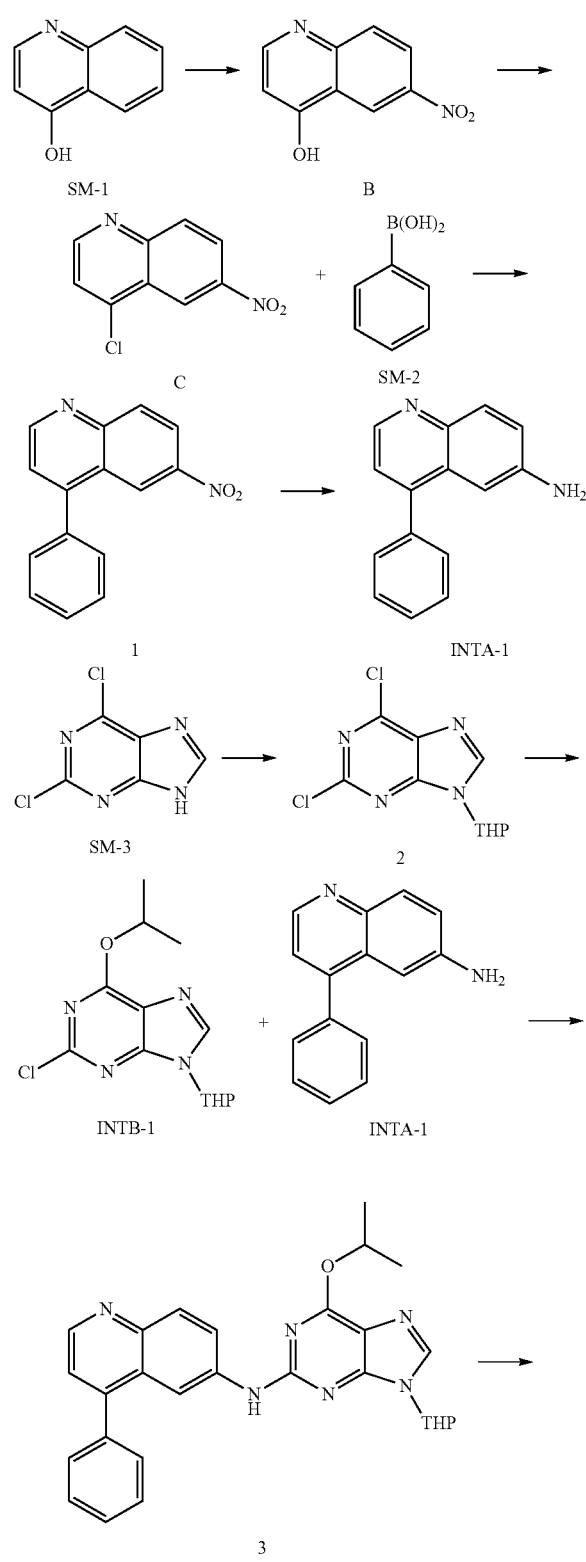

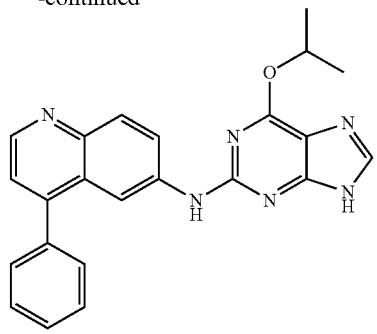

MED1007-51

The preparation method of the compound of present example includes the following steps:

1) Preparation of Compound B:
Sulphuric acid (320 ml) and nitric acid (320 ml) are added into sulphuric acid and SM-1 (260 g) at temperature of −15° C.~0° C., and stirred for 3 hours at room temperature to form a reaction mixture; ice water is added to the reaction mixture and filtered, then the filter cake is filtered to obtain the compound B (320 g, yield 95%).

2) Preparation of Compound C:
DMF solution (0.1 ml) is added into phosphorus oxychloride (30 ml) and compound B (5 g), and stirred under reflux for 3 hours to form a reaction mixture, then the reaction mixture is put into ice water and extracted with ethyl acetate, and washed with water and brine, dried with anhydrous sodium sulfate, concentrated, and then purified via SGC (purification solvent) to obtain compound C (3 g, yield 55%).

3) Preparation of Compound 1:
Pd(pph$_3$)$_4$ (18 g, 15.6 mmol) is added into dioxane solution (400 ml), compound C (33 g, 156 mmol), borophenylic acid (20 g, 156 mmol) and cesium carbonate (152 g, 468 mmol), and stirred under reflux for 18 hours to form a reaction mixture; the reaction mixture is extracted with ethyl acetate, and washed with water and brine, dried with anhydrous sodium sulfate, concentrated, then purified by SGC (purification solvent) to obtain the compound 1 (22 g, yield 56%).

4) Preparation of Compound INTA-1
Raney nickel (5 g) is added into the tetrahydrofuran:methanol (300 ml) and compound 1 (20 g), and stirred for 16 hours at room temperature under condition of hydrogen to form a reaction mixture, the reaction mixture is filtered, and concentrated, purified by SGC (purification solvent) to obtain compound INTA-1 (15 g, yield 88%).

5) Preparation of Compound 2
THP (111 g, 1320 mmol) is added into ethyl acetate (200 ml), compound SM-3 (100 g, 529 mmol) and p-toluenesulfonic acid (5 g, 26 mmol), and stirred under reflux for 0.5 hours to form a reaction mixture, then the reaction mixture is extracted with ethyl acetate, and washed with water and brine, dried with anhydrous sodium sulfate, concentrated, then purified by SGC (a purification solvent) to obtain compound 2 (130 g, yield 90%).

6) Preparation of Compound INTB-1
Sodium hydride (2.2 g, 55 mmol) is added into a tetrahydrofuran solution (30 ml) having compound 2 (10 g, 36.7 mmol) at temperature of 0° C.; and stirred for 0.5 hour at room temperature to form a reaction mixture; 2-propyl alcohol (2.4 g, 40.4 mmol) is added into the reaction mixture at temperature of −10° C., and stirred for 1 hour at temperature of 0° C.; and extracted with ethyl acetate, and washed with water and brine, concentrated, dried with anhydrous sodium sulfate, then puried by SGC (a purification solvent) to obtain compound INTB-1 (9 g, yield 80%).

7) Preparation of Compound 3

Potassium phosphate (7 g, 27.3 mmol) is added into toluene (30 ml) and compound INTB-1 (2 g, 9.1 mmol), compound INTA-1 (2.7 g, 9.1 mmol) and Pd(dppf)$_2$Cl$_2$ (1.3 g, 1.82 mmol) to form a mixture; and stirred under reflux and argon for 20 hours to form a reaction mixture; the reaction mixture is extracted with ethyl acetate, and washed with water and brine, concentrated, dried with anhydrous sodium sulfate, then puried by SGC (purified solvent) to obtain compound 3 (1.9 g, yield 45%).

8) Preparation of Compound MED1007-51

4N hydrochloric acid (5 ml) is added into a methanol (20 ml) and compound 3 (1.3 g) and stirred for 5 hours at room temperature to form a reaction mixture, a saturated aqueous sodium bicarbonate is added into the reaction mixture to adjust pH=8, and filtered and the filter cake is dried, to obtain compound MED1007-51 (0.95 g, yield 93%).

| Number | Molecular formula | Molecular weight | Confirmation parameters of structure |
|---|---|---|---|
| Compound B | $C_9H_6N_2O_3$ | 190.16 | $^1$H-NMR (400 MHz, DMSO-d6): 8.850-8.843 (d, J = 2.8 Hz, 1H), 8.443-8.414 (m, 1H), 8.067-8.049 (d, J = 7.2 Hz, 1H), 7.754-7.732 (d, J = 8.8 Hz, 1H), 6.227-6.208 (d, J = 7.6 Hz, 1H). |
| Compound C | $C_9H_5ClN_2O_2$ | 208.60 | $^1$H-NMR (400 MHz, CDCl$_3$): 9.206-9.201 (d, J = 2.0 Hz, 1H), 8.974-8.962 (d, J = 4.8 Hz, 1H), 8.558-8.536 (t, 1H), 8.298-8.275 (d, J = 9.2 Hz, 1H), 7.674-7.662 (d, J = 4.8 Hz, 1H). |
| Compound 1 | $C_{15}H_{10}N_2O_2$ | 250.2 | |
| Compound INTA-1 | $C_{15}H_{12}N_2$ | 220.27 | MS (ESI) m/z: 220.10 |
| Compound 2 | $C_{10}H_{10}Cl_2N_4O$ | 273.12 | $^1$H-NMR (400 MHz, CDCl$_3$): 8.336 (s, 1H), 5.783-5.756 (d, J = 10.8 Hz, 1H), 4.207-4.181 (d, J = 10.4 Hz, 1H), 3.817-3.761 (m, 1H), 2.192-1.663 (m, 7H). MS (ESI) m/z: 188 |
| Compound INTB-1 | $C_{13}H_{17}ClN_4O_2$ | 296.75 | $^1$H-NMR (400 MHz, CDCl$_3$): 8.097 (s, 1H), 5.746-5.720 (d, J = 10.4 Hz, 1H), 5.692-5.630 (m 1H), 4.174-4.113 (m 1H), 3.804-3.747 (m 1H), 2.130-1.945 (m 3H), 1.807-1.664 (m 3H), 1.638-0.885 (m, 7H). MS (ESI) m/z: 297.3 [M + 1]$^+$ |
| Compound 3 | $C_{28}H_{28}N_6O_2$ | 480.56 | $^1$H-NMR (400 MHz, CDCl$_3$): 8.822-8.811 (d, J = 4.4 Hz, 1H), 8.153-8.086 (m, 3H), 7.857 (s 1H), 7.579-7.451 (m, 5H), 7.291-7.263 (m, 1H), 5.479-5.448 (t, 1H), 5.287-5.225 (m, 1H), 4.148-4.113 (t, 1H), 3.712-3.659 (t, 1H), 2.046-2.027 (m, 4H), 1.773-1.625 (m, 2H), 1.408-1.336 (m, 6H), 1.277-1.242 (t, 1H). MS (m/z) MS (ESI) m/z:: 481.2 [M + 1]+ |
| MED1007-51 (INT5) | $C_{23}H_{20}N_6O$ | 396.44 | $^1$H-NMR (400 MHz, DMSO-d6): 12.743 (s 1H), 9.668 (s 1H), 8.736 (s 1H), 8.387-8.000 (m, 4H), 7.600-7.544 (m, 5H), 7.339 (s 1H), 5.037 (s, 1H), 1.221 (s, 6H). MS (ESI) m/z: 397.2 [M + 1]$^+$ |

Example 2

Preparation of N-(6-isopropoxy-9H-purine-2-yl)-4-(phenyl-1-yl) quinoline-6-amine-methanesulfonate

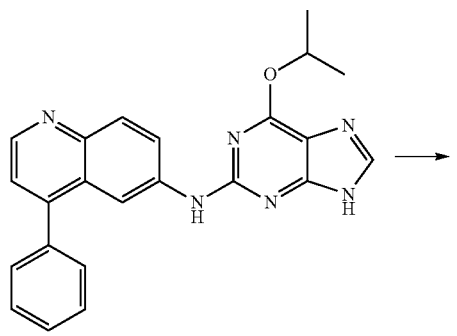

MED1007-51

→

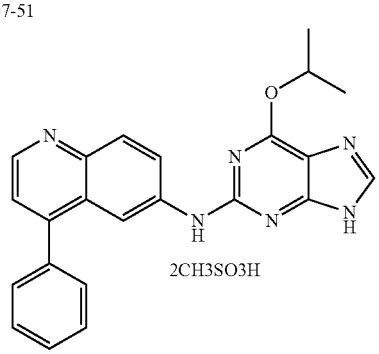

MED1007-108

The preparation method of the compound of the example includes the following steps:

Methanesulfonic acid (8.2 g, 85.9 mmol) is added into ethanol (400 ml) and compound MED1007-51 (17 g, 42.9 mmol) and stirred for 16 hours at room temperature, filtered, and then the filter cake is dried to obtain MED1007-108 (22 g, yield 88%).

Molecular formula: C$_{23}$H$_{20}$N$_6$O.2CH$_3$SO$_3$H, Molecular weight: 590.67.

$^1$H-NMR (400 MHz, DMSO-d6): 10.395 (s 1H), 9.154-9.140 (d, J=5.6 Hz, 1H), 8.820 (s 1H), 8.602-8.546 (t, 2H), 8.327-8.304 (d, J=9.2 Hz, 1H), 7.956-7.942 (d, J=5.6 Hz, 1H), 7.743-7.691 (m, 5H), 5.049 (s, 1H), 2.930 (s, 6H), 1.272 (s, 6H).

MS (ESI) m/z: 397.2 [M+1]$^+$

Example 3

The Preparation of N6-cyclopropyl-N2-(4-morpholine quinoline-6-yl)-9H-purine-2, 6-diamine

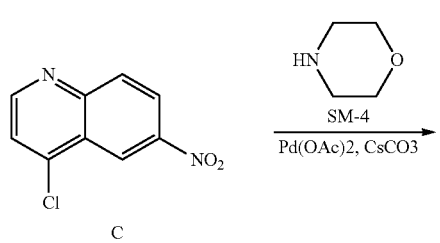

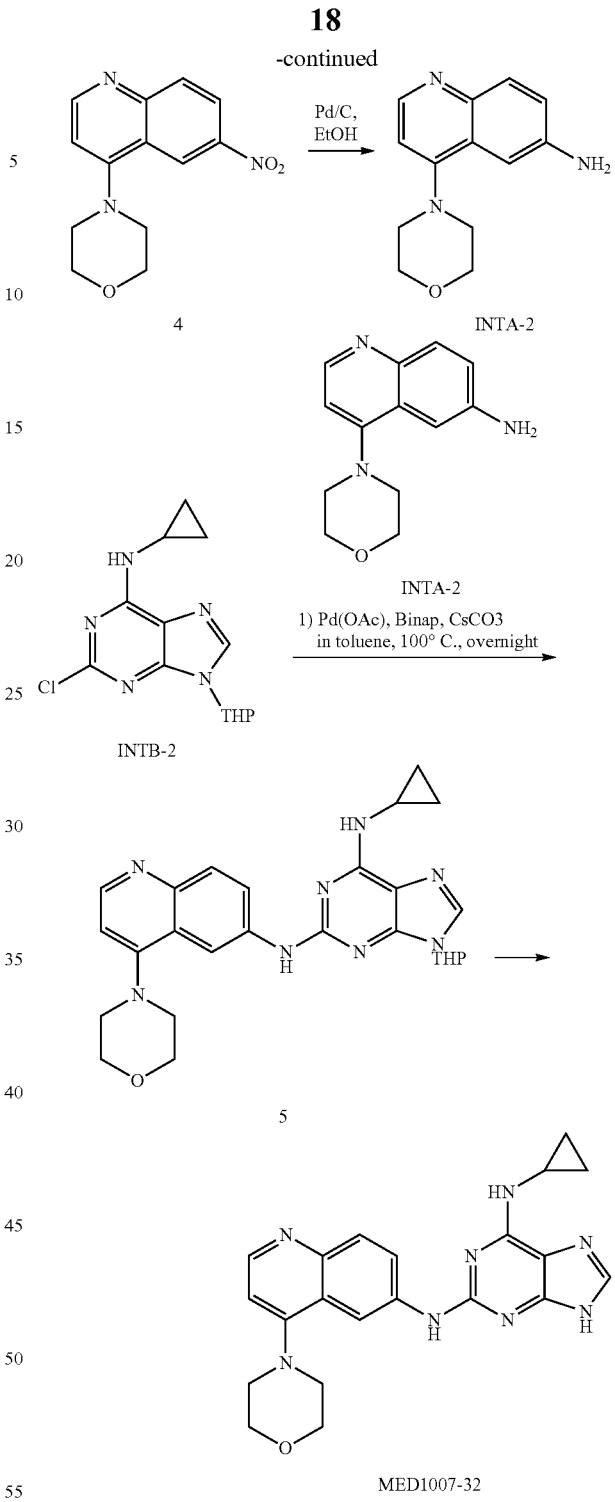

The preparation method of the compound of the example includes the following steps:

1) Compound C (208 mg, 1.0 mmol), palladium acetate (22.45 mg, 0.1 mmol), Binap (125 mg, 0.2 mmol) and cesium carbonate (290 mg, 1.5 mmol) are mixed in a three-necked flask to form a mixture, Compound SM-4 (morpholine, 104 μl, 1.2 mmol) and toluene (3 ml) are added into the mixture in turn under vacuum condition, and is reacted for 3 hours at temperature of 100° C. to form a reaction mixture; then the reaction mixture is cooled, ethyl acetate is added to the reaction mixture, and filtered, and concentrated under reduced pressure, and purified by column chromatography (the eluent of column chromatography is petroleum ether and ethyl acetate (1:3)) to obtain Compound 4 (158 mg).

2) Compound 4 (158 mg, 4.75 mmol) is dissolved in ethanol (8 ml) to form a mixture, palladium/carbon (16 mg) is added into the mixture under vacuum condition, and stirred for 3 hours at room temperature to form a reaction mixture, the reaction mixture is filtered, and concentrated to obtain raw compound INTA-2 of 140 mg.

3) Compound INTAB-2 (144 mg, 0.49 mmol), compound INTA-2 (135 mg, 0.59 mmol), palladium acetate (11 mg, 0.05 mmol), Binap (62 mg, 0.10 mmol) and cesium carbonate (145 mg, 0.75 mmol) are mixed in a three-necked flask to form a mixture, toluene is added into the mixture under vacuum condition; and reacted over night at temperature of 100° C. to form a reaction mixture, and then the reaction mixture is cooled, filtered, purified by thin layer chromatography (a developing solvent of TLC is dichloromethane and methanol (10:1)) to obtain compound 5.

4) Compound 5 is suspend in 1N aqueous hydrochloric acid solution, and stirred for 2 hours at room temperature to form a reaction mixture, the reaction mixture is filtered, and the filter cake is washed with water and dichloromethane to obtain MED1007-32 (105 mg, yield 45%).

Molecular formula: C18H21N7O, Molecular weight: 402.45.

1H-NMR (400 MHz, DMSO-d6): δ 12.388 (s, 1H), 9.271 (s, 1H), 8.492-8.481 (d, J=4.4 Hz, 1H), 8.396 (s, 1H), 8.328 (s, 1H), 7.843-7.824 (d, J=7.6 Hz, 1H), 7.802 (s, 1H), 7.605 (s, 1H), 6.884-6.870 (d, J=5.6 Hz, 1H), 3.915 (s, 4H), 3.169 (s, 4H), 1.229 (s, 1H), 0.760 (m, 2H), 0.669 (m, 2H).

MS (ESI) m/z: 403 [M+1]+

Example 4

Preparation of N6-cyclopropyl-N2-(4-(piperazine-1-yl) quinoline-6-yl)-9H-purine-2, 6-diamine

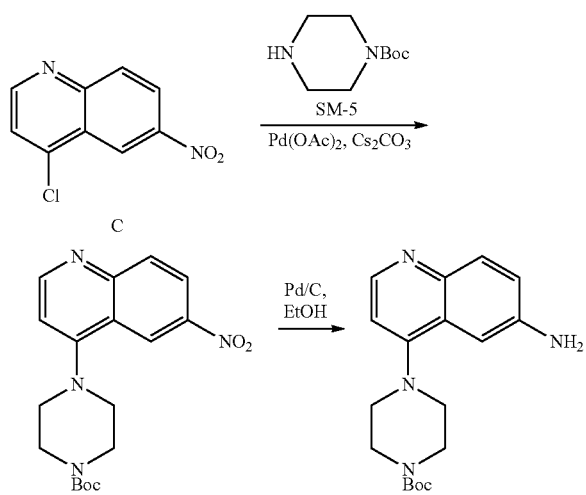

The preparation method of the compound of the example includes the following steps:

1) Compound C (208 mg, 1.0 mmol), palladium acetate (22.45 mg, 0.1 mmol), Binap (125 mg, 0.2 mmol) and cesium carbonate (290 mg, 1.5 mmol) are mixed in a three-necked flask to form a mixture, and Compound SM-5 (104 µl, 1.2 mmol) and toluene (3 ml) are added into the mixture in turn under vacuum condition, and then reacted for 3 hours at temperature of 100° C. to form a reaction mixture, cooled, and ethyl acetate is added into the reaction mixture, and filtrated, the filtrate is concentrated under reduced pressure, and purified by column chromatography (a eluent of column chromatography is petroleum and ethyl acetate (1:3)) to obtain compound 6 (158 mg).

2) Compound 6 (158 mg, 4.75 mmol) is dissolved into ethanol (8 ml) to form a mixture, palladium/carbon (16 mg) is added to the mixture under vacuum condition, and stirred for 3 hours at room temperature to form a reaction mixture. The reaction mixture is filtered, and concentrated to obtain 140 mg of a raw compound 26.

3) Compound 8 (144 mg, 0.49 mmol), compound 26 (135 mg, 0.59 mmol), palladium acetate (11 mg, 0.05 mmol), Binap (62 mg, 0.10 mmol) and cesium carbonate (145 mg, 0.75 mmol) are mixed in a three-necked flask to form a mixture, toluene is added into the mixture under vacuum condition; and reacted over night at temperature of 100° C. to form a reaction mixture; then the reaction mixture is cooled, filtered, the filtrate is purified by thin layer chromatography (a developing solvent of TLC is dichloromethane and methanol (10:1)) to obtain compound 29.

4) Compound 29 is suspend in 4N aqueous hydrochloric acid solution, stirred for 2 hours at room temperature to form a reaction mixture, the reaction mixture is filtered. The filter cake is washed with water and dichloromethane to obtain MED1007-33 (105 mg, yield 45%).

Molecular formula: $C_{18}H_{23}N_9$; Molecular weight: 401.47.

$^1$H-NMR (400 MHz, DMSO-d6): δ 12.404 (s, 1H), 9.266 (s, 1H), 8.461 (s, 1H), 8.384 (s, 1H), 8.284 (s, 1H), 7.821-7.802 (d, J=7.6 Hz, 1H), 7.781 (s, 1H), 7.602 (s, 1H), 6.838 (s, 1H), 3.090 (s, 4H), 3.017 (s, 4H), 1.228 (s, 1H), 1.160 (s, 1H), 0.748 (m, 2H), 0.658 (m, 2H).

MS (ESI) m/z: 402 [M+1]$^+$

Example 5

Preparation of N-(6-isopropoxy-9H-purine-2-yl)quinoline-6-amine

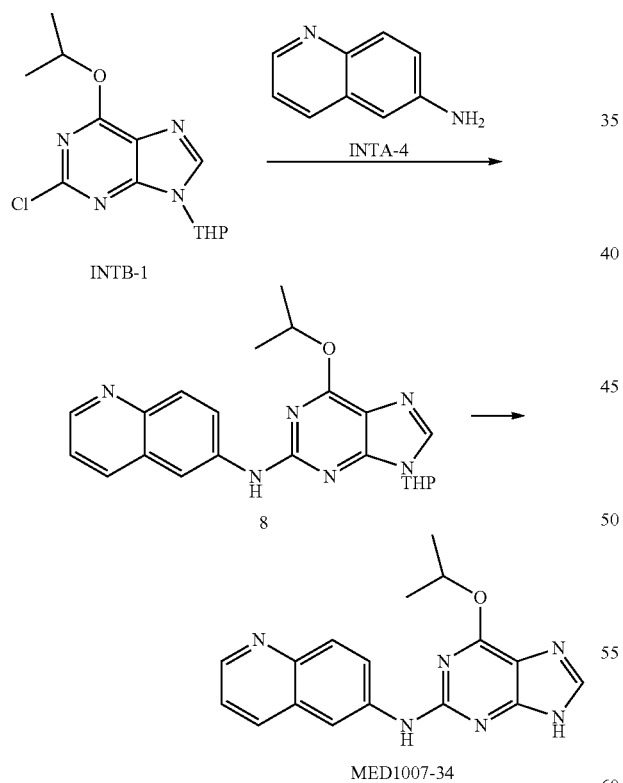

The preparation method of the compound of the example includes the following steps:

1) Compound INTB-1 (144 mg, 0.49 mmol), compound INTA-4 (135 mg, 0.59 mmol), palladium acetate (11 mg, 0.05 mmol), Binap (62 mg, 0.10 mmol) and cesium carbonate (145 mg, 0.75 mmol) are mixed in a three-necked flask to form a mixture, toluene is added into the mixture under vacuum condition; and reacted over night at temperature of 100° C. to form a reaction mixture, the reaction mixture is cooled, filtered, and the filtrate is purified by thin layer chromatography (a developing solvent of TLC is dichloromethane and methanol (10:1)), to obtain compound 8.

2) Compound 8 is suspend in 4N aqueous hydrochloric acid solution, and stirred for 2 hours at room temperature to form a reaction mixture, the reaction mixture is filtered, and the filter cake is washed with water and dichloromethane to obtain MED1007-34 (68 mg, yield 45%).

Molecular formula: $C_{17}H_{16}N_6O$; Molecular weight: 320.35.

$^1$H-NMR (400 MHz, DMSO-d6): δ 12.919 (s, 1H), 9.702 (s, 1H), 8.699 (s, 1H), 8.571 (s, 1H), 8.140 (s, 1H), 8.057 (s, 1H), 7.982 (s, 1H), 7.921 (s, 1H), 7.442 (s, 1H), 5.638 (s, 1H), 1.461 (s, 6H).

MS (ESI) m/z: 321 [M+1]$^+$

Example 6

Preparation of N-(6-cyclopentyloxy-9H-purine-2-yl)quinoline-6-amine

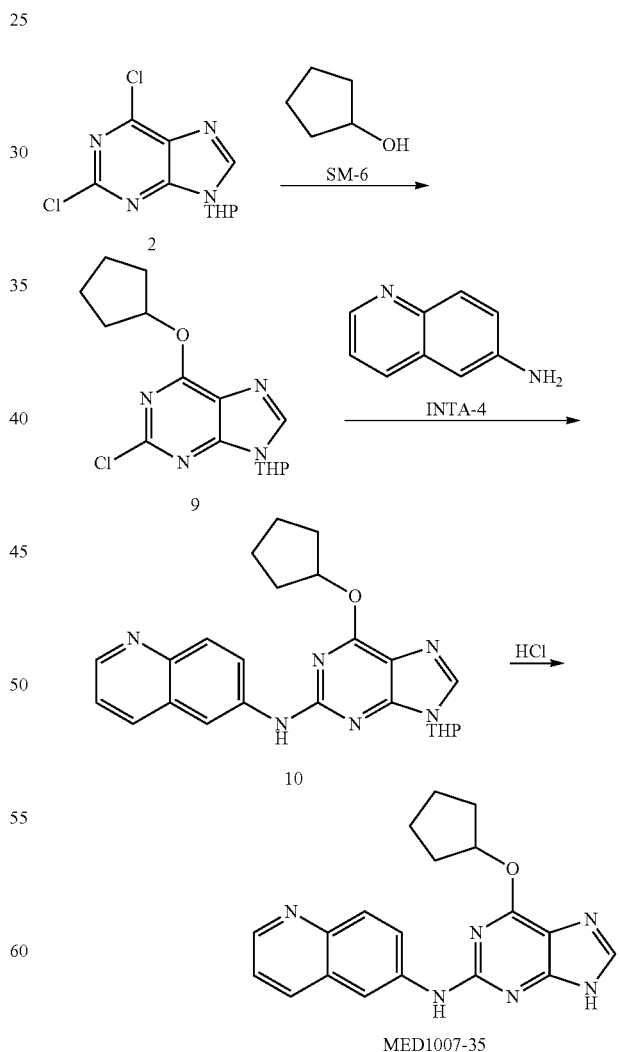

The preparation method of the compound of the example includes the following steps:

1) Sodium hydride (60 mg, 1.5 mmol) is added into DMF (5 ml) and compound SM-6 (86 mg, 1 mmol) and stirred 1 hour at room temperature to form a mixture, and then compound 2 (273 mg, 1 mmol) is added to the mixture at room temperature to form a reaction mixture, and stirred over night; and dissolved in ethyl acetate (50 ml), washed with brine (2×50 ml), dried with anhydrous sodium sulfate, concentrated under vacuum condition, then purified by SGC (ethyl acetate:petroleum ether=1:1) to obtain compound 9 (300 mg, yield 86%).

2) The suspension liquid of compound 9 (160 mg, 0.5 mmol) is refluxed under nitrogen condition for 12 hours to form a reaction mixture; and then cooled to a room temperature, the reaction mixture is dissolved in ethyl acetate (50 ml), washed with brine (2×50 ml), dried with anhydrous sodium sulfate, concentrated under vacuum condition, and purified by Pre-TLC (ethyl acetate:petroleum ether=1:1) to obtained compound 10 (100 mg, yield 68%).

3) Hydrochloric acid/dioxane (5 ml) is added into dioxane (5 ml) and compound 10 (100 mg) to form a mixture, and stirred for 2 hours at room temperature to form a reaction mixture; the reaction mixture is dissolved in dichloromethane (50 ml), washed with sodium hydroxide (50 ml, 1 N) and brine (2×50 ml), dried with anhydrous sodium sulfate, and concentrated in vacuum condition, and purified by Pre-HPLC (a purification solvent) to obtain MED1007-35 (18 mg).

Molecular formula: $C_{18}H_{17}N_7O$, Molecular weight: 346.39.

$^1$H-NMR (400 MHz, DMSO-d6): δ 12.9 (s, 1H), 9.708 (s, 1H), 8.704-8.695 (d, J=3.6 Hz, 1H), 8.585 (s, 1H), 8.156-8.136 (d, J=8.0 Hz, 1H), 8.058 (s, 1H), 8.010-7.987 (d, J=9.2 Hz, 1H), 7.924-7.901 (d, J=9.2 Hz, 1H), 7.461-7.430 (m, 1H), 5.747 (s, 1H), 2.121-2.088 (t, 2H), 1.893-1.860 (d, J=13.2 Hz, 2H), 1.805-1.778 (t, 2H), 1.686-1.672 (d, J=5.6 Hz, 2H).

MS (ESI) m/z: 347 [M+1]$^+$

Example 7

Preparation of N6-cyclopropyl-N2-(4-methyl quinoline-6-yl)-9H-purine-2, 6-diamine dihydrate di-methanesulfonate

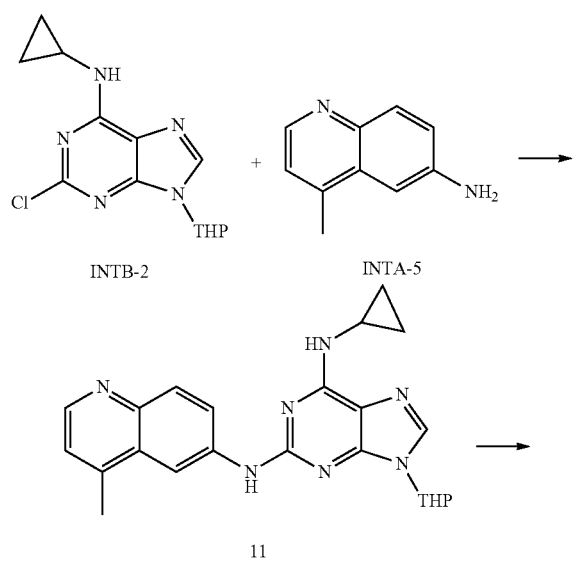

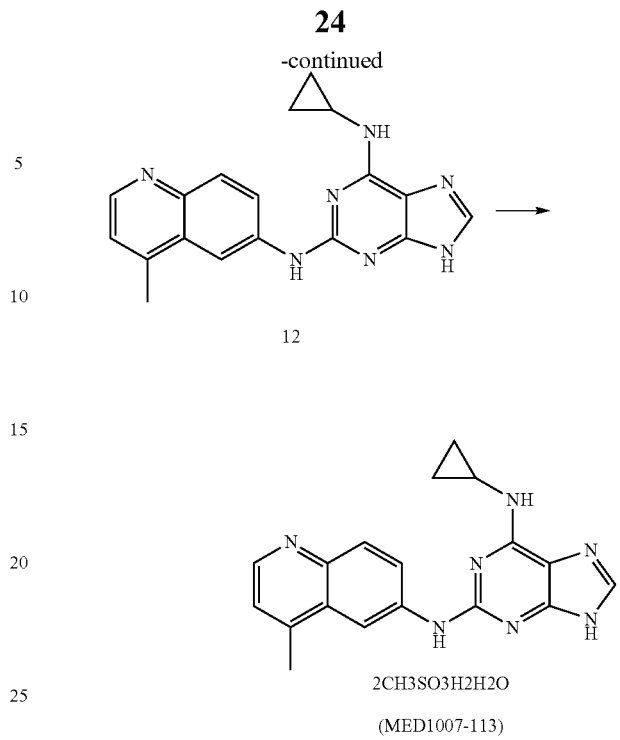

The preparation method of the compound of the example includes the following steps:

1) Compound INTB-2 (450 mg, 1.54 mmol), palladium acetate (68 mg, 0.3 mmol), BINAP (186 mg, 0.3 mmol) and potassium phosphate (1.2 g, 4.62 mmol) are added to compound INTA-5 (243 mg, 1.54 mmol) dissolved in toluene (10 mL), and stirred under reflux overnight to form a reaction mixture, then cooled to a room temperature, ethyl acetate and water are added to the reaction mixture to form an organic layer, then the organic layer is dried with anhydrous sodium sulfate, filtered, concentrated, purified by Pre-TLC (ethyl acetate:methanol=15:1) to obtain compound 11 (250 mg, yield 39%).

2) Compound 11 (250 mg, 0.6 mmol) is dissolved in methanol (5 mL) and 4N hydrochloric acid methanol (5 mL), and stirred overnight at room temperature to form a reaction mixture, the reaction mixture is diluted with water, and extracted by ethyl acetate, washed with sodium bicarbonate and brine, dried with anhydrous sodium sulfate and concentrated to dryness, purified by Pre-TLC (dichloromethane:methanol=10:1) to obtain compound 12 (140 mg, yield 70%).

3) Methanesulfonic acid (152 mg, 1.69 mmol) is added to compound 12 (140 mg, 0.42 mmol) dissolved in aqueous ethanol (5 mL) at temperature of 0° C., and stirred overnight at room temperature to form a reaction mixture. The reaction mixture is filtered, and the filter cake is dried under vacuum condition to obtain compound MED1007-113 (100 mg, yield 42%).

Molecular formula: $C_{18}H_{17}N_7 \cdot 2CH_3SO_3H \cdot 2H_2O$, Molecular weight: 331.37.

$^1$H-NMR (400 MHz, DMSO-d6): δ 10.164 (s, 1H), 8.975 (m, 1H), 8.961 (s, 1H), 8.469 (m, 1H), 8.282 (s, 1H), 8.123 (d, J=9.2 Hz, 1H), 7.914 (d, J=5.6 Hz, 1H), 3.168 (b, 1H), 2.902 (s, 3H), 2.499 (s, 6H), 0.871 (m, 2H), 0.719 (m, 2H).

MS (ESI) m/z: 332.4 [M+1]$^+$.

Example 8

Preparation of N6-cyclopropyl-N2-(4-ethyl quinoline-6-yl)-9H-purine-2,6 diamine dihydrate di-methanesulfonate

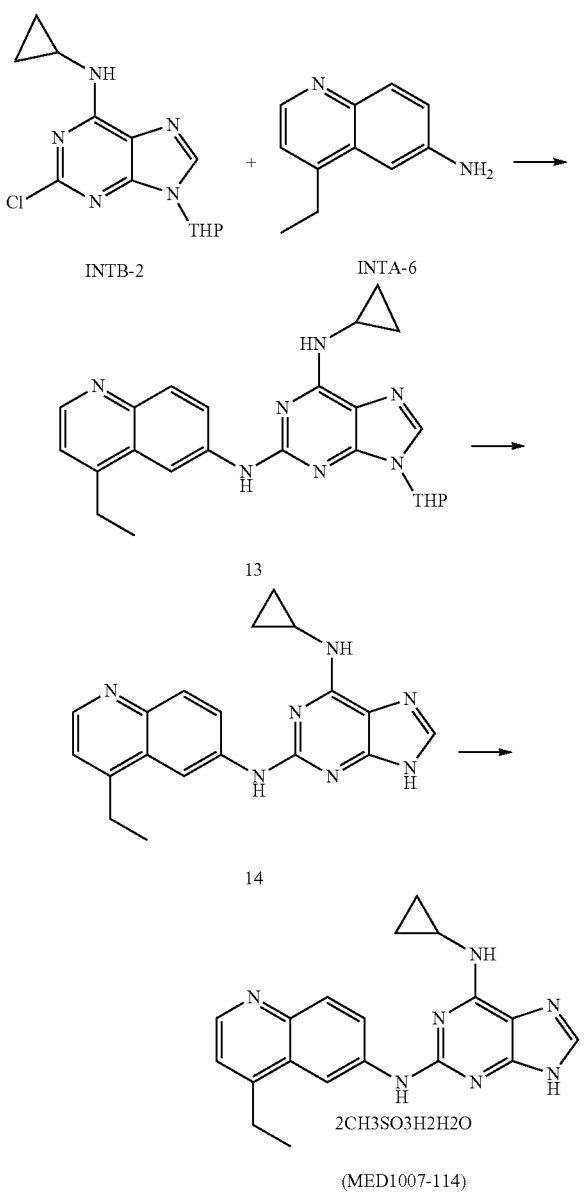

The preparation method of the compound of the example includes the following steps:

1) Compound INTB-2 (136 mg, 0.46 mmol), palladium acetate (20 mg, 0.1 mmol), BINAP (56 mg, 0.1 mmol) and potassium phosphate (368 mg, 1.4 mmol) are added to compound INTA-6 (80 mg, 0.46 mmol) dissolved in toluene (10 mL), and stirred under reflux overnight to form a reaction mixture, then cooled to a room temperature, ethyl acetate and water are added to the reaction mixture to form an, organic layer and the organic layer is separated and dried by anhydrous sodium sulfate, filtered, concentrated and purified by Pre-TLC (ethyl acetate:methanol=15:1) to obtain compound 3 (140 mg, yield: 71%).

2) Compound 13 (140 mg, 0.32 mmol) is dissolved in methanol (5 mL) and 4N hydrochloric acid methanol (5 mL), and stirred overnight at room temperature to form a reaction mixture, the reaction mixture is diluted with water, extracted with ethyl acetate, and washed with sodium bicarbonate and brine, dried over anhydrous sodium sulfate, concentrated to dryness, and purified by Pre-TLC (dichloromethane:methanol=10:1) to obtain compound 14 (60 mg, yield 54%).

3) Compound 4 (60 mg, 0.17 mmol) is dissolved in aqueous ethanol (5 mL), and methanesulfonic acid (52 mg, 0.52 mmol) is added at temperature of 0° C., and stirred overnight at room temperature to form a reaction mixture. The reaction mixture is filtered, the filter cake is dried under vacuum condition to obtain MED1007-114 (25 mg, yield 25%).

Molecular formula: $C_{19}H_{19}N_7 \cdot 2CH_3SO_3H \cdot 2H_2O$, Molecular weight: 345.40.

$^1$H-NMR (400 MHz, DMSO-d6): δ 10.030 (s, 1H), 8.986 (m, 2H), 8.509 (m, 2H), 8.111 (m, 2H), 7.876 (d, J=5.6 Hz, 1H), 3.282 (q, J=7.6 Hz, 2H), 3.158 (m, 1H), 2.338 (s, 6H), 1.415 (t, J=7.6 Hz, 3H), 0.849 (m, 2H), 0.718 (m, 2H).

MS (ESI) m/z: 346.5 [M+1]$^+$.

Example 9

Preparation of N6-cyclopropyl-N2-(4-cyclopropyl quinoline-6-yl)-9H-purine-2, 6-diamine dihydrate di-methanesulfonate

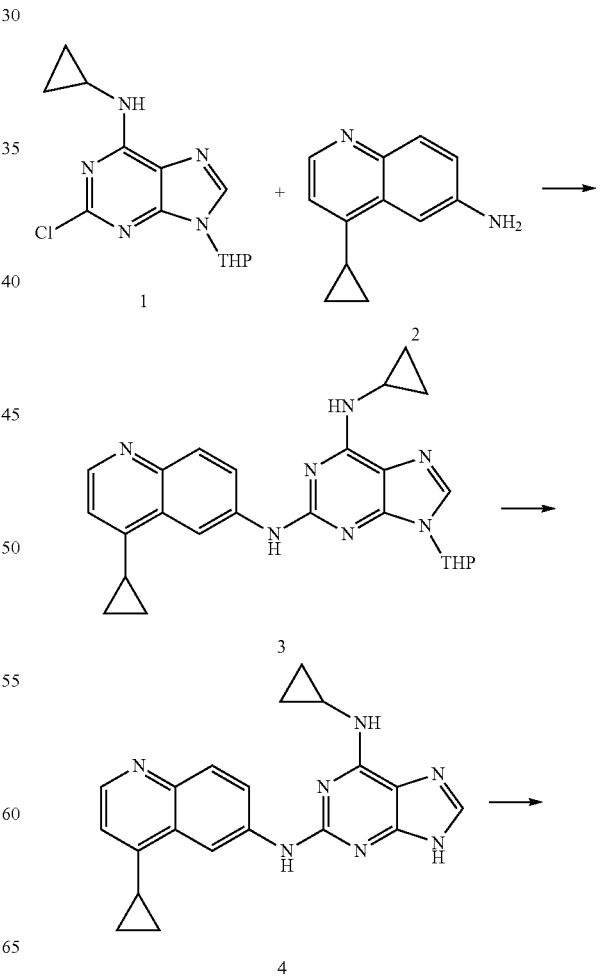

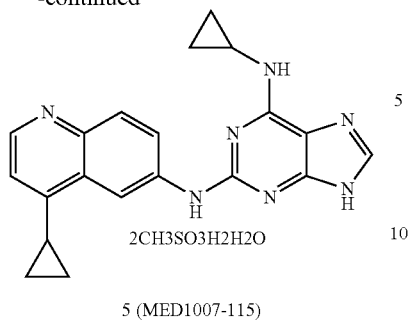

5 (MED1007-115)

The preparation method of the compound of the example includes the following steps:

1) Compound INTB-2 (480 mg, 1.63 mmol), palladium acetate (74 mg, 0.33 mmol), BINAP (205 mg, 0.33 mmol) and potassium phosphate (1280 mg, 4.9 mmol) are added to Compound INTA-7 (300 mg, 1.63 mmol) dissolved in toluene (10 mL), and stirred under reflux overnight, then cooled to a room temperature, ethyl acetate and water are added to the reaction mixture to form an organic layer, the organic layer is separated, dried with anhydrous sodium sulfate, filtered, concentrated and purified by Pre-TLC (ethyl acetate:methanol=15:1) to obtain compound 3 (130 mg, yield: 71%).

2) Compound 15 (130 mg, 0.29 mmol) is dissolved in methanol (5 mL) and 4N hydrochloric acid methanol (5 mL), and stirred overnight at room temperature to form a reaction mixture, and diluted with water, then extracted with ethyl acetate, and washed with sodium bicarbonate and brine, dried over anhydrous sodium sulfate, concentrated to dryness, and purified by Pre-TLC (dichloromethane:methanol=10:1) to obtain compound 16 (60 mg, yield 58%).

3) Methanesulfonic acid (52 mg, 0.52 mmol) is added to Compound 16 (60 mg, 0.17 mmol) dissolved in aqueous ethanol (5 mL) at temperature of 0° C., and stirred overnight at room temperature to form a reaction mixture. The reaction mixture is filtered, the filter cake is dried under vacuum condition to obtain MED1007-115 (30 mg, yield 30%).

Molecular formula: $C_{20}H_{19}N_7 \cdot 2CH_3SO_3H \cdot 2H_2O$, Molecular weight: 357.41.

$^1$H-NMR (400 MHz, DMSO-d6): δ 10.177 (s, 1H), 9.331 (s, 1H), 8.925 (d, J=6 Hz, 1H), 8.767 (m, 1H), 8.493 (m, 1H), 8.308 (br s, 1H), 8.164 (d, J=9.2 Hz, 1H), 7.525 (d, J=6 Hz, 1H), 3.101 (br s, 1H), 2.760 (m, 1H), 2.338 (s, 6H), 1.475 (m, 2H), 1.249 (m, 2H), 0.858 (d, J=6 Hz, 2H), 0.704 (m, 2H).

MS (ESI) m/z: 358.5 [M+1]$^+$.

Example 10

Preparation of 2-(4-(4-methoxy-phenyl) quinoline-6-yl amino)-9H-purine-6-ol-methanesulfonate

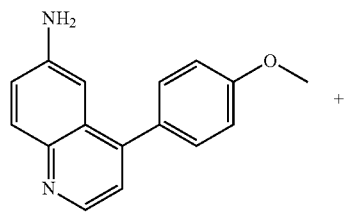

INTA-8

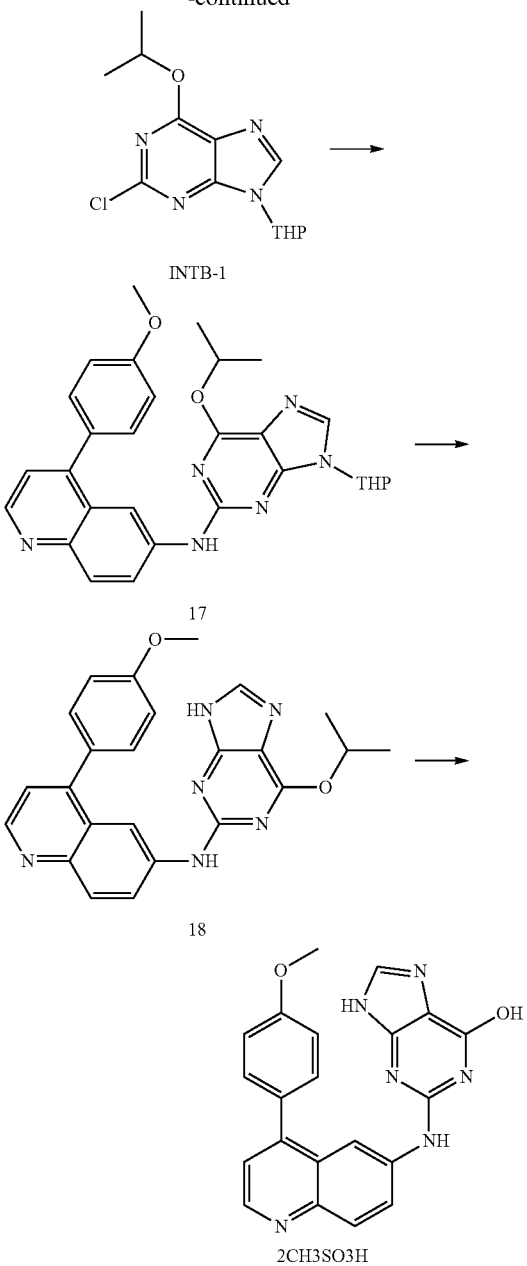

The preparation method of the compound of the example includes the following steps:

1) Compound INTB-1 (33.8 mg, 0.135 mmol), palladium acetate (6 mg, 0.027 mmol), BINAP (16.8 mg, 0.027 mmol) and potassium phosphate (108 mg, 0.41 mmol) are added to compound INTA-8 (40 mg, 0.135 mmol) dissolved in toluene (10 mL), and stirred under reflux overnight to form a reaction mixture, then the reaction mixture is cooled to room temperature, ethyl acetate and water are added to the reaction mixture, form a organic layer, the organic layer is separated, dried over anhydrous sodium sulfate, filtered, concentrated and purified by Pre-TLC (ethyl acetate:methanol=10:1) to obtain compound 17 (60 mg, yield: 88%).

2) Compound 17 (60 mg, 0.12 mmol) is dissolved in methanol (5 mL) and 4N hydrochloric acid methanol (5 mL), and stirred overnight at room temperature to form a reaction mixture, the reaction mixture is diluted with water, and washed with sodium bicarbonate and brine, dried with anhydrous sodium sulfate, concentrated to dryness, and purified by Pre-TLC (dichloromethane:methanol=10:1) to obtain compound 18 (30 mg, yield 58%).

3) Methanesulfonic acid (17 mg, 0.18 mmol) is added to compound 4 (30 mg, 0.07 mmol) dissolved in aqueous ethanol (5 mL) at temperature of 0° C., and stirred overnight at room temperature to form a reaction mixture. The reaction mixture is filtered, the filter cake is dried under vacuum condition to obtain compound 5 (10 mg, yield 38%).

Molecular formula: $C_{21}H_{16}N_6O_2 \cdot 2CH_3SO_3H$, Molecular weight: 497.13.

$^1$H-NMR (400 MHz, DMSO-d6): δ 11.621 (b, 1H), 9.854 (s, 1H), 9.133 (d, J=5.2 Hz, 1H), 8.821 (s, 1H), 8.338 (m, 3H), 7.855 (d, J=5.2 Hz, 1H), 7.728 (d, J=4.4 Hz, 2H), 7.284 (d, J=8.8 Hz, 2H), 3.893 (s, 3H), 2.369 (s, 6H).

MS (ESI) m/z: 385.3 [M+1]$^+$.

Example 11

Preparation of 4-(benzo[1,3]-dioxole-5-yl)-N-(6-isopropoxy-9H-purine-2-yl) quinoline-6-amine-methanesulfonate

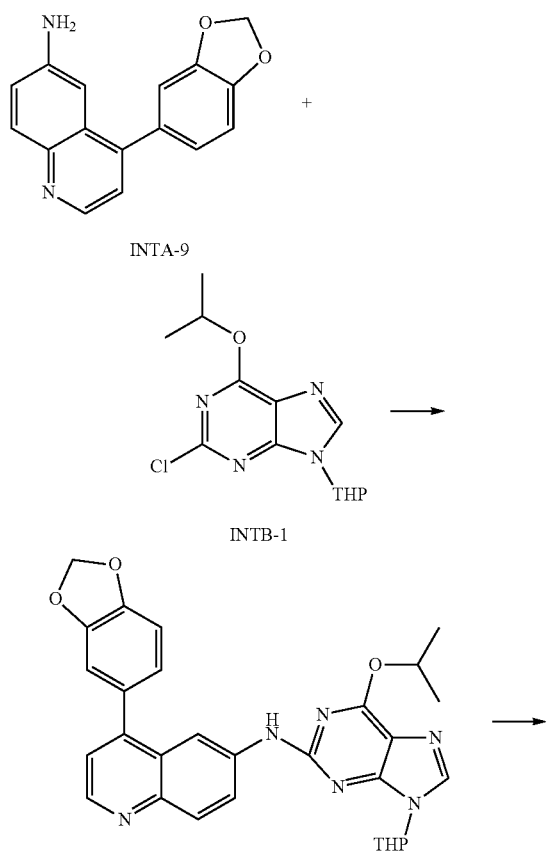

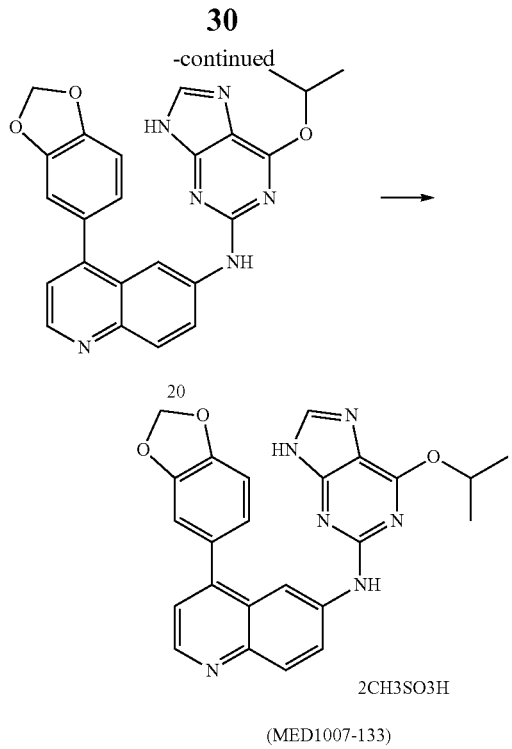

(MED1007-133)

The preparation method of the compound of the present example includes the following steps:

1) Compound INTB-1 (100 mg, 0.38 mmol), palladium acetate (17 mg, 0.076 mmol), BINAP (47 mg, 0.076 mmol) and potassium phosphate (300 mg, 1.14 mmol) are added to compound INTA-9 (150 mg, 0.5 mmol) dissolved in toluene (10 mL) and stirred under reflux overnight to form a reaction mixture, cooled to the room temperature, ethyl acetate and water are added to the reaction mixture to form an organic layer, the organic layer is separated, dried with anhydrous sodium sulfate, filtered, concentrated and purified by Pre-TLC (ethyl acetate:methanol=10:1) to obtain compound 19 (100 mg, yield 50%).

2) Compound 19 (100 mg, 0.19 mmol) is dissolved in methanol (5 mL) and 4N hydrochloric acid methanol (5 mL), and stirred overnight at room temperature to form a reaction mixture, the reaction mixture is diluted with water, and washed with sodium bicarbonate and brine, dried with anhydrous sodium sulfate, concentrated to dryness, and purified by Pre-TLC (dichloromethane:methanol=10:1) to obtain compound 20 (30 mg, yield 36%).

3) Methanesulfonic acid (19 mg, 0.18 mmol) is added to compound 20 (30 mg, 0.07 mmol) dissolved in aqueous ethanol (5 mL) at temperature of 0° C., and stirred overnight at room temperature to form a reaction mixture. The reaction mixture is filtered, the filter cake is dried under vacuum condition to obtain compound MED1007-133 (15 mg, yield 40%).

Molecular formula: $C_{24}H_{20}N_6O_3 \cdot 2CH_3SO_3H$, Molecular weight: 553.45.

$^1$H-NMR (400 MHz, CD3OD): δ 9.173 (s, 1H), 8.869 (d, J=5.6 Hz, 1H), 8.710 (s, 1H), 8.503 (d, J=9.2 Hz, 1H), 8.171 (m, 1H), 7.832 (d, J=5.6 Hz, 1H), 7.210 (d, J=6 Hz, 2H), 7.055 (d, J=8 Hz, 1H), 6.047 (d, J=6 Hz, 2H), 5.250 (s, 1H), 2.613 (s, 6H), 1.320 (m, 6H).

MS (ESI) m/z: 441.4 [M+1]$^+$.

Example 12

Preparation of 2-(4-(3-methoxy-phenyl) quinoline-6-yl-amino)-9H-purine-6-ol-methanesulfonate

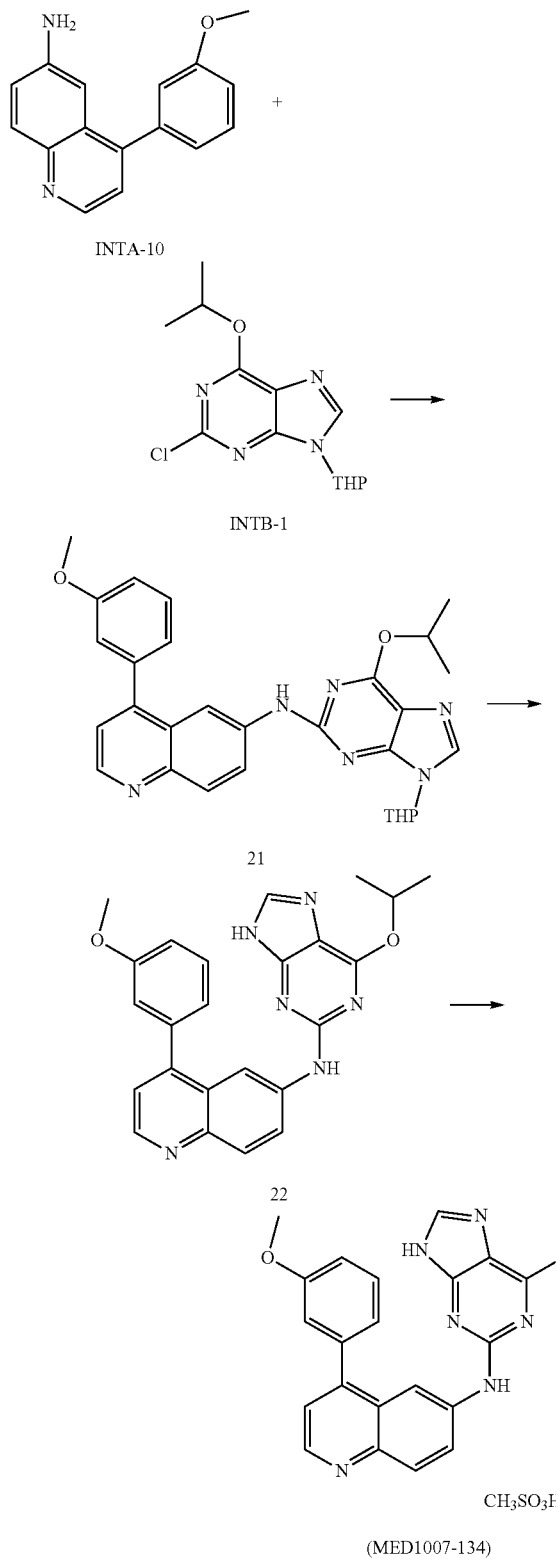

The preparation method of the compound of the example includes the following steps:

1) Compound INTA-10 (170 mg, 0.68 mmol), palladium acetate (31 mg, 0.14 mmol), BINAP (87 mg, 0.14 mmol) and potassium phosphate (540 mg, 2.04 mmol) are added to compound INTB-1 (200 mg, 0.68 mmol) dissolved in toluene (20 mL), and stirred under reflux overnight, cooled to room temperature, ethyl acetate and water are added to the reaction mixture to form an organic layer, the organic layer is separated, dried with anhydrous sodium sulfate, filtered, concentrated and purified by Pre-TLC (ethyl acetate:methanol=10:1) to obtain compound 21 (300 mg, yield 87%).

2) Compound 21 (300 mg, 0.59 mmol) is dissolved in methanol (5 mL) and 4N hydrochloric acid methanol (5 mL), and stirred overnight at room temperature to form a reaction mixture, the reaction mixture is diluted with water, and washed with sodium bicarbonate and brine, dried with anhydrous sodium sulfate, concentrated to dryness, and purified by Pre-TLC (dichloromethane:methanol=10:1) to obtain compound 22 (170 mg, yield 68%).

3) Methanesulfonic acid (19 mg, 0.18 mmol) is added to compound 22 (170 mg, 0.4 mmol) dissolved in aqueous ethanol (10 mL) at temperature of 0° C., and stirred overnight at room temperature to form a reaction mixture. The reaction mixture is filtered, the filter cake is dried under vacuum condition to obtain compound MED1007-134 (50 mg, yield 25%).

Molecular formula: $C_{21}H_{16}N_6O_2 \cdot CH_3SO_3H$, Molecular weight: 480.50.

$^1$H-NMR (400 MHz, DMSO-d6): δ 11.405 (b, 1H), 9.707 (s, 1H), 9.067 (d, J=2.4 Hz, 1H), 8.654 (s, 1H), 8.370 (m, 1H), 8.244 (d, J=8.8 Hz, 1H), 8.151 (d, J=1.6 Hz, 1H), 7.787 (d, J=5.2 Hz, 1H), 7.589 (t, J=8.8 Hz, 1H), 7.250 (d, J=7.6 Hz, 1H), 7.202 (s, 1H), 7.193 (d, J=7.2 Hz, 1H), 3.857 (s, 3H), 2.385 (s, 3H).

MS (ESI) m/z: 385.3 [M+1]$^+$.

Example 13

Preparation of 4-(3-fluorophenyl)-N-(6-isopropoxy-9H-purine-2-yl) quinoline-6-amine-methanesulfonate

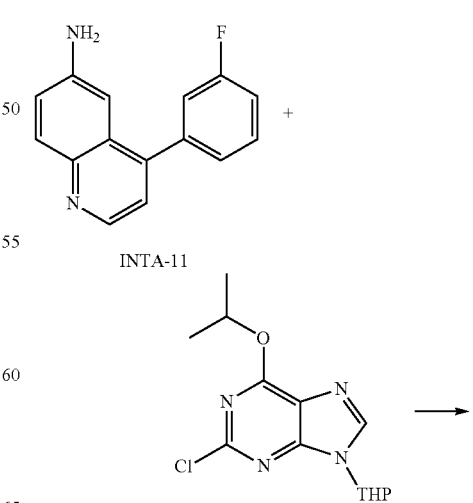

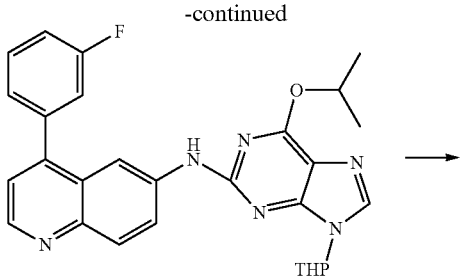

23

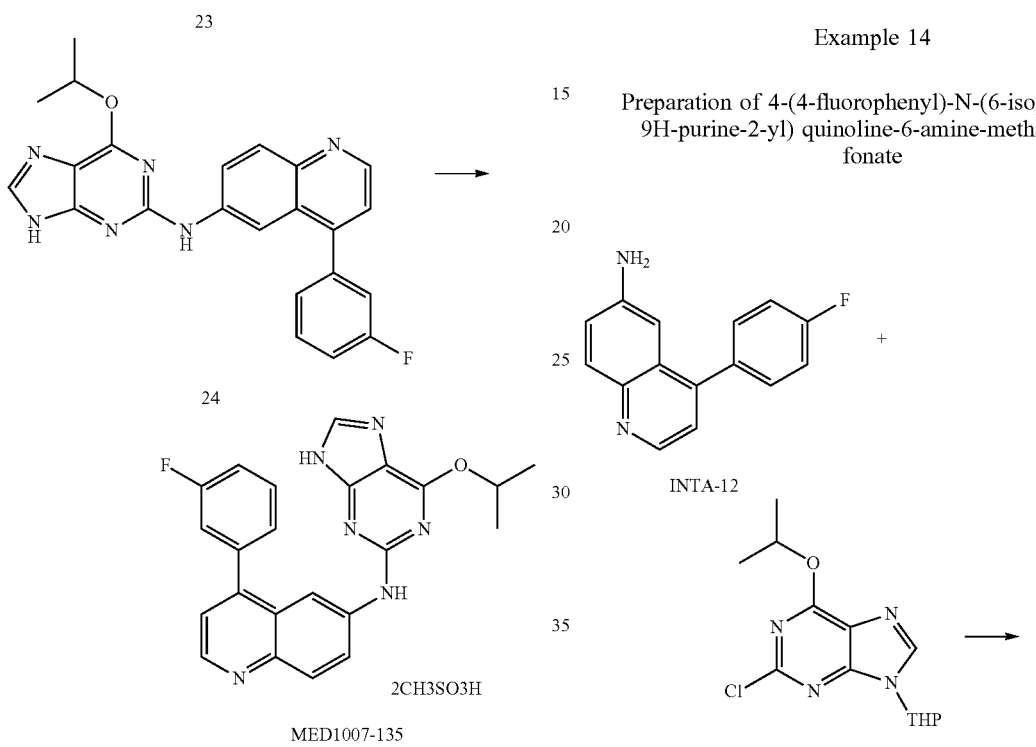

24

MED1007-135

The preparation method of the compound of the example includes the following steps:

1) Compound INTA-11 (100 mg, 0.38 mmol), palladium acetate (17 mg, 0.076 mmol), BINAP (47 mg, 0.076 mmol) and potassium phosphate (300 mg, 1.14 mmol) are added to compound INTB-1 (150 mg, 0.5 mmol) dissolved in toluene (10 mL), and stirred under reflux overnight form a reaction mixture, cooled to room temperature, ethyl acetate and water are added to the reaction mixture to form an, organic layer and the organic layer is separated, dried over anhydrous sodium sulfate, filtered, concentrated and purified by Pre-TLC (ethyl acetate:methanol=10:1) to obtain compound 23 (100 mg, yield 50%).

2) Compound 23 (100 mg, 0.19 mmol) is dissolved in methanol (5 mL) and 4N hydrochloric acid methanol (5 mL), and stirred overnight at room temperature form a reaction mixture, the reaction mixture is diluted with water, and washed with sodium bicarbonate and brine, dried over anhydrous sodium sulfate, concentrated to dryness, and purified by Pre-TLC (dichloromethane:methanol=10:1) to obtain compound 24 (30 mg, yield 36%).

3) Methanesulfonic acid (19 mg, 0.18 mmol) is added to Compound 24 (30 mg, 0.07 mmol) dissolved in aqueous ethanol (5 mL) at temperature of 0° C., and stirred overnight at room temperature form a reaction mixture. The reaction mixture is filtered, the filter cake is dried under vacuum condition to obtain compound MED1007-135 (15 mg, yield 40%).

Molecular formula: $C_{23}H_{19}FN_6O \cdot 2CH_3SO_3H$; Molecular weight: 414.43.

$^1$H-NMR (400 MHz, CD3OD): δ 9.98 (s, 1H), 8.75 (d, J=5.6 Hz, 1H), 8.55-8.60 (m, 2H), 8.23 (d, J=9.2 Hz, 1H), 7.83-7.93 (m, 3H), 7.47-7.51 (m, 2H), 5.30 (m, 1H), 1.390 (m, 6H).

MS (ESI) m/z: 415 [M+1]$^+$.

Example 14

Preparation of 4-(4-fluorophenyl)-N-(6-isopropoxy-9H-purine-2-yl) quinoline-6-amine-methanesulfonate

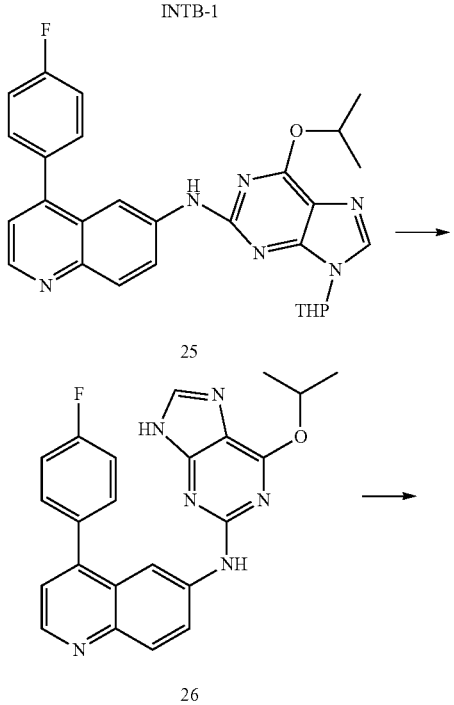

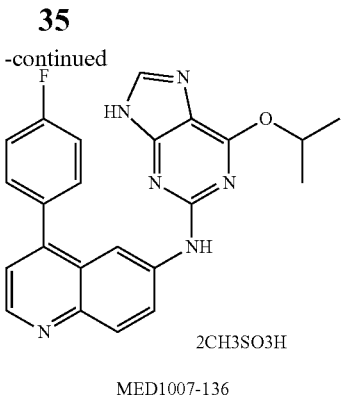

MED1007-136

The preparation method of the compound of the example includes the following steps:

1) Compound INTA-12 (100 mg, 0.38 mmol), palladium acetate (17 mg, 0.076 mmol), BINAP (47 mg, 0.076 mmol) and potassium phosphate (300 mg, 1.14 mmol) are added to compound INTB-1 (150 mg, 0.5 mmol) dissolved in toluene (10 mL) and stirred under reflux overnight to form a reaction mixture, cooled to room temperature, ethyl acetate and water are added to the reaction mixture form an organic layer, and the organic layer is separated, dried over anhydrous sodium sulfate, filtered, concentrated and purified by Pre-TLC (ethyl acetate:methanol=10:1) to obtain compound 25 (100 mg, yield 50%).

2) Compound 25 (100 mg, 0.19 mmol) is dissolved in methanol (5 mL) and 4N hydrochloric acid methanol (5 mL), and stirred overnight at room temperature to form a reaction mixture, the reaction mixture is diluted with water, and washed with sodium bicarbonate and brine, dried over anhydrous sodium sulfate, concentrated to dryness, and purified by Pre-TLC (dichloromethane:methanol=10:1) to obtain compound 26 (30 mg, yield 36%).

3) Methanesulfonic acid (19 mg, 0.18 mmol) is added to compound 26 (30 mg, 0.07 mmol) dissolved in aqueous ethanol (5 mL) at temperature of 0° C., and stirred overnight at room temperature to form a reaction mixture. The to reaction mixture is filtered, the filter cake is dried under vacuum condition to obtain compound MED1007-136 (15 mg, yield 40%).

Molecular formula: $C_{23}H_{19}FN_6O \cdot 2CH_3SO_3H$; Molecular weight: 414.43.

$^1$H-NMR (400 MHz, CD3OD): δ 8.91 (s, 1H), 8.75 (d, J=5.6 Hz, 1H), 8.55-8.60 (m, 2H), 8.14 (d, J=9.2 Hz, 1H), 7.85 (m, 1H), 7.61 (m, 1H), 7.36-7.49 (m, 3H), 5.23 (m, 1H), 1.30 (m, 6H).

MS (ESI) m/z: 415 [M+1]$^+$.

Example 15

Preparation of 4-(3,4-dimethoxy phenyl)-N-(6-isopropoxy-9H-purine-2-yl) quinoline-6-amine-methanesulfonate

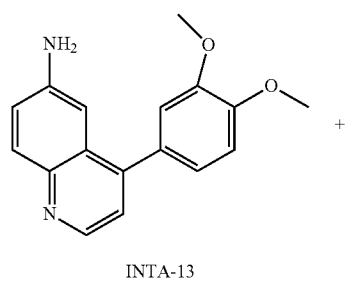

INTA-13

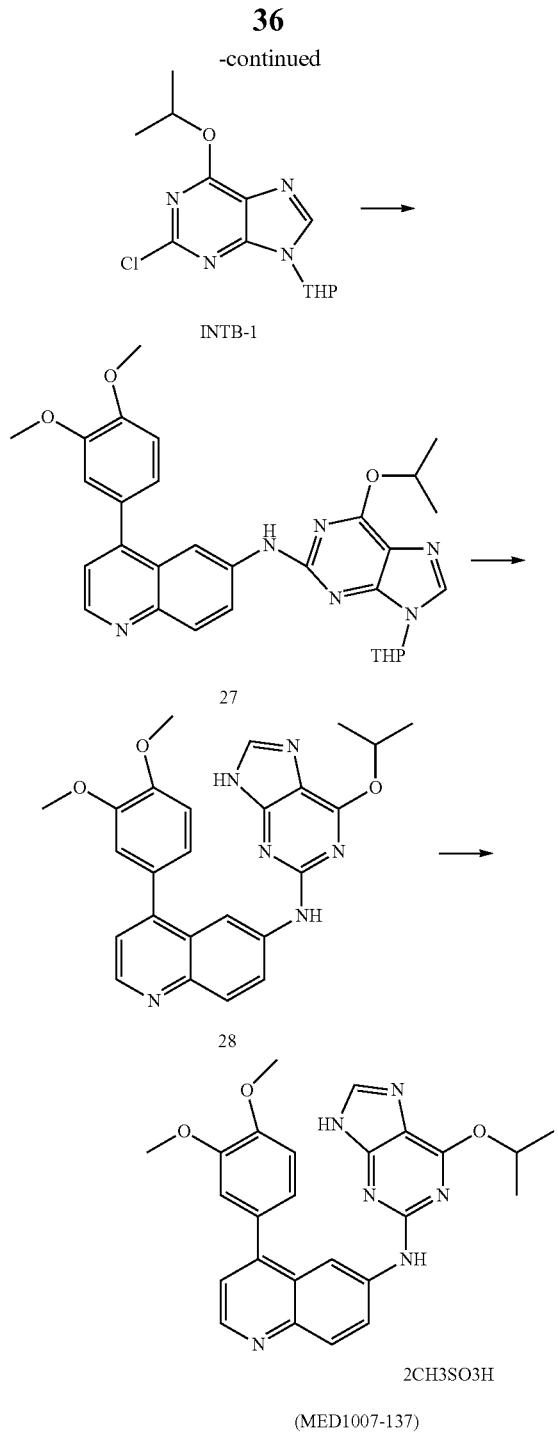

The preparation method of the compound of the example includes the following steps:

1) Compound INTA-13 (160 mg, 0.57 mmol), palladium acetate (25 mg, 0.11 mmol), BINAP (71 mg, 0.11 mmol) and potassium phosphate (451 mg, 1.71 mmol) are added to compound INTB-1 (170 mg, 0.57 mmol) dissolved in toluene (15 mL), and stirred at reflux overnight to form a reaction mixture, cooled to room temperature, ethyl acetate and water are added to the reaction mixture to form an organic layer, and the organic layer is separated, dried over anhydrous sodium sulfate, filtered, concentrated and purified by Pre-TLC (ethyl acetate:methanol=10:1) to obtain compound 27 (150 mg, yield 50%).

2) Compound 27 (150 mg, 0.27 mmol) is dissolved in methanol (5 mL) and 4N hydrochloric acid methanol (5 mL), and stirred overnight at room temperature to form a reaction mixture, the reaction mixture is diluted with water, and washed with sodium bicarbonate and brine, dried with anhydrous sodium sulfate, concentrated to dryness, and purified by Pre-TLC (dichloromethane:methanol=10:1) to obtain compound 28 (40 mg, yield 32%).

3) Methanesulfonic acid (25 mg, 0.26 mmol) is added to compound 28 (40 mg, 0.087 mmol) dissolved in aqueous ethanol (5 mL) at temperature of 0° C., and stirred overnight at room temperature to form a reaction mixture. The reaction mixture is filtered, the filter cake is dried under vacuum condition to obtain compound MED1007-137 (18 mg, yield 37%).

Molecular formula: $C_{25}H_{24}N_6O_3 \cdot 2CH_3SO_3H$; Molecular weight: 569.5.

$^1$H-NMR (400 MHz, CD3OD): δ 9.291 (s, 1H), 9.064 (m, 2H), 8.570 (m, 1H), 8.305 (m, 1H), 7.997 (m, 1H), 7.406 (m, 2H), 7.298 (d, J=8.8 Hz, 1H), 4.916 (s, 1H), 3.950 (m, 6H), 2.731 (s, 6H), 1.377 (m, 6H).

MS (ESI) m/z: 457.5 [M+1]$^+$.

Example 16

Preparation of 2-(4-(benzo[1,3]-dioxole-5-yl) quinoline-6-yl amino)-9H-purine-6-ol-methanesulfonate

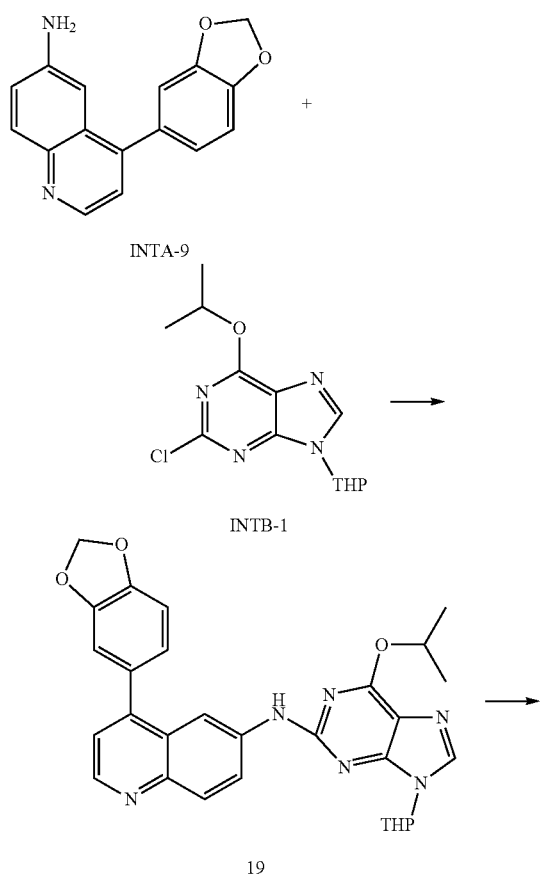

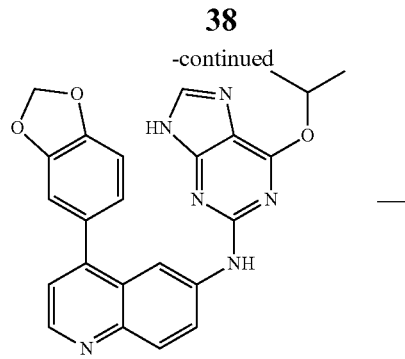

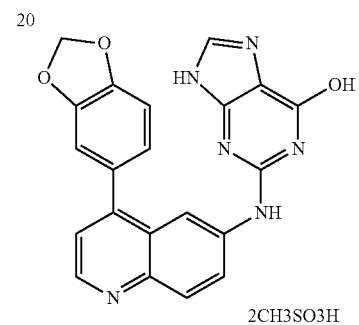

(MED1007-139)

The preparation method of the compound of the example includes the following steps:

1) Compound INTA-9 (35.6 mg, 0.135 mmol), palladium acetate (6 mg, 0.027 mmol), BINAP (16.8 mg, 0.027 mmol) and potassium phosphate (108 mg, 0.41 mmol) are added to compound INTB-1 (40 mg, 0.135 mmol) dissolved in toluene (10 mL), and stirred underreflux overnight to form a reaction mixture, cooled to room temperature, ethyl acetate and water are added to the reaction mixture to form an organic layer, and the organic layer is separated, dried with anhydrous sodium sulfate, filtered, concentrated and purified by Pre-TLC (ethyl acetate:methanol=10:1) to obtain compound 19 (60 mg, yield 85%).

2) Compound 20 (60 mg, 0.11 mmol) is dissolved in methanol (5 mL) and 4N hydrochloric acid methanol (5 mL), and stirred overnight at room temperature to form a reaction mixture, the reaction mixture is dilute with water, and washed with sodium bicarbonate and brine, dried with anhydrous sodium sulfate, concentrated to dryness, and purified by Pre-TLC (dichloromethane:methanol=10:1) to obtain compound 4 (28 mg, yield 58%).

3) Methanesulfonic acid (17 mg, 0.18 mmol) is added to compound 20 (28 mg, 0.07 mmol) dissolved in aqueous ethanol (5 mL) at the temperature of 0° C., and stirred overnight at room temperature to form a reaction mixture. The reaction mixture is filtered, the filter cake is dried under vacuum condition to obtain compound MED1007-139 (11 mg, yield 31%).

Molecular formula: $C_{21}H_{14}N_6O_3 \cdot 2CH_3SO_3H$; Molecular weight: 511.37.

$^1$H-NMR (400 MHz, DMSO-d6): δ 11.758 (b, 1H), 9.974 (s, 1H), 9.151 (d, J=5.2 Hz, 1H), 8.963 (s, 1H), 8.370 (m, 3H), 7.921 (d, J=5.6 Hz, 1H), 7.332 (s, 1H), 7.259 (s, 2H), 6.197 (s, 2H), 2.405 (s, 6H).

MS (ESI) m/z: 399.2 [M+1]$^+$.

Example 17

Preparation of N-(6-isopropoxy-9H-purine-2-yl)-4-(piperazine-1-yl) quinoline-6-amine-methanesulfonate

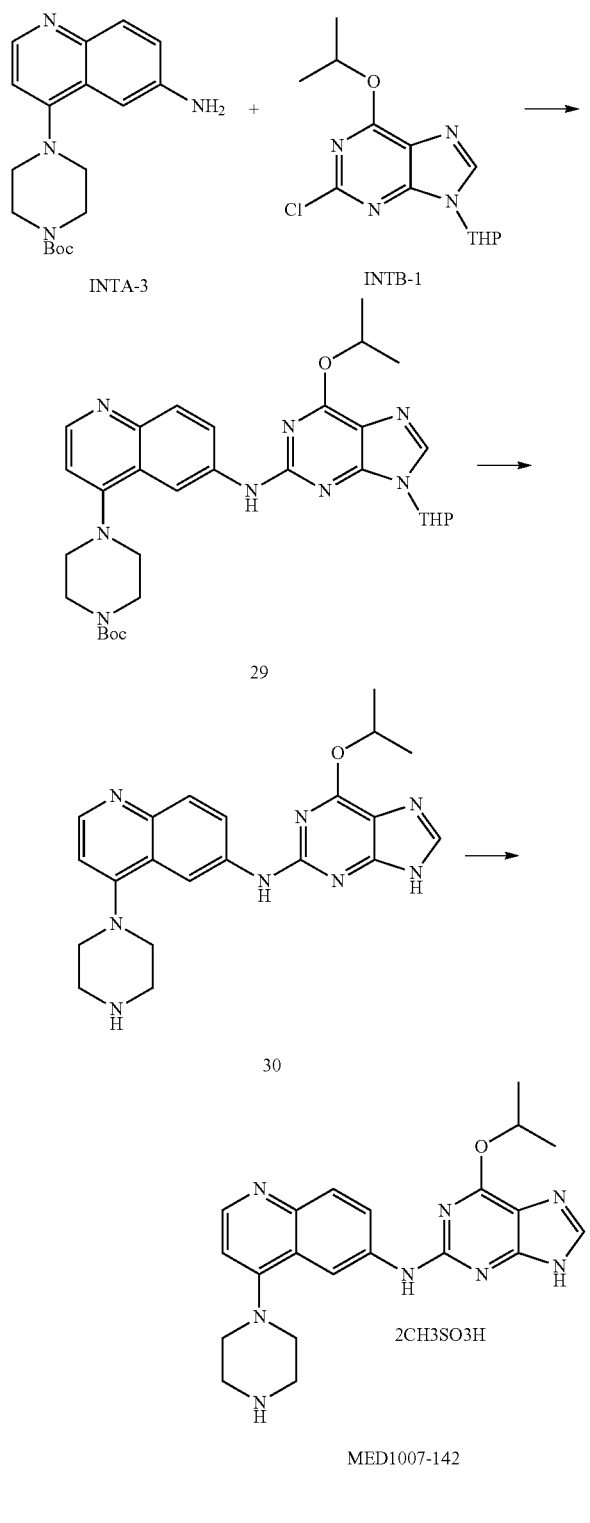

The preparation method of the compound of the example includes the following steps:

1) Compound INTA-3 (183 mg, 0.56 mmol), palladium acetate (25 mg, 0.11 mmol), BINAP (104.5 mg, 0.17 mmol) and potassium phosphate (442 mg, 1.68 mmol) are added to compound INTB-1 (200 mg, 0.68 mmol) dissolved in toluene (10 mL), and stirred at reflux overnight to form a reaction mixture, cooled to room temperature, ethyl acetate and water are added to form an organic layer, and the organic layer is separated, dried with anhydrous sodium sulfate, filtered, concentrated and purified by Pre-TLC (ethyl acetate:methanol=10:1) to obtain compound 29 (223 mg, yield 68%).

2) Compound 29 (190 mg, 0.37 mmol) is dissolved in methanol (5 mL) and 4N hydrochloric acid methanol (5 mL), and stirred overnight at room temperature to form a reaction mixture, the reaction mixture is diluted with water, and washed with sodium bicarbonate and brine, dried with the anhydrous sodium sulfate, concentrated to dryness, and purified by Pre-TLC (dichloromethane:methanol=10:1) to obtain compound 30 (60 mg, yield 40%).

3) Methanesulfonic acid (43 mg, 0.45 mmol) is added to Compound 30 (60 mg, 0.15 mmol) is dissolved in ethanol (5 mL) and water at temperature of 0° C. and stirred overnight at room temperature to form a reaction mixture. The reaction mixture is filtered, the filter cake is dried under vacuum condition to obtain compound MED1007-142 (80 mg, yield 90%).

Molecular formula: $C_{21}H_{24}N_8O \cdot 2CH_3SO_3H$, Molecular weight: 596.68.

$^1$H-NMR (400 MHz, CD$_3$OD): δ 8.9 (s, 1H), 8.469-8.455 (d, J=5.6 Hz, 1H), 7.990 (s, 2H), 7.847-7.824 (d, J=9.2 Hz, 1H), 7.091-7.077 (d, J=5.6 Hz, 1H), 5.586-5.555 (t, 1H), 3.703-3.691 (d, J=4.8 Hz, 4H), 3.603-3.591 (d, J=4.8 Hz, 4H), 1.392 (s, 3H), 1.376 (s, 3H), 1.185 (s, 6H).

MS (ESI) m/z: 405.5 [M+1]$^+$.

Example 18

Preparation of N-(6-isopropoxy-9H-purine-2-yl)-4-(4-methyl piperazine-1-yl) quinoline-6-amine-methanesulfonate

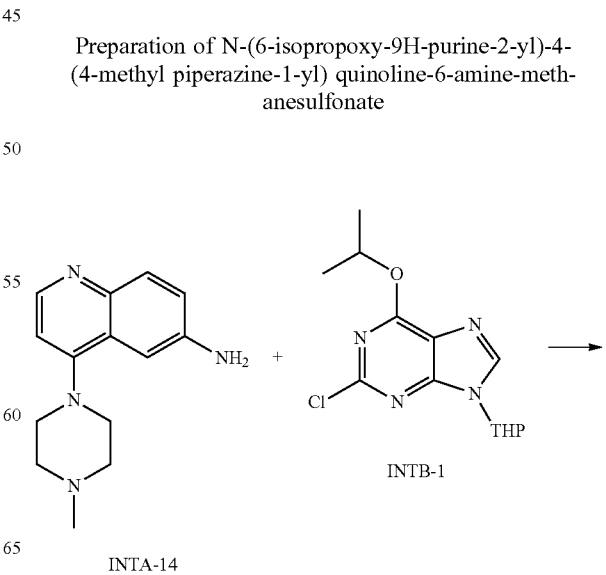

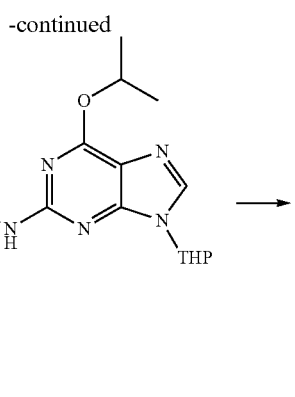

31

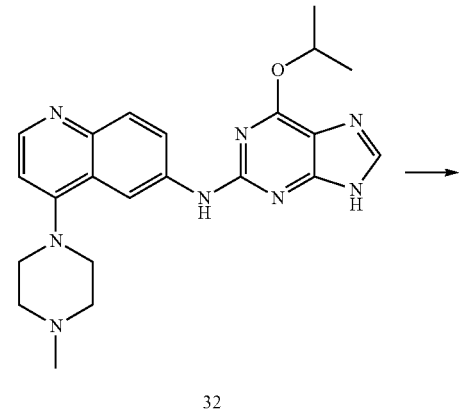

32

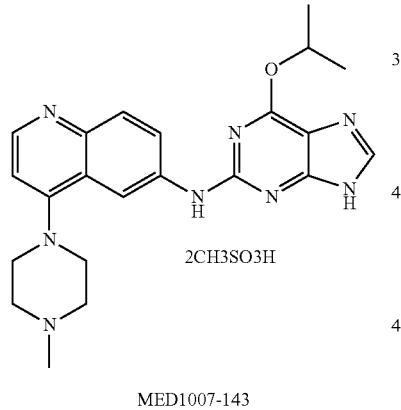

MED1007-143

The preparation method of the compound of the example includes the following steps:

1) Compound INTA-14 (136 mg, 0.56 mmol), palladium acetate (25 mg, 0.11 mmol), BINAP (104.5 mg, 0.17 mmol) and potassium phosphate (442 mg, 1.68 mmol) are added to compound INTB-1 (200 mg, 0.68 mmol) dissolved in toluene (10 mL). and stirred under reflux overnight to form a reaction mixture, cooled to room temperature, ethyl acetate and water are added to the reaction mixture to form an organic layer. Then the organic layer is separated and dried by anhydrous sodium sulfate, and filtered, concentrated and purified by Pre-TLC (ethyl acetate:methanol=10:1) to obtain a brown solid compound 31 (190 mg, yield 67%).

2) Compound 31 (190 mg, 0.37 mmol) is dissolved in methanol (5 mL) and 4N hydrochloric acid methanol (5 mL), and stirred overnight at room temperature to form a reaction mixture, the reaction mixture is diluted with water, extracted with ethyl acetate and washed with sodium bicarbonate and brine to form an organic phase. The organic phase is dried with sodium sulfate, concentrated to dryness, and purified by Pre-TLC (dichloromethane:methanol=10:1) to obtain yellow solid compound 32 (88 mg, yield 57%).

3) Methanesulfonic acid (60 mg, 0.63 mmol) is added to compound 32 (88 mg, 0.21 mmol) dissolved in ethanol (5 mL) and water at temperature of 0° C., and stirred overnight at room temperature to form a reaction mixture. The reaction mixture is filtered, the filter cake is dried under vacuum condition to obtain compound MED1007-143 (20 mg, yield 15%).

Molecular formula: $C_{22}H_{26}N_8O \cdot 2CH_3SO_3H$, Molecular weight: 610.2.

$^1$H-NMR (400 MHz, DMSO-d6): δ 10.203 (s, 1H), 8.777-8.761 (d, J=6.4 Hz, 1H), 8.712 (s, 1H), 8.507 (s, 2H), 8.116-8.093 (d, J=9.2 Hz, 1H), 7.380-7.363 (d, J=6.8 Hz, 1H), 5.641 (s, 1H), 4.283-4.281 (s, 3H), 3.168 (s, 4H), 2.962 (s, 4H), 2.357 (s, 6H), 1.457 (s, 3H), 1.442 (s, 3H).

MS (ESI) m/z: 419.4 [M+1]$^+$.

Example 19

Preparation of 1-(2-(4-phenyl quinoline-6-yl amino)-9H-purine-6-yl) piperidine-4-ol

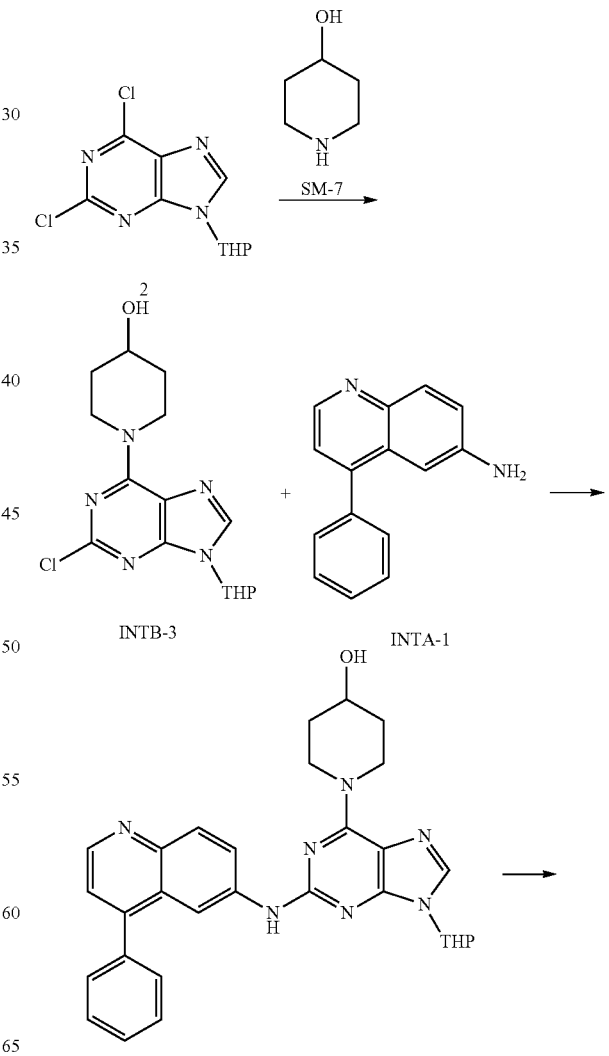

33

43
-continued

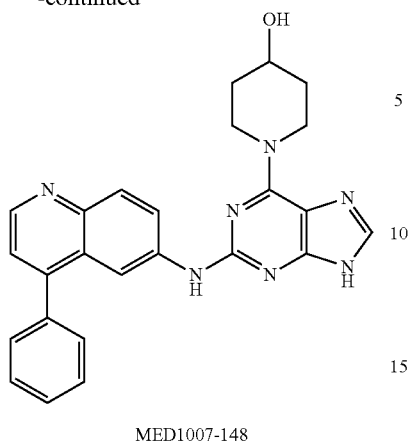

MED1007-148

The preparation method of the compound of the example includes the following steps:

1) Compound 2 (0.3 g, 3.1 mmol), DIPEA (0.7 g, 5.2 mmol) are added to compound 2 (0.7 g, 2.56 mmol) dissolved in tetrahydrofuran (10 ml), and stirred for 10 hours at room temperature to form a reaction mixture. Water is added to dilute the reaction mixture, and extracted with ethyl acetate to form an organic layer. The organic layer is separated and dried with anhydrous sodium sulfate, and filtered, concentrated, purified by SGC to obtain brown solid compound INTB-3 (0.75 g, yield 85%).

2) Compound INTB-3 (750 mg, 2.22 mmol), palladium acetate (100 mg, 0.45 mmol), BINAP (414 mg, 0.67 mmol) and potassium phosphate (1.8 g, 6.67 mmol) are added to compound INTA-1 (540 mg, 2.44 mmol) dissolved in toluene (30 mL), and stirred under reflux overnight to form a reaction mixture, cooled to room temperature, and ethyl acetate and water are added to the reaction mixture to form an organic layer. The organic layer is separated, dried with anhydrous sodium sulfate. And the organic layer is filtered and concentrated, purified by SGC (dichloromethane:methanol=50:1) to obtain brown solid compound 33 (500 mg, yield 50%).

3) Compound 33 (100 mg, 0.19 mmol) is dissolved in methanol (2 mL) and 4N hydrochloric acid methanol (2 mL), and stirred overnight at room temperature to form a reaction mixture. Water is added to the reaction mixture to dilute the reaction mixture, and then extracted with ethyl acetate, and washed by sodium bicarbonate and brine, dried with anhydrous sodium sulfate, concentrated to dryness, purified by SGC (dichloromethane:methanol=10:1) and then yellow solid MED1007-148 (30 mg, yield 38%).

Molecular formula: $C_{25}H_{23}N_7O$, Molecular weight: 437.20.

$^1$H-NMR (400 MHz, DMSO-d6): δ 9.285 (s, 1H), 8.771-8.761 (d, J=4.0 Hz, 1H), 8.312-8.308 (d, J=1.6 Hz, 1H), 8.266-8.243 (d, J=9.2 Hz, 1H), 8.034-8.011 (d, J=9.2 Hz, 1H), 7.881 (s, 1H), 7.657-7.586 (m, 5H), 7.374-7.363 (d, J=4.4 Hz, 1H), 4.758 (s, 2H), 3.742 (s, 1H), 1.785-1.761 (m, 4H), 1.342 (m, 4H).

MS (ESI) m/z: 438.3 [M+1]+

Example 20

Preparation of 1-(2-(4-phenyl quinoline-6-yl amino)-9H-purine-6-yl) piperidine-3-amide

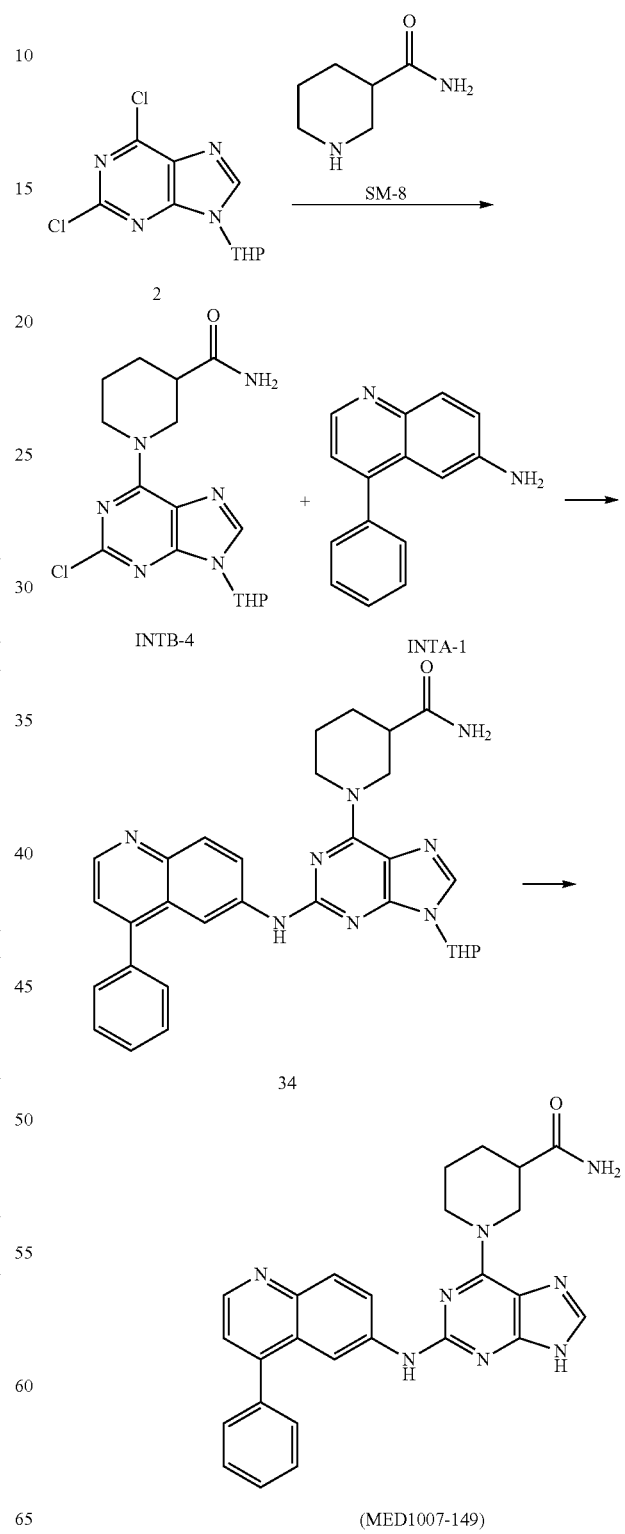

The preparation method of the compound of the example includes the following steps:

1) Compound SM-8 (0.4 g, 3.1 mmol), DIPEA (0.7 g, 5.2 mmol) are added to compound 2 (0.7 g, 2.56 mmol) dissolved in tetrahydrofuran (10 ml), and stirred for 10 hours at room temperature to form a reaction mixture. Water is added to the reaction mixture to dilute the reaction mixture and extracted with ethyl acetate to form an organic layer. The organic layer is separated, dried with anhydrous sodium sulfate, filtrated and concentrated, purified by SGC to obtain brown solid compound INTB-4 (0.8 g, yield 85%).

2) Compound INTB-4 (810 mg, 2.22 mmol), palladium acetate (100 mg, 0.45 mmol), BINAP (414 mg, 0.67 mmol) and potassium phosphate (1.8 g, 6.67 mmol) are added to compound INTA-1 (540 mg, 2.44 mmol) dissolved in toluene (30 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated and concentrated, purified by SGC (dichloromethane:methanol=50:1) to obtain brown solid compound 34 (240 mg, yield 20%).

3) Compound 34 (80 mg, 0.15 mmol) is dissolved in dichloromethane (5 mL) and trifluoroacetic acid (1 mL), and stirred overnight at room temperature to form a reaction mixture, and diluted with water, extracted with ethyl acetate, the and washed with sodium bicarbonate and brine to form an organic phase, the organic phase is dried with anhydrous sodium sulfate, concentrated to dryness, and then purified by SGC (dichloromethane:methanol=10:1) to obtain yellow solid (MED1007-149) (25 mg, yield 40%).

Molecular formula: $C_{26}H_{24}N_8O$, Molecular weight: 464.21.

$^1$H-NMR (400 MHz, DMSO-d6): δ 9.206 (s, 1H), 8.710-8.699 (d, J=4.4 Hz, 1H), 8.314-8.294 (d, J=8.0 Hz, 1H), 8.150 (s, 1H), 7.969-7.946 (d, J=9.2 Hz, 1H), 7.809 (s, 1H), 7.622-7.529 (m, 5H), 7.342 (s, 1H), 7.316-7.305 (d, J=4.4 Hz, 1H), 6.849 (s, 1H), 3.157-3.140 (m, 2H), 2.338-2.311 (m, 2H), 1.883-1.859 (m, 2H), 1.644-1.620 (m, 2H), 1.359-1.335 (m, 2H).

MS (ESI) m/z: 465.4 [M+1]+

Example 21

Preparation of 1-(2-(4-phenyl quinoline-6-yl amino)-9H-purine-6-yl amino)cyclopropane carboxylic acid methyl ester

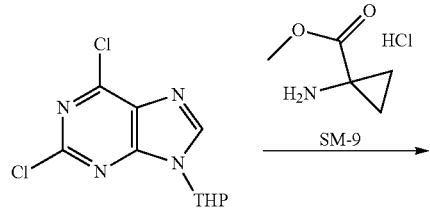

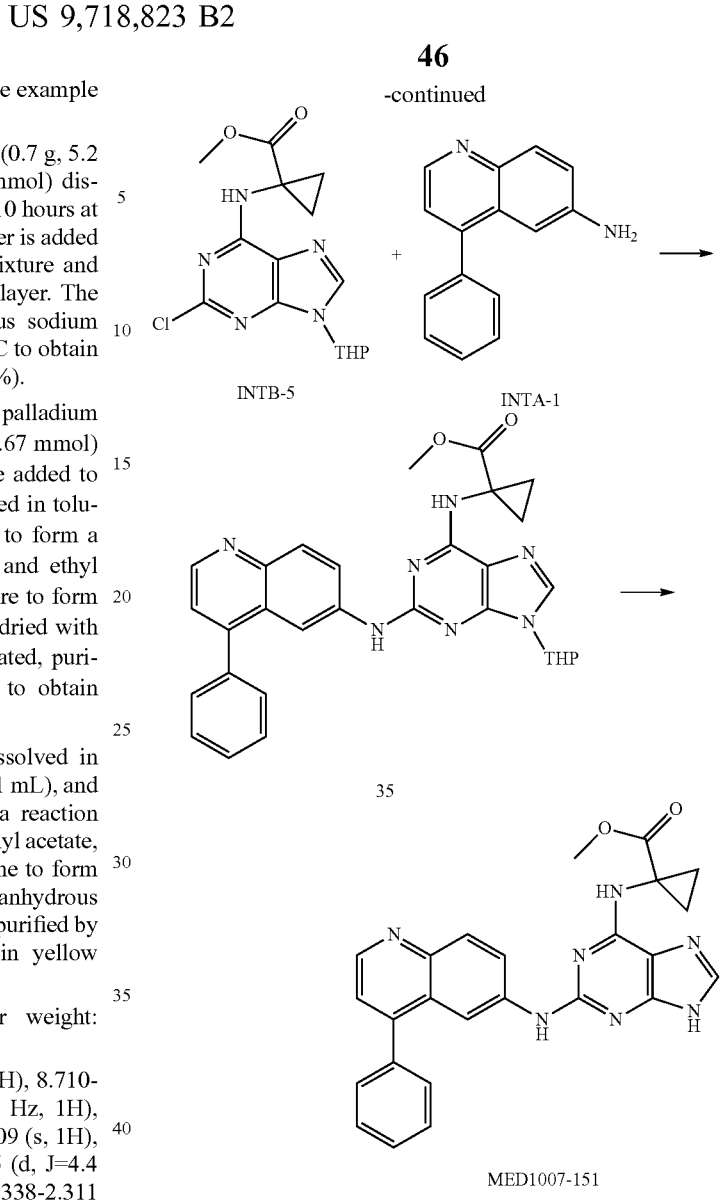

The preparation method of the compound of the example includes the following steps:

1) Compound SM-9 (0.72 g, 4.78 mmol) and DIPEA (2.4 g, 18.4 mmol) are added to compound 2 (1 g, 3.68 mmol) dissolved in dichloromethane (10 ml) and stirred for 50 hours at temperature of 50° C. to form a reaction mixture. Water and ethyl acetate are added to the reaction mixture, and cooled to room temperature to form an organic layer. The organic layer is separated, dried with anhydrous sodium sulfate filtrated, concentrated, and then purified by SGC (ethyl acetate:petroleum ether=1:2) to obtain brown solid compound INTB-5 (0.9 g, yield 75%).

2) Compound INTB-5 (500 mg, 1.4 mmol), palladium acetate (63 mg, 0.28 mmol), BINAP (174 mg, 0.28 mmol) and potassium phosphate (1.1 g, 4.2 mmol) are added to compound INTA-1 (313 mg, 1.4 mmol) dissolved in toluene (30 mL), and stirred under reflux overnight to form a reaction mixture, cooled to room temperature, ethyl acetate and water are added to the reaction mixture to form an organic layer, the organic layer is separated and dried with anhydrous sodium sulfate, filtrated, concentrated, and then purified by SGC (dichloromethane:methanol=30:1) to obtain brown solid compound 35 (535 mg, yield 65%).

3) Compound 35 (535 mg, 1 mmol) is dissolved in methanol (5 mL) and 4N hydrochloric acid methanol (5 mL), and stirred overnight at room temperature to form a reaction mixture, and the reaction mixture is diluted with water, extracted by ethyl acetate and washed by sodium bicarbonate and brine to form an organic phase, the organic phase is dried with anhydrous sodium sulfate and concentrated to dryness, and then purified by SGC (dichloromethane:methanol=10:1) to obtain yellow solid (MED1007-151) (300 mg, yield 65%).

Molecular formula: $C_{25}H_{21}N_7O_2$, Molecular weight: 451.18.

MS (ESI) m/z: 452.1 $[M+1]^+$.

Example 22

Preparation of 1-(2-(4-phenyl quinoline-6-yl amino)-9H-purine-6-yl amino)cyclopropane carboxylic acid

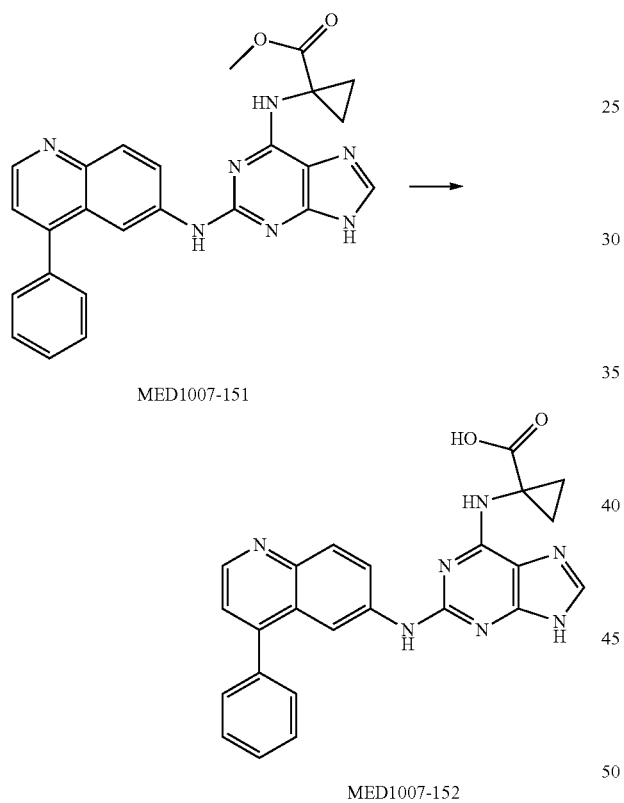

The preparation method of the compound of the example includes the following steps:

Lithium hydroxide (30 mg, 0.72 mmol) is in batches added into tetrahydrofuran (5 mL) and water (0.5 mL) and compound MED1007-151 (65 mg, 0.15 mmol) at temperature of 0° C., and stirred for 50 hours at room temperature to form a reaction mixture, then adjusted to pH=5 with hydrochloric acid, and filtrated and dried to obtain compound MED1007-152 (40 mg, yield 60%).

Molecular formula: $C_{24}H_{19}N_7O_2$, Molecular weight: 437.16.

$^1$H-NMR (400 MHz, DMSO-d6): δ 12.1 (b, 1H), 9.157 (s, 1H), 8.699 (s, 1H), 7.928-7.307 (m, 10H), 1.404 (s, 1H), 1.114 (s, 1H).

MS (ESI) m/z: 438.1 $[M+1]^+$.

Example 23

Preparation of N6-cyclopropyl-N2-(4-phenyl quinoline-6-yl)-9H-purine-2,6 diamine

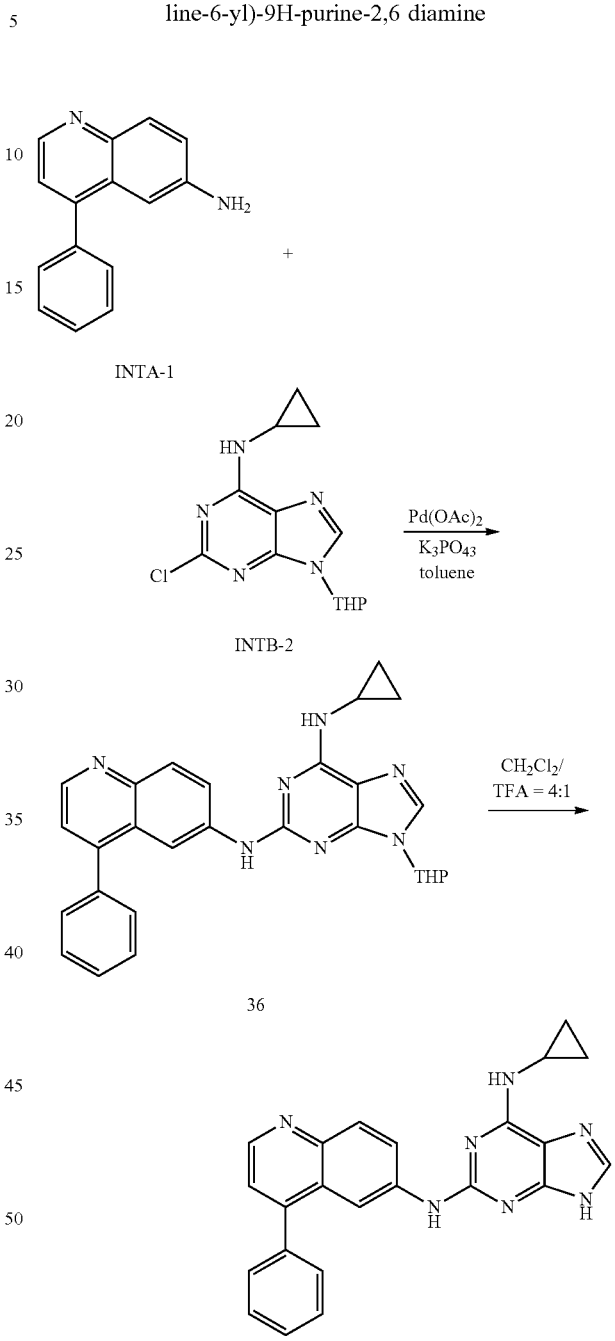

The preparation method of the compound of the example includes the following steps:

1) Compound INTA 1 (60 mg, 0.27 mmol), compound INTB-2 (80 mg, 0.27 mmol), palladium acetate (10 mg, 0.045 mmol), Binap (30 mg, 0.048 mmol) and potassium phosphate (230 mg, 1.08 mmol) are dissolved in toluene (10 mL), and then stirred under reflux overnight to form a reaction mixture, cooled to room temperature, ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 36 (50 mg, yield 39%).

2) Compound 36 (50 mg, 0.104 mmol) is dissolved in dichloromethane (4 mL) and trifluoroacetic acid (2 mL), and stirred overnight at room temperature, concentrated to dryness and purified by Pre-TLC (dichloromethane:methanol=10:1) to obtain then yellow solid compound MED1007-31 (25 mg, yield 61%).

Molecular formula: $C_{23}H_{19}N_7$, Molecular weight: 393.44.

$^1$H-NMR (400 MHz, CD3OD): δ 8.445 (s, 1H), 8.377 (d, J=5.2 Hz, 1H), 7.963 (d, J=8.8 Hz, 1H), 7.875 (s, 1H), 7.761 (d, J=8.8 Hz, 1H), 6.846 (d, J=5.2 Hz, 1H), 5.556-5.586 (m, 1H), 3.193-3.209 (m, 4H), 3.086-3.096 (m, 4H), 1.379 (d, J=6.0 Hz, 6H).

MS (ESI) m/z: 394.3 [M+1]$^+$.

Example 24

Preparation of N-(6-phenoxy-9H-purine-2-yl)-4-(piperazine-1-yl) quinoline-6-amine

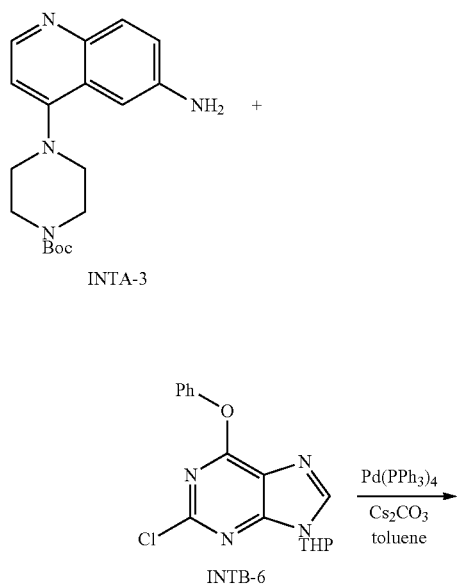

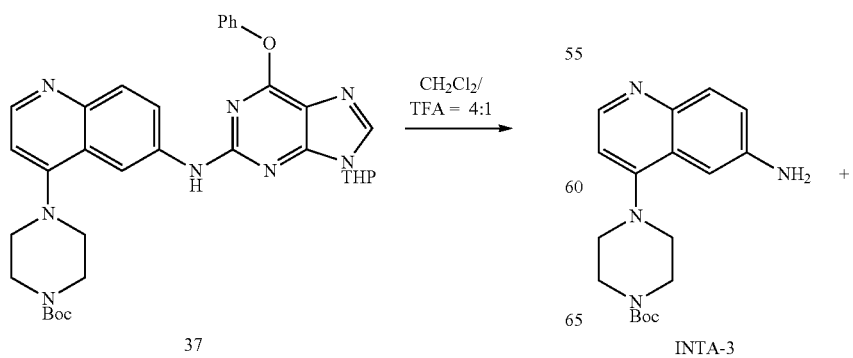

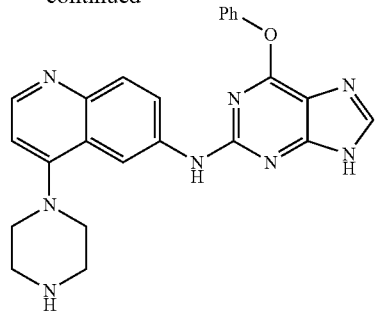

MED1007-54

The preparation method of the compound of the example includes the following steps:

1) Compound INTB-6 (101 mg, 0.305 mmol), Pd(PPh$_3$)$_4$ (35 mg, 0.0305 mmol) and cesium carbonate (198 mg, 0.61 mmol) are added to compound INTA-3 (100 mg, 0.305 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 37 (101 mg, yield 53%).

2) Compound 37 (101 mg, 0.16 mmol) is dissolved in dichloromethane (4 mL) and trifluoroacetic acid (1 mL), and stirred overnight at room temperature to form a reaction mixture, the reaction mixture is concentrated, dried and purified by Pre-TLC to obtain yellow solid compound MED1007-54 (9 mg, yield 11%).

Molecular formula: $C_{24}H_{22}N_8O$, Molecular weight: 438.48.

$^1$H-NMR (400 MHz, CD3OD): δ 8.646 (s, 1H), 8.431-8.472 (m, 2H), 8.012 (d, J=8.8 Hz, 1H), 7.731 (d, J=8.8 Hz, 1H), 7.383-7.421 (m, 2H), 7.181-7.262 (m, 4H), 3.920-3.930 (m, 4H), 3.200-3.215 (m, 4H).

MS (ESI) m/z: 439 [M+1]$^+$

Example 25

Preparation of N-(6-isopropoxy-9H-purine-2-yl)-4-(piperazine-1-yl) quinoline-6-amine

51

-continued

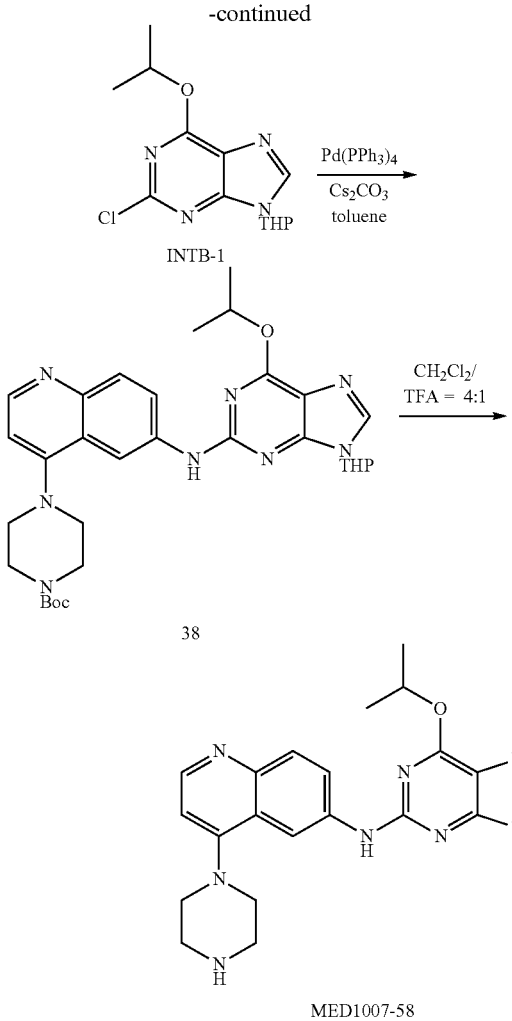

38

MED1007-58

The preparation method of the compound of the example includes the following steps:

1) Compound 2 (90 mg, 0.305 mmol), Pd(PPh$_3$)$_4$ (35 mg, 0.0305 mmol) and cesium carbonate (198 mg, 0.61 mmol) are added to compound INTA-3 (100 mg, 0.305 mmol) is dissolved in toluene (3 mL), and stirred under reflux overnight to form a reaction mixture, cooled to room temperature, and ethyl acetate and water are added to the reaction mixture to form an organic layer. The organic layer is separated, dried by anhydrous sodium sulfate, filtrated, concentrated, and purified by Pre-TLC (ethyl acetate:methanol=15:1) to obtain brown solid compound 38 (80 mg, yield 45%).

2) Compound 38 (80 mg, 0.136 mmol) is dissolved in dichloromethane (4 mL) and trifluoroacetic acid (1 mL), and stirred overnight at room temperature, concentrated to dryness and purified by Pre-TLC to obtain yellow solid compound MED1007-58 (25 mg, yield 46%).

Molecular formula: C$_{21}$H$_{24}$N$_8$O, Molecular weight: 404.47.

$^1$H-NMR (400 MHz, CD3OD): δ 8.445 (s, 1H), 8.377 (d, J=5.2 Hz, 1H), 7.963 (d, J=8.8 Hz, 1H), 7.875 (s, 1H), 7.761 (d, J=8.8 Hz, 1H), 6.846 (d, J=5.2 Hz, 1H), 5.556-5.586 (m, 1H), 3.193-3.209 (m, 4H), 3.086-3.096 (m, 4H), 1.379 (d, J=6.0 Hz, 6H).

MS (ESI) m/z: 405 [M+1]$^+$

52

Example 26

Preparation of 4-(6-(6-(cyclopropyl amino)-9H-purine-2-yl amino) quinoline-4-yl) p-methyl benzoate

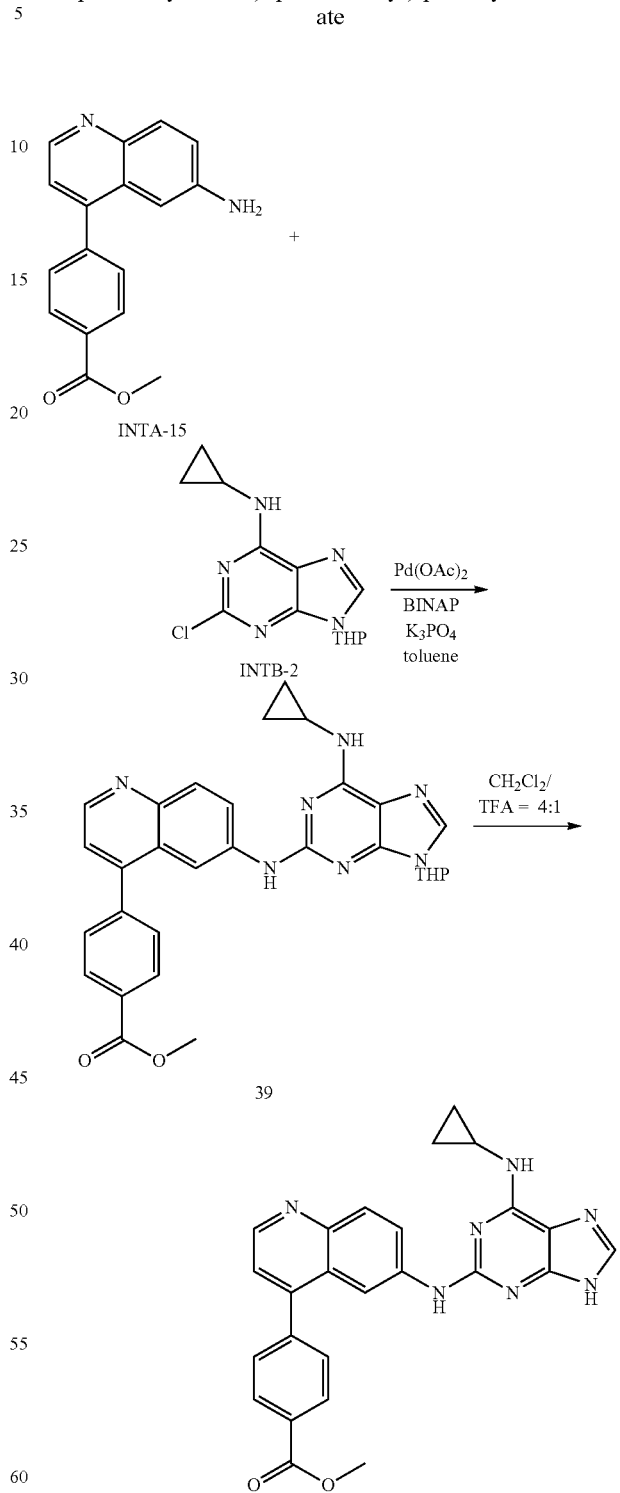

39

MED1007-59

The preparation method of the compound of the example includes the following steps:

1) Compound 2 (105 mg, 0.36 mmol), palladium acetate (8 mg, 0.036 mmol), BINAP (22 mg, 0.036 mmol) and potassium phosphate (152 mg, 0.72 mmol) are added to compound INTA-15 (100 mg, 0.36 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated, and purified by Pre-TLC (ethyl acetate:methanol=15:1) to obtain brown solid compound 39 (50 mg, yield 26%).

2) Compound 39 (50 mg, 0.093 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-59 (10 mg, yield 24%).

Molecular formula: $C_{25}H_{21}N_7O2$, Molecular weight: 451.48.

$^1$H-NMR (400 MHz, CD3OD): δ 8.596 (d, J=4.0 Hz, 1H), 8.384 (s, 1H), 8.061-8.124 (m, 3H), 7.900 (d, J=8.8 Hz, 1H), 7.624-7.703 (m, 3H), 7.295 (d, J=4.4 Hz, 1H), 3.884 (s, 3H), 2.293 (s, 1H), 1.187 (s, 1H), 0.377-0.469 (m, 4H).

MS (m/z): MS (ESI) m/z: 452 [M+1]+

Example 27

Preparation of 4-(6-(6-(cyclopropyl amino)-9H-purine-2-yl amino) quinoline-4-yl) m-methyl benzoate

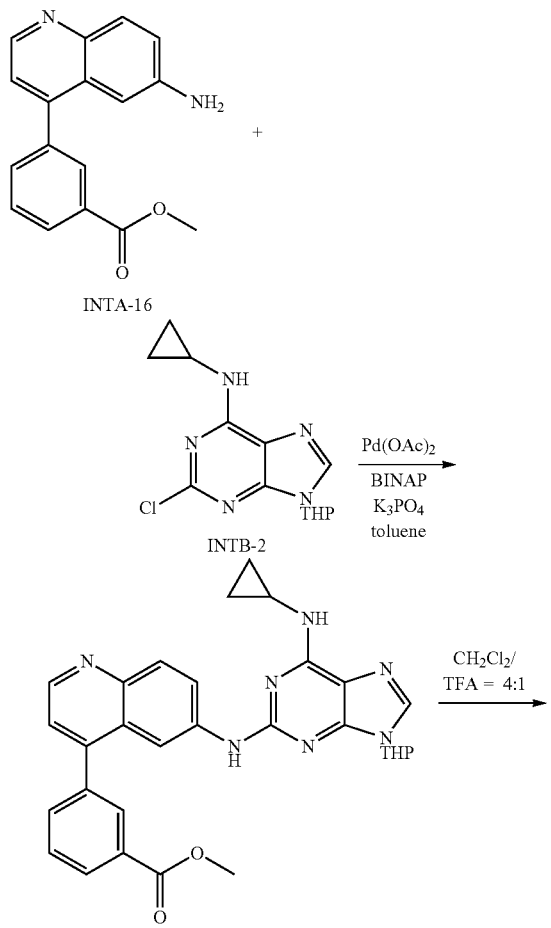

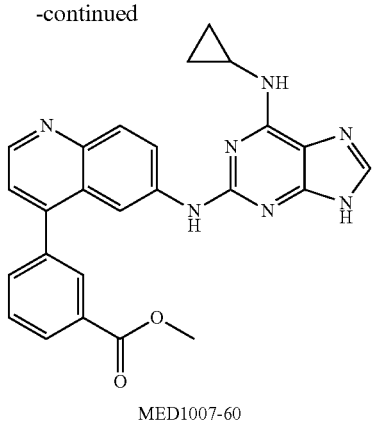

MED1007-60

The preparation method of the compound of the example includes the following steps:

1) Compound INTB-2 (105 mg, 0.36 mmol), palladium acetate (8 mg, 0.036 mmol), BINAP (22 mg, 0.036 mmol) and potassium phosphate (152 mg, 0.72 mmol) are added to compound INTA-16 (100 mg, 0.36 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 40 (50 mg, yield 26%).

2) Compound 40 (50 mg, 0.093 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-60 (11 mg, yield 26%).

Molecular formula: $C_{25}H_{21}N_7O_2$, Molecular weight: 451.48.

1H-NMR (400 MHz, CD3OD): δ 8.599 (d, J=4.8 Hz, 1H), 8.352 (s, 1H), 8.070-8.132 (m, 3H), 7.907 (d, J=8.8 Hz, 1H), 7.592-7.772 (m, 3H), 7.290 (d, J=4.4 Hz, 1H), 3.836 (s, 3H), 2.346 (s, 1H), 1.188 (s, 1H), 0.386-0.506 (m, 4H)

MS (ESI) m/z: 452 [M+1]+

Example 28

Preparation of N6-cyclopropyl-N2-(4-(3-methoxy phenyl) quinoline-6-yl)-9H-purine-2, 6-diamine

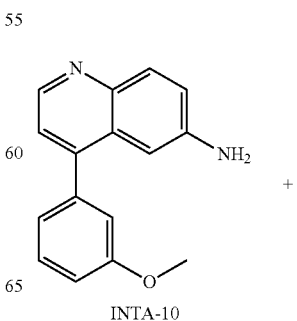

INTA-10

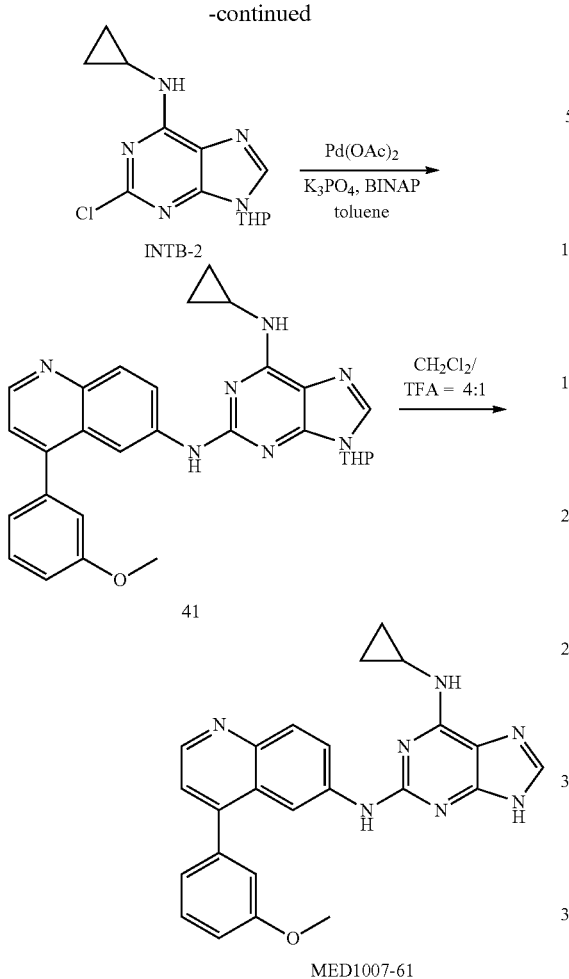

Example 29

Preparation of N6-cyclopropyl-N2-(4-(4-methoxy phenyl) quinoline-6-yl)-9H-purine-2, 6-diamine

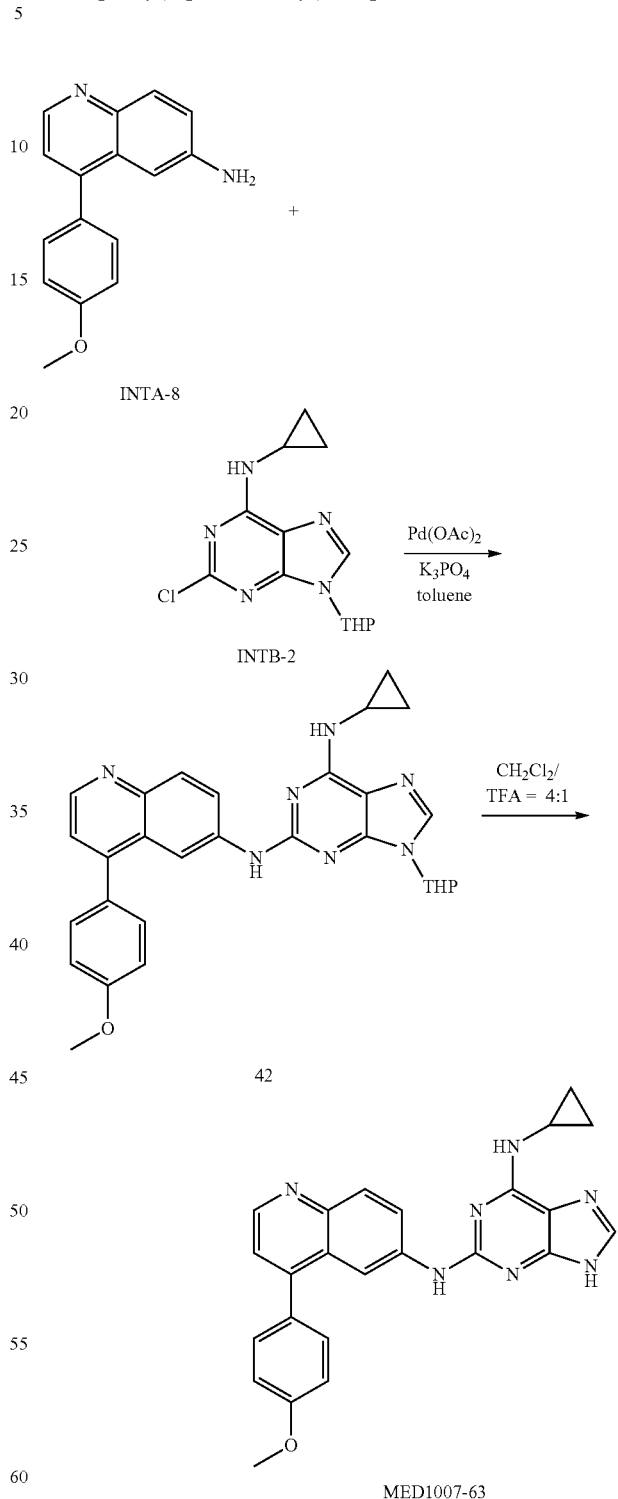

The preparation method of the compound of the example includes the following steps:

1) Compound INTB-2 (105 mg, 0.36 mmol), palladium acetate (8 mg, 0.036 mmol), BINAP (22 mg, 0.036 mmol) and potassium phosphate (152 mg, 0.72 mmol) are added to compound INTA-10 (90 mg, 0.36 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated, and purified by Pre-TLC (ethyl acetate:methanol=15:1) to obtain brown solid compound 41 (60 mg, yield 30%).

2) Compound 41 (60 mg, 0.12 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-61 (10 mg, yield 24%).

Molecular formula: $C_{24}H_{21}N_7O$, Molecular weight: 423.47.

$^1$H-NMR (400 MHz, CD3OD): δ 8.659 (d, J=2.8 Hz, 2H), 8.112 (d, J=9.2 Hz, 1H), 7.978 (d, J=9.2 Hz, 1H), 7.822 (s, 1H), 7.467 (t, J=8.0 Hz, 1H), 7.360 (d, J=8.4 Hz, 1H), 7.158 (d, J=7.6 Hz, 2H), 7.085 (d, J=8.4 Hz, 1H), 3.869 (s, 3H), 3.365 (s, 1H), 2.429 (s, 1H), 0.479-0.618 (m, 4H).

MS (ESI) m/z: 424 [M+1]$^+$

The preparation method of the compound of the example includes the following steps:

1) Compound INTB-2 (105 mg, 0.36 mmol), palladium acetate (8 mg, 0.036 mmol), BINAP (22 mg, 0.036 mmol) and potassium phosphate (152 mg, 0.72 mmol) are added to compound INTA-8 (90 mg, 0.36 mmol) dissolved in toluene (3 mL), and stirred under reflux overnight to form a reaction mixture, cooled to room temperature, and ethyl acetate and water are added to the reaction mixture to form an organic layer. The organic layer is separated, dried by anhydrous sodium sulfate, filtrated, concentrated and purified by Pre-TLC (ethyl acetate:methanol=15:1) to obtain brown solid compound 42 (50 mg, yield 27.5%).

2) Compound 42 (50 mg, 0.1 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-63 (20 mg, yield 47.6%).

Molecular formula: $C_{24}H_{21}N_7O$, Molecular weight: 423.47.

$^1$H-NMR (400 MHz, CD3OD): δ 8.684 (s, 1H), δ 8.647 (d, J=4.4 Hz, 1H), 8.093 (d, J=9.2 Hz, 1H), 7.977 (d, J=8.8 Hz, 1H), 7.824 (s, 1H), 7.562 (d, J=7.6 Hz, 2H), 7.350 (d, J=8.4 Hz, 1H), 7.137 (d, J=7.6 Hz, 2H), 3.918 (s, 3H), 2.437 (s, 1H), 0.479-0.601 (m, 4H).

MS (ESI) m/z: 424 [M+1]$^+$.

Example 30

Preparation of N6-cyclopropyl-N2-(4-(3-fluorophenyl) quinoline-6-yl)-9H-purine-2, 6-diamine

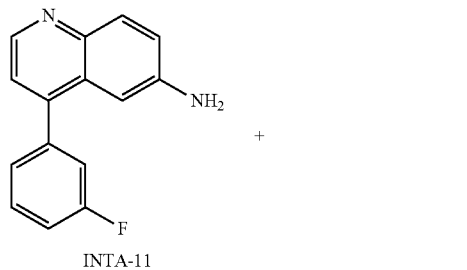
INTA-11

+

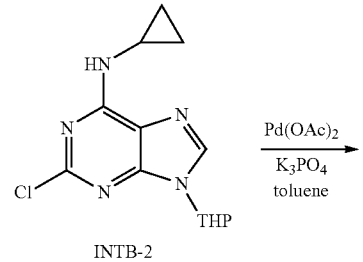
INTB-2

Pd(OAc)$_2$
K$_3$PO$_4$
toluene

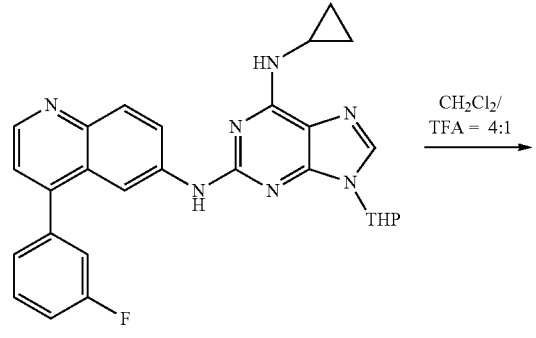
43

CH$_2$Cl$_2$/
TFA = 4:1

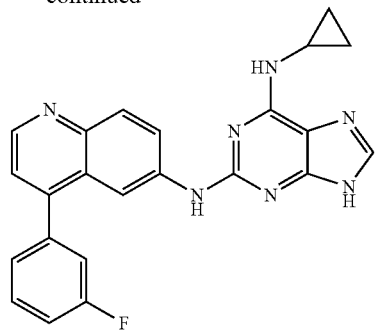
MED1007-64

The preparation method of the compound of the example includes the following steps:

1) Compound INTB-2 (105 mg, 0.36 mmol), palladium acetate (8 mg, 0.036 mmol), BINAP (22 mg, 0.036 mmol) and potassium phosphate (152 mg, 0.72 mmol) are added to compound INTA-11 (86 mg, 0.36 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 43 (30 mg, yield 16.8%).

2) Compound 43 (30 mg, 0.06 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-64 (7 mg, yield 28.4%).

Molecular formula: $C_{23}H_{18}FN_7$, Molecular weight: 411.43.

$^1$H-NMR (400 MHz, CD3OD): δ 8.698 (d, J=4.4 Hz, 1H), δ 8.502 (s, 1H), δ 8.225 (d, J=9.6 Hz, 1H), 8.008 (d, J=9.2 Hz, 1H), 7.611 (q, J1=14.0 Hz, J2=7.2 Hz, 1H), 7.446 (d, J=7.6 Hz, 1H), 7.368-7.399 (m, 2H), 7.293 (t, J=8.8 Hz, 1H), 2.481-2.512 (m, 1H), 0.527-0.674 (m, 4H).

MS (ESI) m/z: 412 [M+1]$^+$.

Example 31

Preparation of N6-cyclopropyl-N2-(4-phenyl quinoline-6-yl)-9-(2, 2, 2-trifluoroethyl)-9H-purine-2, 6-diamine

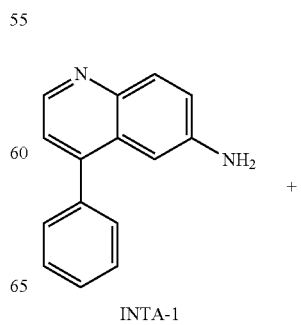
INTA-1

+

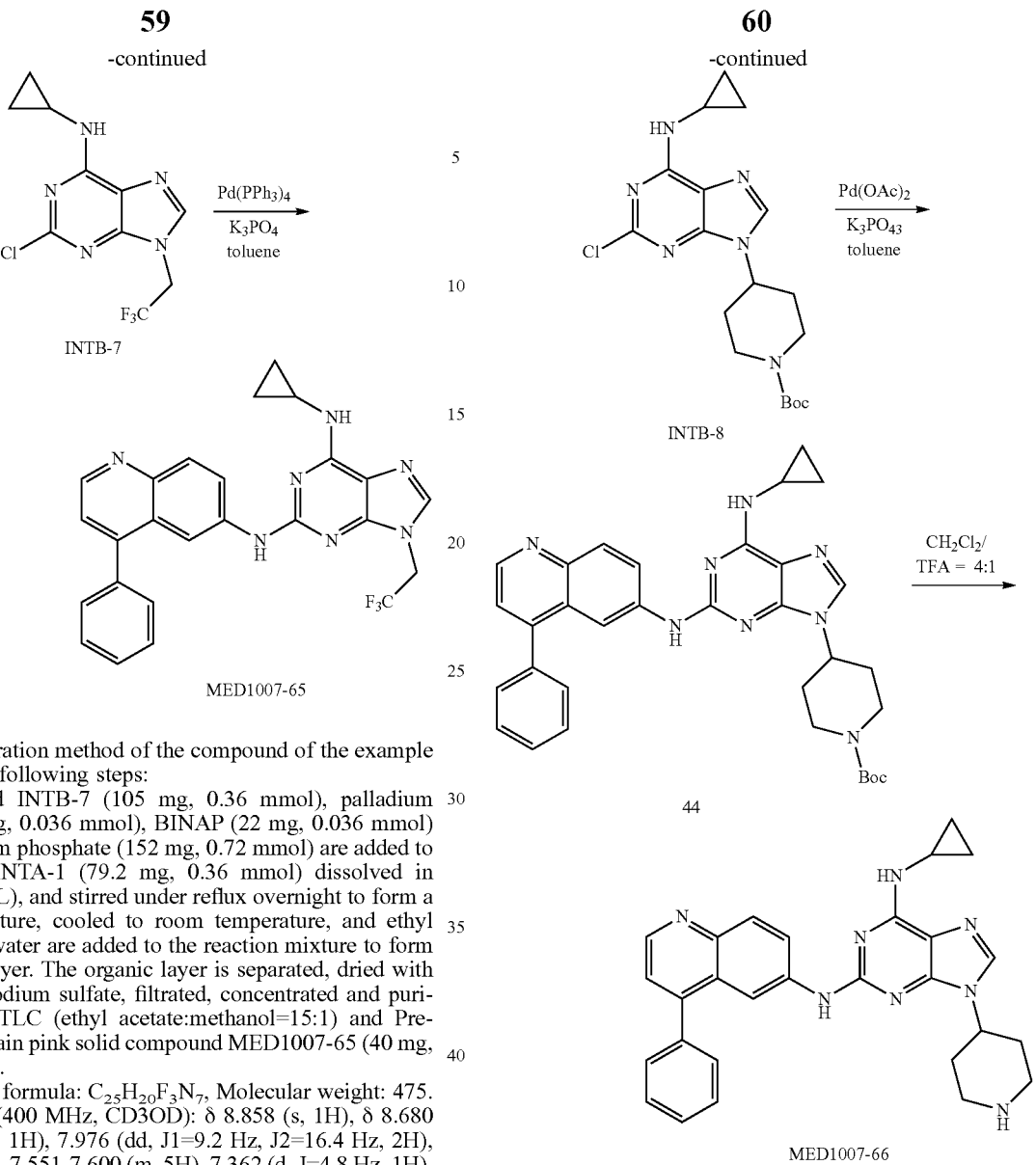

The preparation method of the compound of the example includes the following steps:

Compound INTB-7 (105 mg, 0.36 mmol), palladium acetate (8 mg, 0.036 mmol), BINAP (22 mg, 0.036 mmol) and potassium phosphate (152 mg, 0.72 mmol) are added to Compound INTA-1 (79.2 mg, 0.36 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) and Pre-HPLC to obtain pink solid compound MED1007-65 (40 mg, yield 23.4%).

Molecular formula: $C_{25}H_{20}F_3N_7$, Molecular weight: 475.

$^1$H-NMR (400 MHz, CD3OD): δ 8.858 (s, 1H), δ 8.680 (d, J=4.4 Hz, 1H), 7.976 (dd, J1=9.2 Hz, J2=16.4 Hz, 2H), 7.856 (s, 1H), 7.551-7.600 (m, 5H), 7.362 (d, J=4.8 Hz, 1H), 4.661 (dd, J1=8.8 Hz, J2=17.6 Hz, 2H), 2.593 (s, 1H), 0.536-0.691 (m, 4H).

MS (ESI) m/z: 476.3 [M+1]$^+$.

Example 32

Preparation of N6-cyclopropyl-N2-(4-phenyl quinoline-6-yl)-9-(piperidine-4-yl)-9H-purine-2, 6-diamine

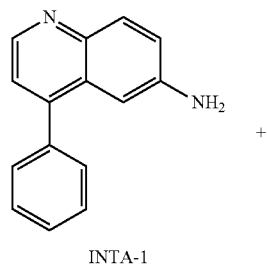

The preparation method of the compound of the example includes the following steps:

1) Compound INTA-1 (56 mg, 0.25 mmol), compound INTB-8 (100 mg, 0.25 mmol), palladium acetate (10 mg, 0.045 mmol), BINAP (30 mg, 0.048 mmol) and potassium phosphate (230 mg, 1.08 mmol) are dissolved in toluene (10 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated, purified by Pre-TLC (ethyl acetate:methanol=8:1) to obtain brown solid compound 3 (50 mg, yield 38%).

2) Compound 44 (55 mg, 0.095 mmol) is dissolved in dichloromethane (4 mL) and trifluoroacetic acid (2 mL), and stirred overnight at room temperature, concentrated to dryness and purified by Pre-HPLC to obtain yellow solid compound MED1007-66 (15 mg, yield 33%).

Molecular formula: $C_{28}H_{28}N_8$, Molecular weight: 476.58.

$^1$H-NMR (400 MHz, CD3OD): δ 8.445 (s, 1H), 8.377 (d, J=5.2 Hz, 1H), 7.963 (d, J=8.8 Hz, 1H), 7.875 (s, 1H), 7.761

(d, J=8.8 Hz, 1H), 6.846 (d, J=5.2 Hz, 1H), 5.556-5.586 (m, 1H), 3.193-3.209 (m, 4H), 3.086-3.096 (m, 4H), 1.379 (d, J=6.0 Hz. 6H).

MS (ESI) m/z: 394.3 [M+1]$^+$.

Example 33

Preparation of N6-(3-methoxy propyl)-N2-(4-phenyl quinoline-6-yl)-9H-purine-2, 6-diamine

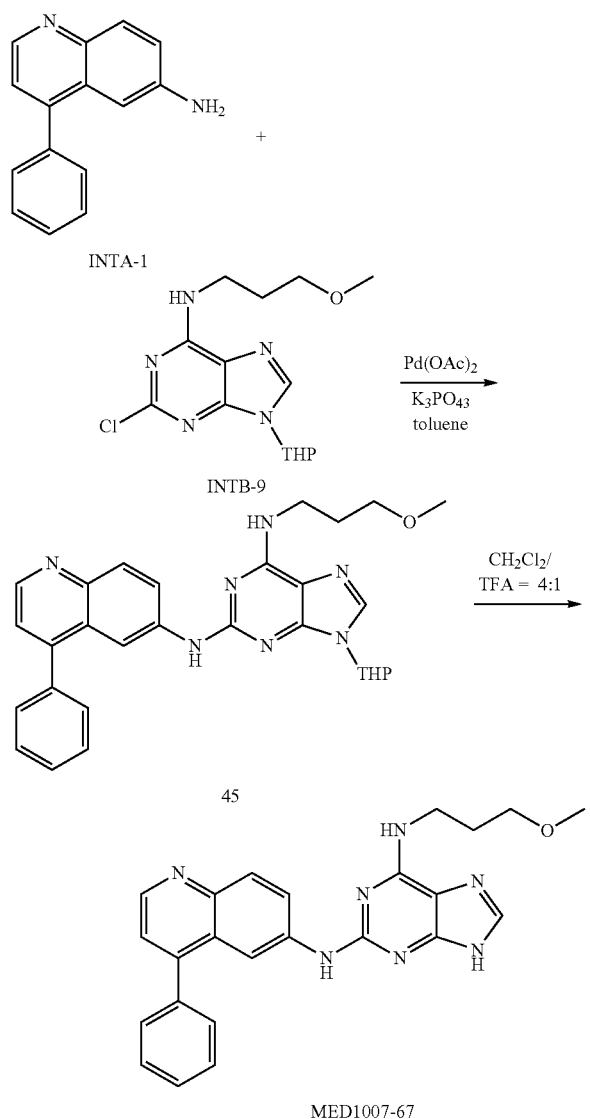

The preparation method of the compound of the example includes the following steps:

1) Compound INTA-1 (68 mg, 0.307 mmol), compound INTB-9 (100 mg, 0.307 mmol), palladium acetate (10 mg, 0.045 mmol), BINAP (30 mg, 0.048 mmol) and potassium phosphate (250 mg, 1.17 mmol) are dissolved in toluene (10 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated, purified by Pre-TLC (ethyl acetate:methanol=25:1) to obtain brown solid compound 45 (50 mg, yield 31.9%).

2) Compound 45 (50 mg, 0.098 mmol) is dissolved in dichloromethane (4 mL) and trifluoroacetic acid (2 mL), and stirred overnight at room temperature, concentrated to dryness and purified by Pre-HPLC to obtain yellow solid compound MED1007-67 (16 mg, yield 38.4%).

Molecular formula: $C_{24}H_{23}N_7O$, Molecular weight: 425.49.

$^1$H-NMR (400 MHz, CD3OD): δ 8.445 (s, 1H), 8.377 (d, J=5.2 Hz, 1H), 7.963 (d, J=8.8 Hz, 1H), 7.875 (s, 1H), 7.761 (d, J=8.8 Hz, 1H), 6.846 (d, J=5.2 Hz, 1H), 5.556-5.586 (m, 1H), 3.193-3.209 (m, 4H), 3.086-3.096 (m, 4H), 1.379 (d, J=6.0 Hz, 6H)

MS (ESI) m/z: 426.3 [M+1]+

Example 34

Preparation of N6-(2-methoxy ethyl)-N2-(4-phenyl quinoline-6-yl)-9H-purine-2, 6-diamine

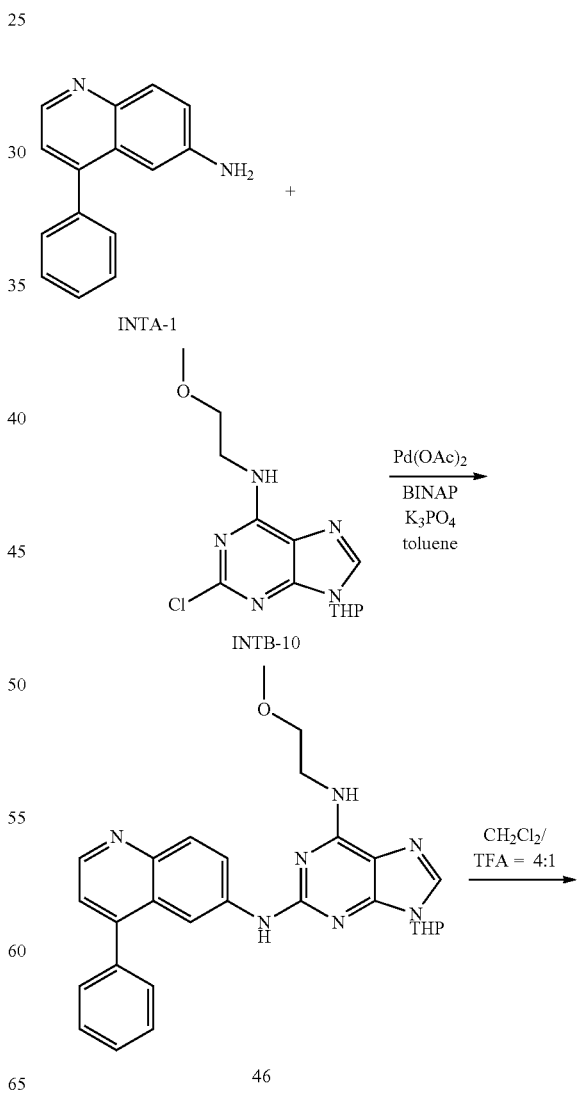

-continued

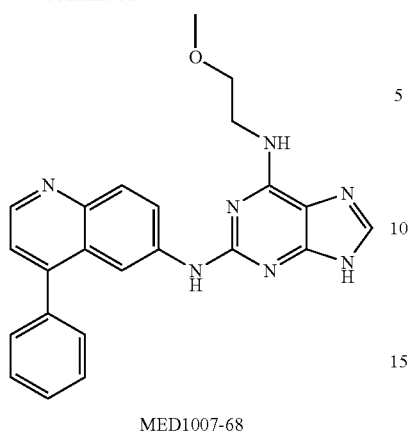

MED1007-68

The preparation method of the compound of the example includes the following steps:

1) Compound INTB-10 (112 mg, 0.36 mmol), palladium acetate (8 mg, 0.036 mmol), BINAP (22 mg, 0.036 mmol) and potassium phosphate (152 mg, 0.72 mmol) are added to compound INTA-1 (79 mg, 0.36 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated, and purified by Pre-TLC (ethyl acetate:methanol=15:1) to obtain brown solid compound 46 (45 mg, yield 25%).

2) Compound 46 (45 mg, 0.091 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-68 (10 mg, yield 27%).

Molecular formula: $C_{23}H_{21}N_7O$, Molecular weight: 411.46.

$^1$H-NMR (400 MHz, DMSO-d6): δ 9.445 (s, 1H), 8.761 (d, J=4.0 Hz, 2H), 8.410 (s, 1H), 7.956-8.227 (m, 3H), 7.384-7.607 (m, 7H), 3.289-3.441 (m, 7H).

MS (ESI) m/z: 412.2 [M+1]$^+$.

Example 35

Preparation of 2-(2-(4-phenyl quinoline-6-yl amino)-9H-purine-6-yl amino) ethanol

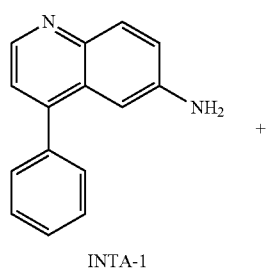

INTA-1

-continued

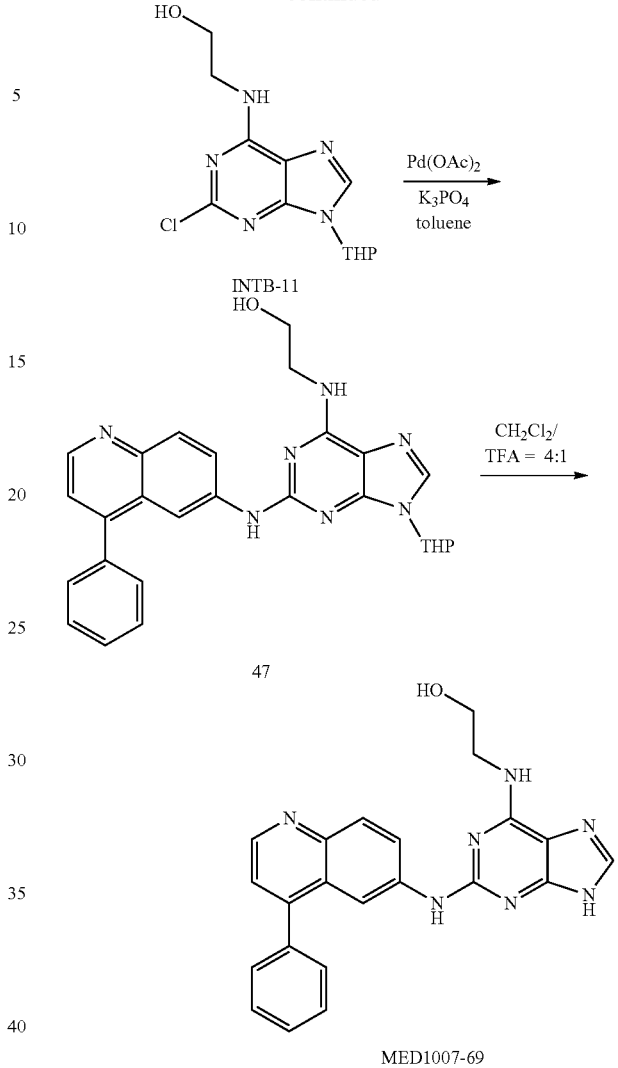

The preparation method of the compound of the example includes the following steps:

Compound INTB-11 (136 mg, 0.45 mmol), palladium acetate (10 mg, 0.045 mmol), BINAP (30 mg, 0.045 mmol) and potassium phosphate (240 mg, 0.9 mmol) are added to compound INTA-1 (100 mg, 0.45 mmol) dissolved in toluene (3 mL), and stirred under reflux overnight to form a reaction mixture, cooled to room temperature, and ethyl acetate and water are added to the reaction mixture to form an organic layer. The organic layer is separated, dried by anhydrous sodium sulfate, filtrated, concentrated, and purified by Pre-TLC (ethyl acetate:methanol=15:1) to obtain brown solid compound 47 (70 mg, yield: 33%).

Compound 47 (70 mg, 0.15 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-69 (30 mg, yield 52%).

Molecular formula: $C_{22}H_{19}N_7O$, Molecular weight: 397.

$^1$H-NMR (400 MHz, CD3OD): δ 8.695 (d, J=4.4 Hz, 1H), δ 8.452 (s, 1H), 8.091 (d, J=10.4 Hz, 1H), 8.004 (d, J=9.2 Hz, 1H), 7.819 (s, 1H), 7.549-7.629 (m, 5H), 7.392 (d, J=4.8 Hz, 1H), 3.624-3.648 (m, 2H), 3.366 (m, 2H).

MS (ESI) m/z: 398.4 [M+1]$^+$.

Example 36

Preparation of N6-(2-aminoethyl 1)-N2-(4-phenyl quinoline-6-yl)-9H-purine-2, 6-diamine

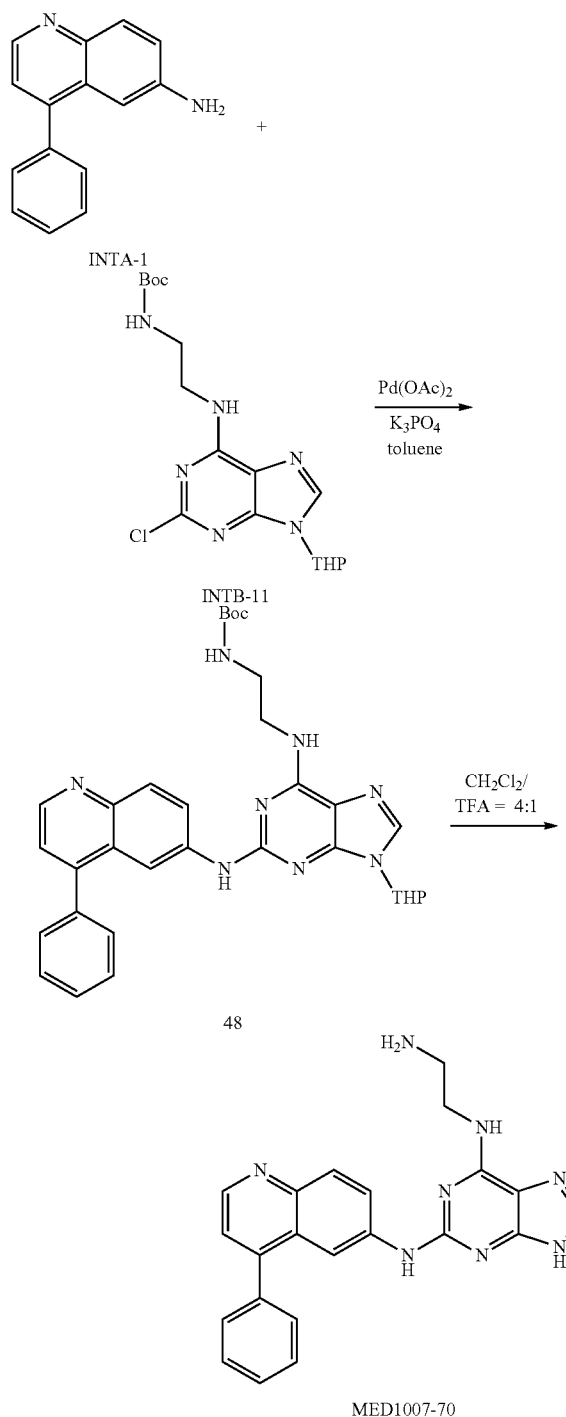

The preparation method of the compound of the example includes the following steps:

1) Compound INTB-11 (180 mg, 0.45 mmol), palladium acetate (10 mg, 0.045 mmol), BINAP (30 mg, 0.045 mmol) and potassium phosphate (240 mg, 0.9 mmol) are added to compound INTA-1 (100 mg, 0.45 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated, and purified by Pre-TLC (ethyl acetate:methanol=15:1) to obtain brown solid compound 48 (50 mg, yield 19.1%).

2) Compound 48 (50 mg, 0.09 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-70 (20 mg, yield 58.8%).

Molecular formula: $C_{22}H_{20}N_8$, Molecular weight: 396.

$^1$H-NMR (400 MHz, CD3OD): δ 8.981 (d, J=5.2 Hz, 1H), δ 8.597-8.649 (m, 2H), 8.377 (s, 1H), 8.242 (d, J=9.6 Hz, 1H), 7.921 (d, J=6.0 Hz, 1H), 7.721-7.784 (m, 5H), 3.664 (m, 2H), 3.817 (t, J=5.2 Hz, 2H).

MS (ESI) m/z: 397.3 $[M+1]^+$.

Example 37

Preparation of N6-cyclobutyl-N2-(4-(3-methoxy phenyl) quinoline-6-yl)-9H-purine-2, 6-diamine

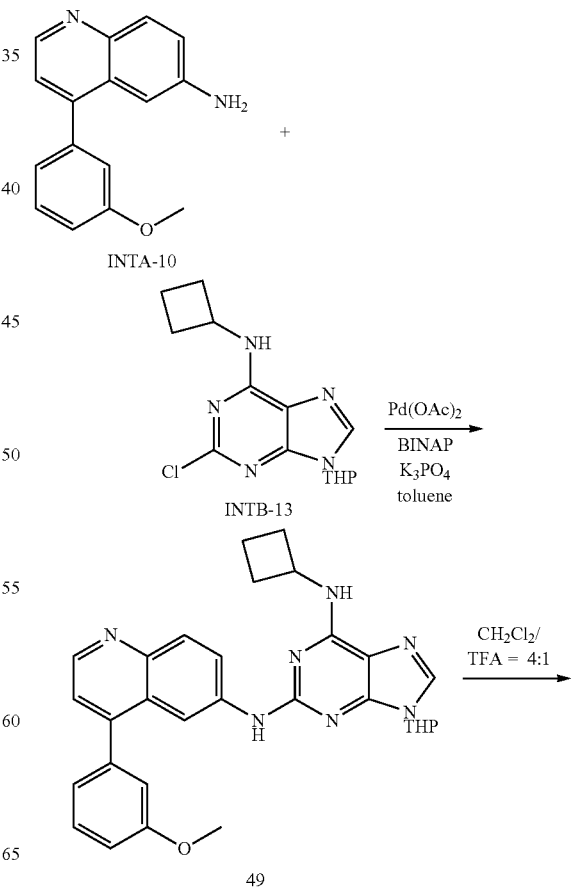

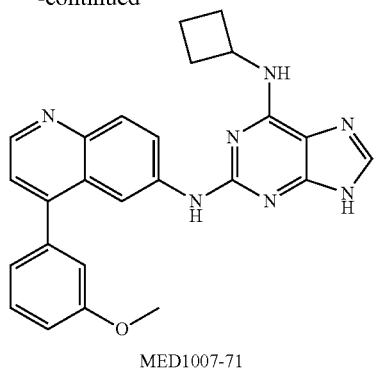

MED1007-71

The preparation method of the compound of the example includes the following steps:

1) Compound INTB-13 (110 mg, 0.36 mmol), palladium acetate (8 mg, 0.036 mmol), BINAP (22 mg, 0.036 mmol) and potassium phosphate (152 mg, 0.72 mmol) are added to compound INTA-10 (90 mg, 0.36 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated, and purified by Pre-TLC (ethyl acetate:methanol=15:1) to obtain brown solid compound 49 (50 mg, yield 27%).

2) Compound 49 (50 mg, 0.096 mmol) is dissolved in dichloromethane (4 mL) and trifluoroacetic acid (1 mL), and stirred overnight at room temperature, concentrated to dryness, and purified by Pre-TLC (dichloromethane:methanol=10:1) to obtain yellow solid compound MED1007-71 (10 mg, yield 24%).

Molecular formula: $C_{25}H_{23}N_7O$, Molecular weight: 437.50.

$^1$H-NMR (400 MHz, CD3OD): δ 8.558 (d, J=4.4 Hz, 1H), 8.409 (s, 1H), 7.708-8.002 (m, 3H), 7.277-7.414 (m, 2H), 6.996-7.100 (m, 3H), 3.759 (s, 3H), 3.249 (s, 1H), 2.169-2.200 (m, 2H), 1.803-1.850 (m, 2H), 4.575-1.649 (m, 2H).

MS (ESI) m/z: 438.3 [M+1]$^+$.

Example 38

Preparation of N6-cyclobutyl-N2-(4-(4-fluorophenyl) quinoline-6-yl)-9H-purine-2, 6-diamine

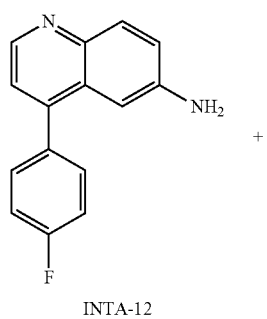

INTA-12

+

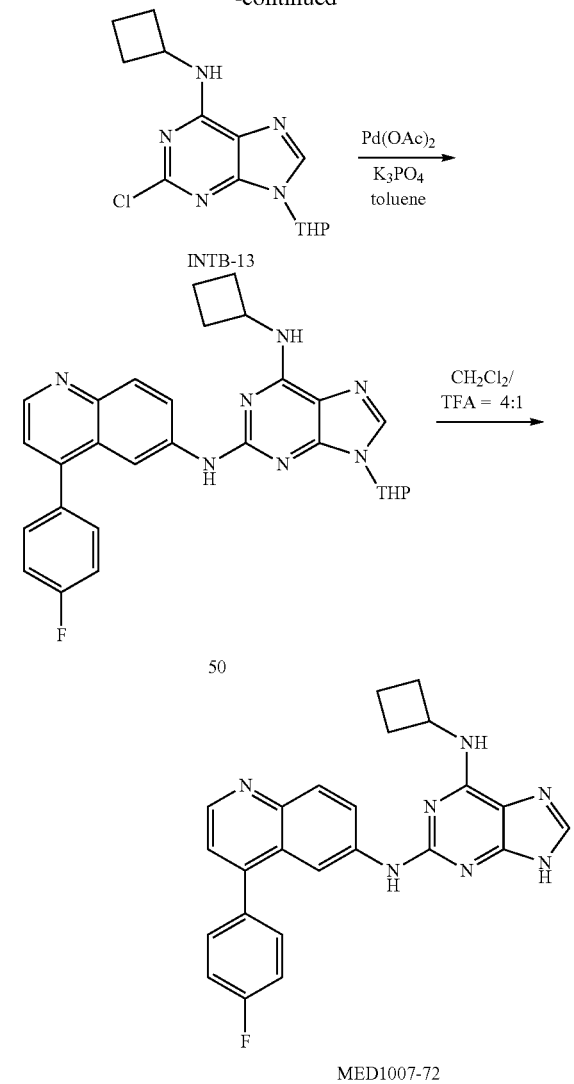

MED1007-72

The preparation method of the compound of the example includes the following steps:

1) Compound INTB-13 (138.6 mg, 0.45 mmol), palladium acetate (10 mg, 0.045 mmol), BINAP (30 mg, 0.045 mmol) and potassium phosphate (240 mg, 0.9 mmol) are added to compound INTA-12 (107 mg, 0.45 mmol) dissolved in toluene (3 mL), and stirred under reflux overnight to form a reaction mixture, cooled to room temperature, and ethyl acetate and water are added to the reaction mixture to form an organic layer. The organic layer is separated, dried by anhydrous sodium sulfate, filtrated, concentrated, and purified by Pre-TLC (ethyl acetate:methanol=15:1) to obtain brown solid compound 50 (60 mg, yield: 26.1%).

2) Compound 50 (60 mg, 0.12 mmol) is dissolved in dichloromethane (4 mL) and trifluoroacetic acid (1 mL), and stirred overnight at room temperature, concentrated to dryness, and purified by Pre-TLC (dichloromethane:methanol=10:1) to obtain yellow solid compound MED1007-72 (10 mg, yield 20.1%).

Molecular formula: $C_{24}H_{20}FN_7$, Molecular weight: 425.

$^1$H-NMR (400 MHz, CD3OD): δ 8.563 (d, J=4.4 Hz, 1H), δ 8.298 (s, 1H), 8.062 (d, J=8.0 Hz, 1H), 7.914 (d, J=9.2 Hz, 1H), 7.732 (s, 1H), 7.581-7.621 (m, 2H), 7.258-7.318 (m,

3H), 4.218 (t, J=7.2 Hz, 1H), 2.218-2.251 (m, 2H), 1.865-1.895 (m, 2H), 1.656-1.684 (m, 2H).

MS (ESI) m/z: 246.3 [M+1]$^+$.

Example 39

Preparation of 3-(2-(4-phenyl quinoline-6-yl amino)-9H-purine-6-yl amino) propyl-1-ol

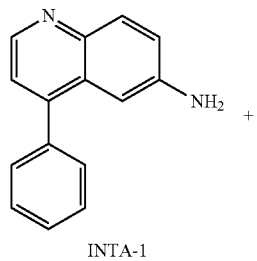
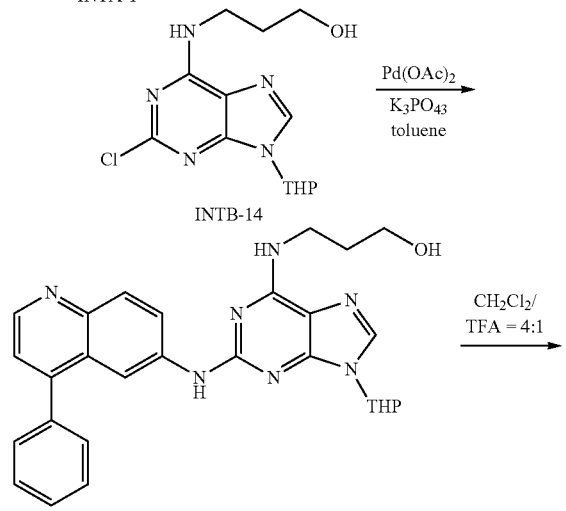

The preparation method of the compound of the example includes the following steps:

1) Compound INTA-1 (71 mg, 0.32 mmol), compound INTB-14 (100 mg, 0.32 mmol), palladium acetate (10 mg, 0.045 mmol), BINAP (30 mg, 0.048 mmol) and potassium phosphate (250 mg, 1.17 mmol) are dissolved in toluene (10 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated, and purified by Pre-TLC (ethyl acetate:methanol=10:1) to obtain brown solid compound 51 (45 mg, yield 28.4%).

2) Compound 51 (45 mg, 0.091 mmol) is dissolved in dichloromethane (4 mL) and trifluoroacetic acid (2 mL), and stirred overnight at room temperature, concentrated to dryness, and purified by Pre-TLC to obtain yellow solid compound MED1007-73 (14 mg, yield 37.4%).

Molecular formula: $C_{23}H_{21}N_7O$, Molecular weight: 411.46.

$^1$H-NMR (400 MHz, CD3OD): δ 8.445 (s, 1H), 8.377 (d, J=5.2 Hz, 1H), 7.963 (d, J=8.8 Hz, 1H), 7.875 (s, 1H), 7.761 (d, J=8.8 Hz, 1H), 6.846 (d, J=5.2 Hz, 1H), 5.556-5.586 (m, 1H), 3.193-3.209 (m, 4H), 3.086-3.096 (m, 4H), 1.379 (d, J=6.0 Hz, 6H).

MS (ESI) m/z: 412.4 [M+1]$^+$.

Example 40

Preparation of N6-cyclobutyl-N2-(4-phenyl quinoline-6-yl)-9H-purine-2, 6-diamine

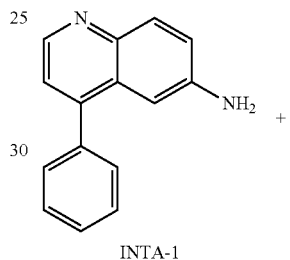
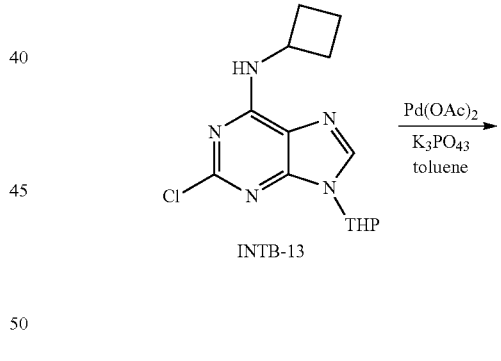
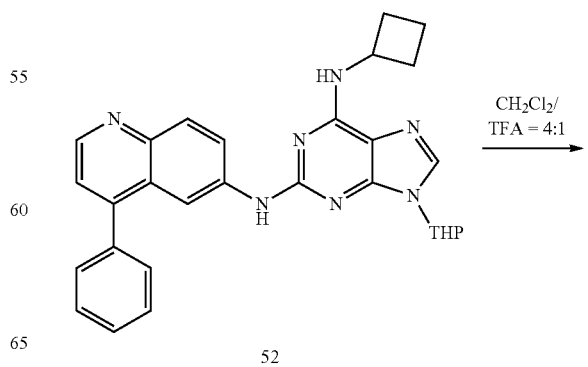

-continued

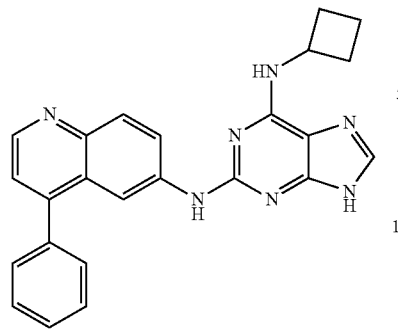

MED1007-75

The preparation method of the compound of the example includes the following steps:

1) Compound INTA-1 (72 mg, 0.32 mmol), compound INTB-13 (100 mg, 0.32 mmol), palladium acetate (10 mg, 0.045 mmol), BINAP (30 mg, 0.048 mmol) and potassium phosphate (250 mg, 1.17 mmol) are dissolved in toluene (10 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated, and purified by Pre-TLC (ethyl acetate:methanol=30:1) to obtain brown solid compound 52 (45 mg, yield: 28.6%).

2) Compound 52 (45 mg, 0.091 mmol) is dissolved in dichloromethane (4 mL) and trifluoroacetic acid (2 mL), and stirred overnight at room temperature, concentrated to dryness, and purified by Pre-HPLC to obtain yellow solid compound MED1007-75 (15 mg, yield 40.5%).

Molecular formula: $C_{24}H_{21}N_7$, Molecular weight: 407.47.

$^1$H-NMR (400 MHz, CD3OD): δ 8.445 (s, 1H), 8.377 (d, J=5.2 Hz, 1H), 7.963 (d, J=8.8 Hz, 1H), 7.875 (s, 1H), 7.761 (d, J=8.8 Hz, 1H), 6.846 (d, J=5.2 Hz, 1H), 5.556-5.586 (m, 1H), 3.193-3.209 (m, 4H), 3.086-3.096 (m, 4H), 1.379 (d, J=6.0 Hz, 6H).

MS (ESI) m/z: 408.4 [M+1]$^+$.

Example 41

Preparation of N6-cyclopropyl-N2-(4-(3-ethoxy phenyl) quinoline-6-yl)-9H-purine-2, 6-diamine

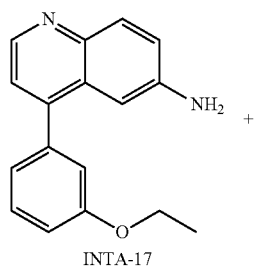

INTA-17

-continued

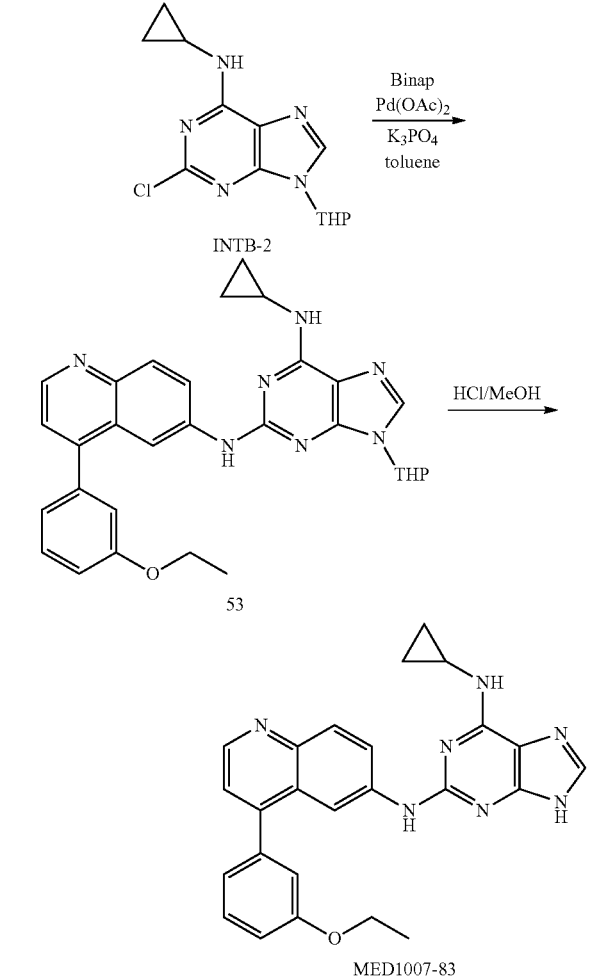

The preparation method of the compound of the example includes the following steps:

1) Compound INTA-17 (198 mg, 0.749 mmol), compound INTB-2 (200 mg, 0.473 mmol), palladium acetate (15 mg, 0.068 mmol), BINAP (30 mg, 0.064 mmol) and potassium phosphate (500 mg, 2.24 mmol) are dissolved in toluene (15 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated, and purified by Pre-TLC (ethyl acetate:methanol=30:1) to obtain brown solid compound 53 (60 mg, yield 44%).

2) Compound 53 (60 mg, 0.115 mmol) is dissolved in methanol (10 mL) saturated with hydrochloric acid, and stirred overnight at room temperature, concentrated to dryness, and purified by Pre-HPLC to obtain yellow solid compound MED1007-83 (9 mg, yield 17.8%).

Molecular formula: $C_{25}H_{23}N_7O$, Molecular weight: 437.5.

$^1$H-NMR (400 MHz, DMSO 8.445 (s, 1H), 8.377 (d, J=5.2 Hz, 1H), 7.963 (d, J=8.8 Hz, 1H), 7.875 (s, 1H), 7.761 (d, J=8.8 Hz, 1H), 6.846 (d, J=5.2 Hz, 1H), 5.556-5.586 (m, 1H), 3.193-3.209 (m, 4H), 3.086-3.096 (m, 4H), 1.379 (d, J=6.0 Hz, 6H).

MS (ESI) m/z: 438.4 [M+1]$^+$.

Example 42

Preparation of N6-cyclopropyl-N2-(4-(3, 4-dimethoxy phenyl) quinoline-6-yl)-9H-purine-2, 6-diamine

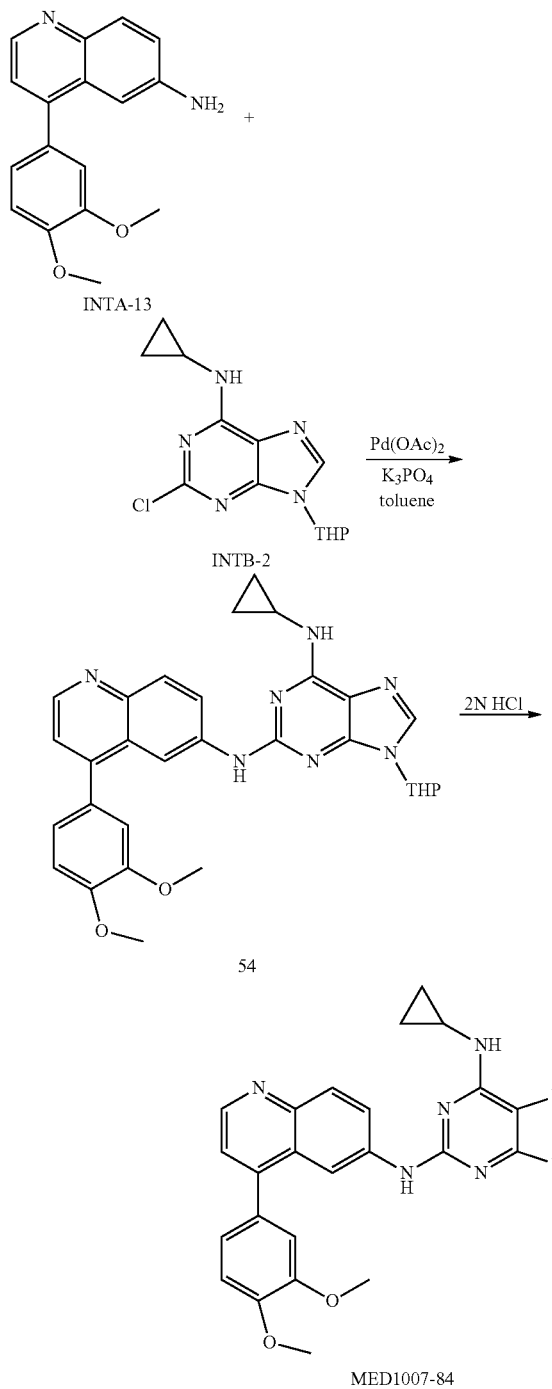

compound INTA-13 (119 mg, 0.45 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 54 (100 mg, yield 42.6%).

2) Compound 54 (60 mg, 0.125 mmol) is dissolved in 2N hydrochloric acid methanol (5 mL), and stirred overnight at room temperature, concentrated to dryness and purified by Pre-TLC (dichloromethane:methanol=10:1) to obtain yellow solid compound MED1007-84 (15 mg).

Molecular formula: $C_{25}H_{23}N_7O_2$, Molecular weight: 453.5.

$^1$H-NMR (400 MHz, CD3OD): δ 8.686 (s, 1H), 8.518 (d, J=4.4 Hz, 1H), δ 7.944 (d, J=8.4 Hz, 1H), 7.850 (d, J=8.4 Hz, 1H), 7.720 (s, 1H), 7.243 (d, J=4.0 Hz, 1H), 7.020-7.092 (m, 3H), 3.828 (s, 3H), 3.753 (s, 3H), 3.222 (s, 3H), 2.350 (s, 1H), 1.184 (s, 1H), 0.358-0.471 (m, 4H).

MS (ESI) m/z: 454.3 [M+1]$^+$.

Example 43

Preparation of N2-(4-(benzo[1,3]-dioxole-5-yl) quinoline-6-yl)-N6-cyclopropane-9H-purine-2, 6-diamine

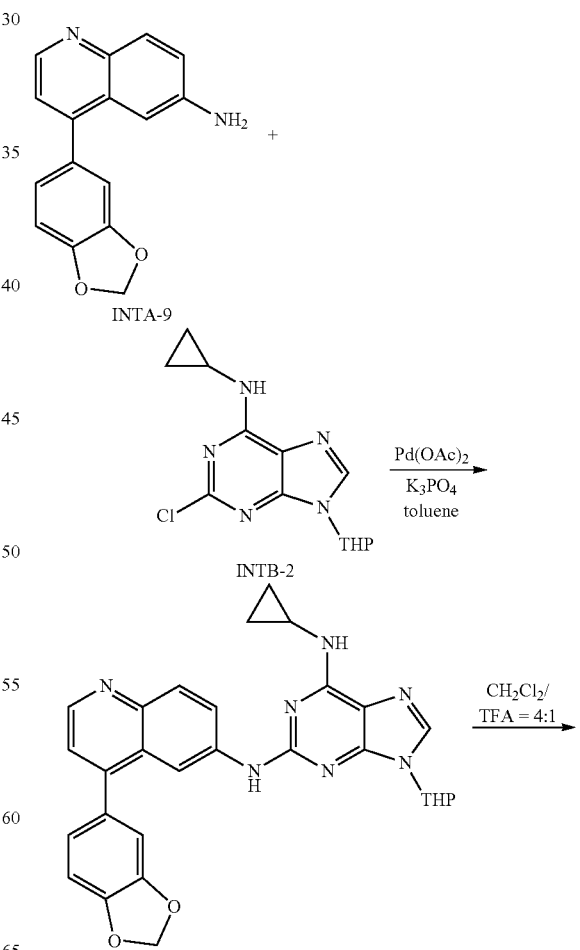

The preparation method of the compound of the example includes the following steps:

1) Compound INTB-2 (132 mg, 0.45 mmol), palladium acetate (10 mg, 0.045 mmol), BINAP (30 mg, 0.045 mmol) and potassium phosphate (240 mg, 0.9 mmol) are added to

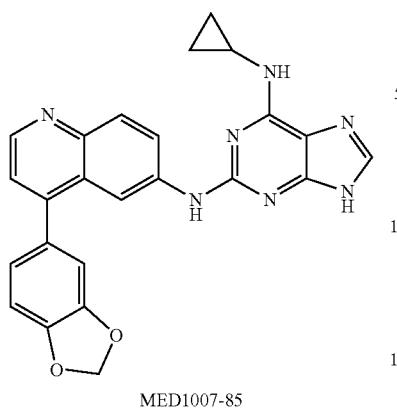

MED1007-85

The preparation method of the compound of the example includes the following steps:

1) Compound INTB-2 (132 mg, 0.45 mmol), palladium acetate (10 mg, 0.045 mmol), BINAP (30 mg, 0.045 mmol) and potassium phosphate (240 mg, 0.9 mmol) are added to compound INTA-9 (119 mg, 0.45 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 55 (100 mg, yield 42.6%).

2) Compound 55 (60 mg, 0.125 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-85 (35 mg, yield 41.8%).

Molecular formula: $C_{23}H_{19}N_7$, Molecular weight: 437.

$^1$H-NMR (400 MHz, CD3OD): δ 8.647 (d, J=2.8 Hz, 2H), δ 8.138 (d, J=8.4 Hz, 1H), 7.978 (d, J=9.2 Hz, 1H), 7.833 (s, 1H), 7.358 (d, J=4.4 Hz, 1H), 7.023-7.123 (m, 3H), 6.096 (s, 2H), 2.577-2.593 (m, 1H), 0.533-0.689 (m, 4H).

MS (ESI) m/z: 438.4 [M+1]$^+$.

Example 44

Preparation of N6-cyclopropyl-N2-(4-(2-methoxy phenyl) quinoline-6-yl)-9H-purine-2, 6-diamine

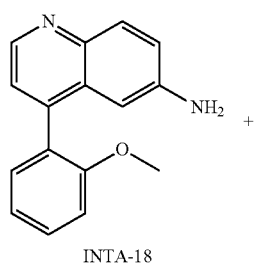

INTA-18

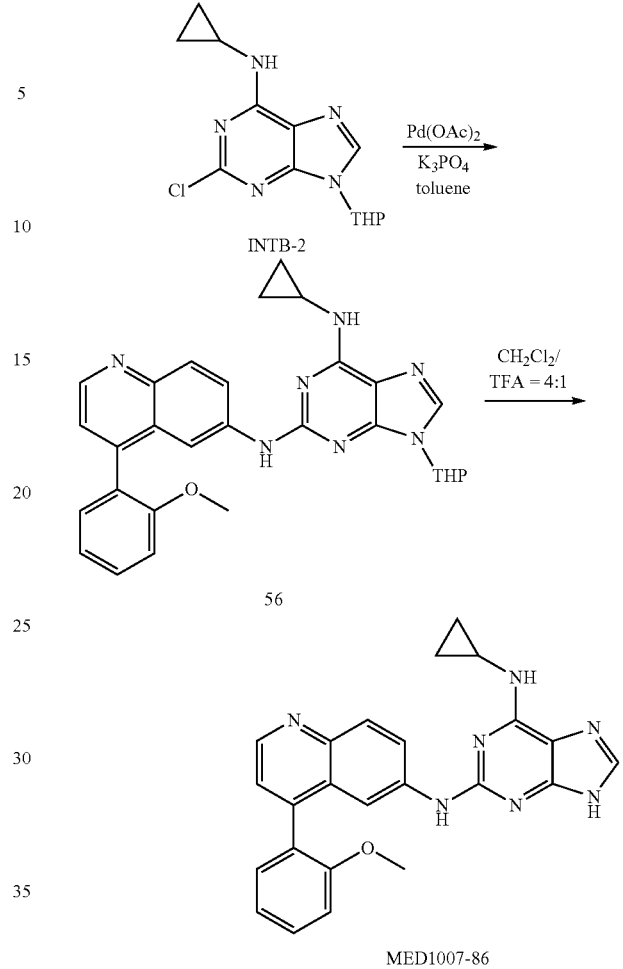

MED1007-86

The preparation method of the compound of the example includes the following steps:

1) Compound INTB-2 (105 mg, 0.36 mmol), palladium acetate (8 mg, 0.036 mmol), BINAP (22 mg, 0.036 mmol) and potassium phosphate (152 mg, 0.72 mmol) are added to compound INTA-18 (90 mg, 0.36 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 56 (50 mg, yield 27.5%).

2) Compound 56 (50 mg, 0.1 mmol) is dissolved in dichloromethane (4 mL) and trifluoroacetic (1 mL), and stirred overnight at room temperature, concentrated to dryness and purified by Pre-TLC (dichloromethane:methanol=10:1) to obtain yellow solid compound MED1007-86 (30 mg, yield 71.4%).

Molecular formula: $C_{24}H_{21}N_7O$, Molecular weight: 423.

$^1$H-NMR (400 MHz, CD3OD): δ 8.658 (d, J=4.4 Hz, 1H), δ 8.223 (d, J=9.2 Hz, 1H), 8.144 (s, 1H), 7.969 (d, J=9.2 Hz, 1H), 7.811 (s, 1H), 7.524 (t, J=8.0 Hz, 1H), 7.319-7.342 (m, 2H), 7.176 (d, J=17.2 Hz, 1H), 7.136 (t, J=7.2 Hz, 1H), 3.739 (s, 3H), 2.443 (s, 1H), 0.489-0.697 (m, 4H).

MS (ESI) m/z: 424.2 [M+1]$^+$.

Example 45

Preparation of N6-cyclopropyl-N2-(4-(2-(methylthio)phenyl) quinoline-6-yl)-9H-purine-2, 6-diamine

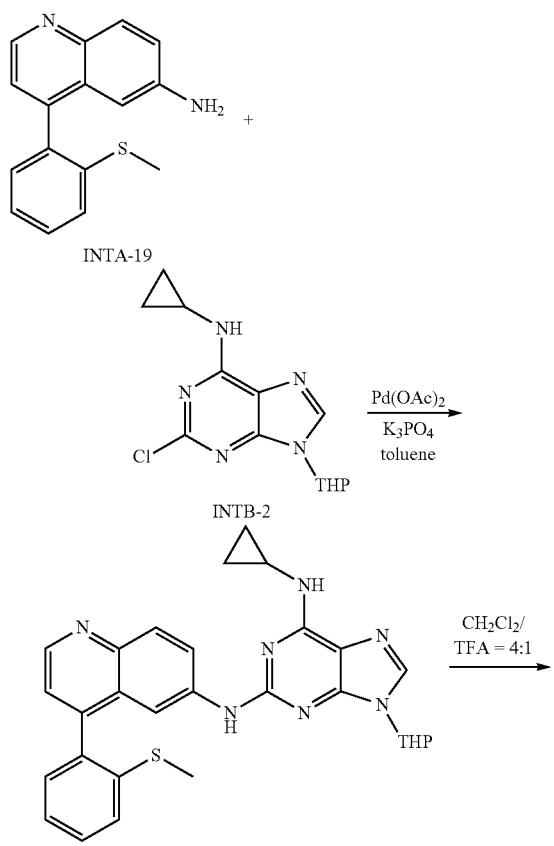

The preparation method of the compound of the example includes the following steps:

1) Compound INTB-2 (105 mg, 0.36 mmol), palladium acetate (8 mg, 0.036 mmol), BINAP (22 mg, 0.036 mmol) and potassium phosphate (152 mg, 0.72 mmol) are added to compound INTA-19 (96 mg, 0.36 mmol) dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtered, concentrated and purified by Pre-TLC (ethyl acetate:methanol=15:1) to obtain brown solid compound 57 (60 mg, yield 32%).

2) Compound 57 (60 mg, 0.11 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-87 (30 mg, yield 59.5%).

Molecular formula: $C_{24}H_{21}N_7S$, Molecular weight: 440.

$^1$H-NMR (400 MHz, DMSO): δ 12.339 (s, 1H), 9.244 (s, 1H), 8.676 (d, J=4.0 Hz, 1H), 8.268-8.293 (m, 1H), 7.798-8.010 (m, 3H), 7.425-7.526 (m, 3H), 7.210-7.321 (m, 3H), 2.332 (s, 3H), 2.286 (b, 1H), 0.423-0.523 (m, 4H).

MS (ESI) m/z: 440.2 $[M+1]^+$.

Example 46

Preparation of N6-cyclopropyl-N2-(4-(3-(methylthio)phenyl) quinoline-6-yl)-9H-purine-2, 6-diamine

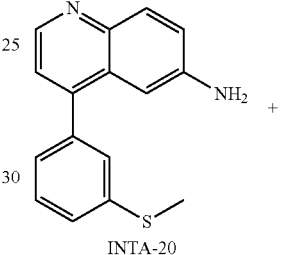

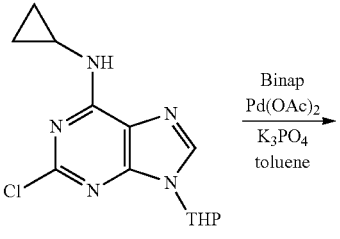

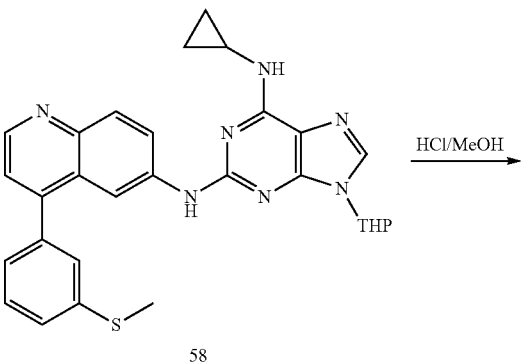

-continued

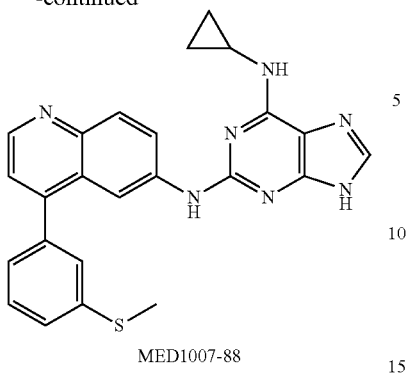

MED1007-88

The preparation method of the compound of the present example includes the following steps:

1) Compound INTA-20 (181 mg, 0.68 mmol), compound INTB-2 (200 mg, 0.68 mmol), palladium acetate (15 mg, 0.068 mmol), BINAP (30 mg, 0.064 mmol) and potassium phosphate (500 mg, 2.24 mmol) are dissolved in toluene (15 mL), and stirred under reflux overnight to form a reaction mixture, cooled to room temperature, and ethyl acetate and water are added to the reaction mixture to form an organic layer. The organic layer is separated, dried by anhydrous sodium sulfate, filtrated, concentrated and purified by Pre-TLC (ethyl acetate:methanol=20:1) to obtain yellow solid compound 58 (80 mg, yield 24%).

2) Compound 58 (80 mg, 0.115 mmol) is dissolved in methanol solution (10 mL) saturated with hydrochloric acid, and stirred overnight at room temperature, concentrated to dryness and purified by Pre-HPLC to obtain yellow solid compound MED1007-88 (21 mg, yield 35%).

Molecular formula: $C_{24}H_{21}N_7S$, Molecular weight: 439.1.

$^1$H-NMR (400 MHz, DMSO 0.449 (d, J=7.2 Hz, 4H), 2.330-2.433 (m, 1H), 2.535 (s, 3H), 7.422-7.655 (m, 4H), 8.154 (d, J=2.4 Hz, 1H), 8.277-8.423 (m, 2H), 8.667 (m, 1H), 8.914 (d, J=1.8 Hz, 1H), 9.912-9.924 (m, 1H).

MS (m/z): MS (ESI) m/z: 440 [M+1]$^+$.

Example 47

Preparation of N6-cyclopropyl-N2-(4-phenyl quinoline-6-yl)-9H-purine-2, 6-diammonium salt dihydrate di-methanesulfonate

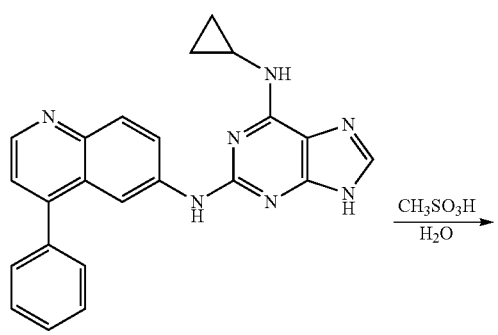

MED1007-31

$\xrightarrow{CH_3SO_3H}_{H_2O}$

-continued

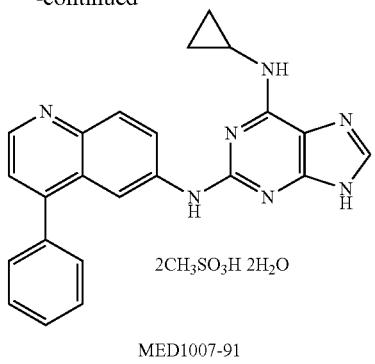

2CH$_3$SO$_3$H 2H$_2$O

MED1007-91

The preparation method of the compound of the example includes the following steps:

Methanesulfonic acid (52 mg, 0.51 mmol) with ethanol (4 mL) and water (dropwise add) are added to a solution of compound MED1007-31 (50 mg, 0.127 mmol), and stirred overnight at room temperature, and filtrated and washed with ethanol and ethyl acetate to obtain yellow solid MED1007-91 (35 mg, yield 44%).

Molecular formula: $C_{25}H_{33}N_7O_8S_2$, Molecular weight: 624.

$^1$H-NMR (400 MHz, CD3OD): δ 9.038 (d, J=5.6 Hz, 1H), δ 8.062-8.657 (m, 3H), 8.281 (d, J=9.2 Hz, 1H), 7.963 (d, J=5.6 Hz, 1H), 7.700-7.782 (m, 5H), 2.737 (s, 6H), 2.419 (b, 1H), 0.609-0.709 (m, 4H).

MS (ESI) m/z: 394.3 [M+1]$^+$.

Example 48

Preparation of N-(6-cyclobutyl-9H-purine-2-yl)quinoline-6-amine

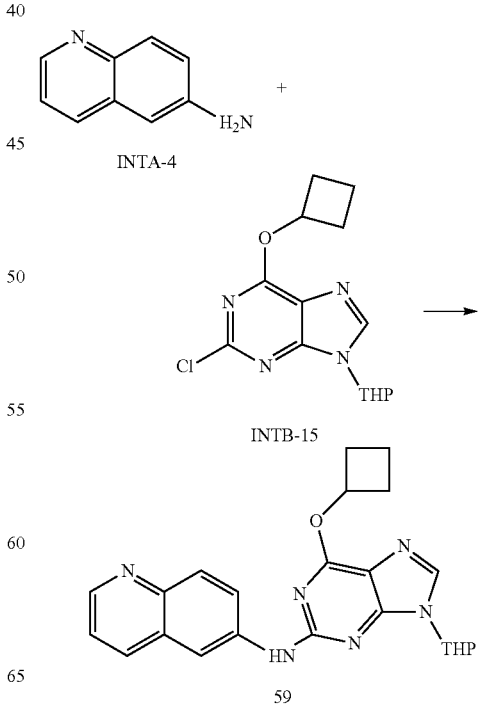

-continued

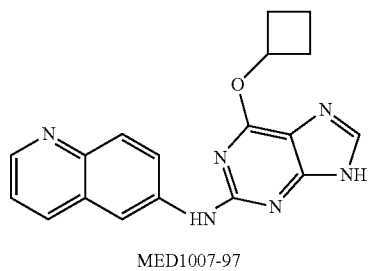

MED1007-97

The preparation method of the compound of the example includes the following steps:

1) Compound INTB-15 (200 mg, 0.65 mmol), palladium acetate (15 mg, 0.065 mmol), BINAP (45 mg, 0.065 mmol) and potassium phosphate (512 mg, 1.95 mmol) are added to compound INTA-4 (93 mg, 0.65 mmol) dissolved in toluene (20 mL), and stirred under reflux overnight to form a reaction mixture, cooled to room temperature, and ethyl acetate and water are added to the reaction mixture. to form an organic layer The organic layer is separated, dried with anhydrous sodium sulfate, filtrated, concentrated and purified by Pre-TLC (ethyl acetate:methanol=15:1) to obtain brown solid compound 59 (190 mg, yield: 70%).

2) Compound 59 (190 mg, 0.46 mmol) is dissolved in methanol (5 mL) and 4N hydrochloric acid methanol (5 mL), and stirred overnight at room temperature to form a reaction mixture, the reaction mixture is diluted with water, extracted with ethyl acetate, washed with sodium bicarbonate and brine to form an organic phase. The organic phase is dried with anhydrous sodium sulfate, concentrated to dryness and purified by Pre-TLC (dichloromethane:methanol=10:1) to obtain yellow solid MED1007-97 (70 mg, yield 46%).

Molecular formula: $C_{18}H_{16}N_6O$, Molecular weight: 332.36.

$^1$H-NMR (400 MHz, CD$_3$OD): δ 8.669 (d, J=2.4 Hz, 2H), 8.241 (d, J=8 Hz, 1H), 8.021 (s, 1H), 7.958 (m, 2H), 7.484 (m, 1H), 5.551 (m, 1H), 2.619 (m, 2H), 2.324 (m, 2H), 1.878 (m, 2H).

MS (ESI) m/z: 333.3 [M+1]$^+$.

Example 49

Preparation of N-(6-cyclobutyl-9H-purine-2-yl)-4-phenyl quinoline-6-amine

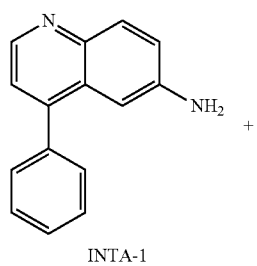

INTA-1

-continued

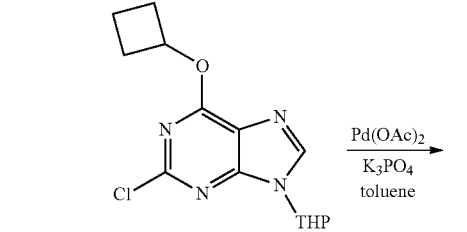

INTB-15

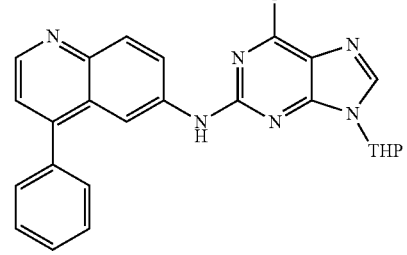

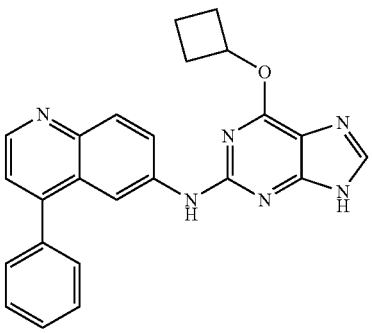

MED1007-98

The preparation method of the compound of the example includes the following steps:

1) Compound INTB-15 (200 mg, 0.487 mmol), palladium acetate (15 mg, 0.049 mmol), BINAP (45 mg, 0.049 mmol) and potassium phosphate (360 mg, 1.46 mmol) are added to Compound INTA-1 (142 mg, 0.487 mmol) is dissolved in toluene (3 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 60 (100 mg, yield 41.6%).

2) Compound 60 (100 mg, 0.2 mmol) is dissolved in dichloromethane (4 mL) and trifluoroacetic acid (1 mL), and stirred overnight at room temperature, concentrated to dryness and purified by Pre-TLC (dichloromethane:methanol=10:1) to obtain yellow solid compound MED1007-98 (50 mg, yield 61.3%).

Molecular formula: $C_{24}H_{21}N_7O$, Molecular weight: 408.

$^1$H-NMR (400 MHz, CD3OD): δ 8.718 (d, J=4.8 Hz, 1H), δ 8.509 (d, J=2.4 Hz, 1H), 7.967-8.108 (m, 3H), 7.560-7.682 (m, 5H), 7.425 (d, J=4.8 Hz, 1H), 4.830-4.866 (m, 1H), 2.309-2.372 (m, 2H), 2.105-2.155 (m, 2H), 1.619-1.811 (m, 2H).

MS (ESI) m/z: 409.5 [M+1]$^+$.

Example 50

Preparation of N6-(cyclopentyl methyl)-N2-(4-phenyl quinoline-6-yl)-9H-purine-2, 6-diamine

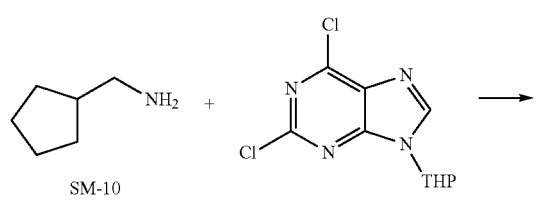

SM-10    2

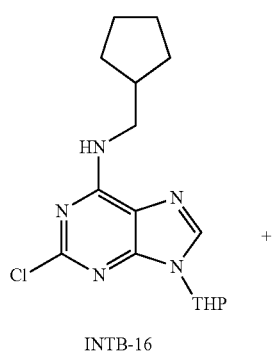

INTB-16

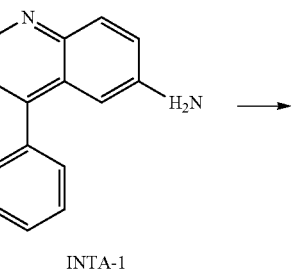

INTA-1

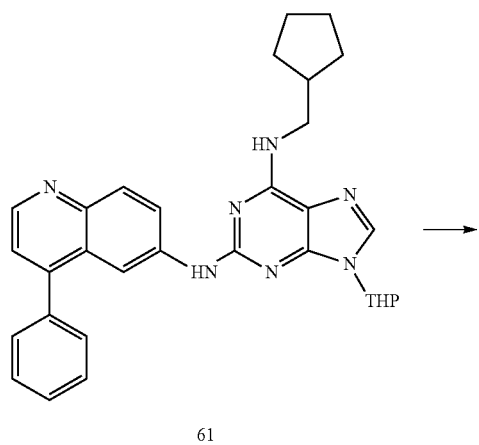

61

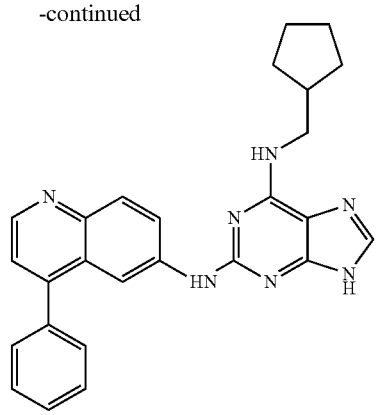

MED1007-99

The preparation method of the compound of the example includes the following steps:

1) DIPEA (900 mg, 6.95 mmol) is added in tetrahydrofuran (30 ml), compound SM-10 (375 mg, 2.78 mmol) and compound 2 (600 mg, 2.32 mmol) at room temperature, and stirred for 12 hours at temperature of 50° C., extracted with ethyl acetate, washed with water and brine, dried with sodium sulfate, filtrated and concentrated to obtain yellow solid compound INTB-16 (700 mg, yield 90%).

2) Compound INTB-16 (184 mg, 0.55 mmol), palladium acetate (20 mg, 0.09 mmol), BINAP (56 mg, 0.09 mmol) and potassium phosphate (328 mg, 1.35 mmol) are added to compound INTA-1 (100 mg, 0.45 mmol) dissolved in toluene (20 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 61 (90 mg, yield: 38%).

3) Compound 61 (90 mg, 0.17 mmol) is dissolved in methanol (5 mL) and 4N hydrochloric acid methanol (5 mL), and stirred overnight at room temperature to form a reaction mixture, the reaction mixture is diluted with water, extracted with ethyl acetate, and washed with sodium bicarbonate and brine to form an organic phase. The organic phase is dried with sodium sulfate, concentrated to dryness and purified by Pre-TLC (dichloromethane:methanol=10:1) to obtain yellow solid MED1007-99 (50 mg, yield 68%).

Molecular formula: $C_{26}H_{25}N_7$, Molecular weight: 435.52.

$^1$H-NMR (400 MHz, DMSO-d6): δ 10.319 (s, 1H), 9.109 (d, J=5.6 Hz, 1H), 8.997 (s, 1H), 8.882 (s, 1H), 8.544 (s, 2H), 8.393 (d, J=10 Hz, 1H), 7.900 (d, J=5.6 Hz, 1H), 7.679 (m, 5H), 3.092 (s, 2H), 2.049 (m, 1H), 1.671 (m, 2H), 1.491 (m, 4H), 1.167 (M, 2H).

MS (ESI) m/z: 436.5 [M+1]$^+$.

Example 51

Preparation of N6-isopropyl-N2-(4-phenyl quinoline-6-yl)-9H-purine-2, 6-diamine

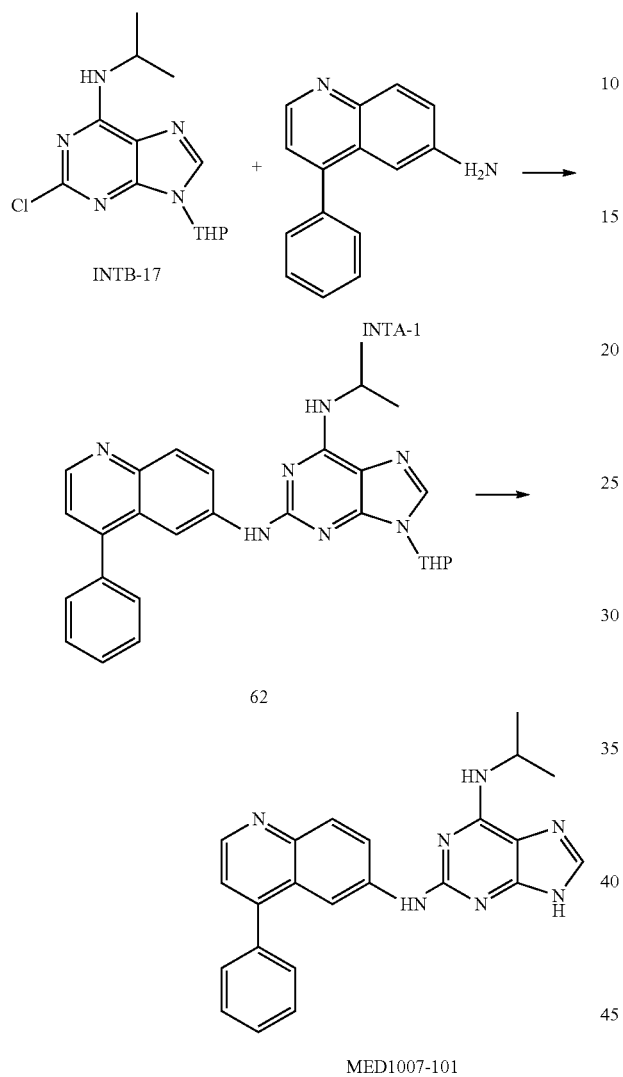

The preparation method of the compound of the example includes the following steps:

1) Compound INTB-17 (295 mg, 1 mmol), palladium acetate (45 mg, 0.2 mmol), BINAP (124 mg, 0.2 mmol) and potassium phosphate (630 mg, 3 mmol) are added to compound INTA-1 (220 mg, 1 mmol) dissolved in toluene (15 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 62 (300 mg, yield: 62%) will be obtained.

2) Compound 62 (300 mg, 0.62 mmol) is dissolved in methanol (10 mL) and 4N hydrochloric acid methanol (10 mL), and stirred overnight at room temperature to form a reaction mixture. The reaction mixture is filtered, the filter cake is dried under vacuum condition to obtain compound MED1007-101 (150 mg, yield 60%).

Molecular formula: $C_{23}H_{21}N_7$, Molecular weight: 395.46.
$^1$H-NMR (400 MHz, DMSO-d6): δ 10.427 (s, 1H), 9.119 (d, J=5.6 Hz, 1H), 9.026 (s, 1H), 8.920 (s, 1H), 8.591 (s, 1H), 8.514 (m, 2H), 7.991 (d, J=5.6 Hz, 1H), 7.741 (m, 5H), 3.651 (s, 1H), 1.071 (d, J=6.4 Hz, 6H).
MS (ESI) m/z: 396.4 [M+1]$^+$.

Example 52

Preparation of 4-phenyl-N-(6-(pyrrolidine-1-yl)-9H-purine-2-yl)quinoline-6-amine

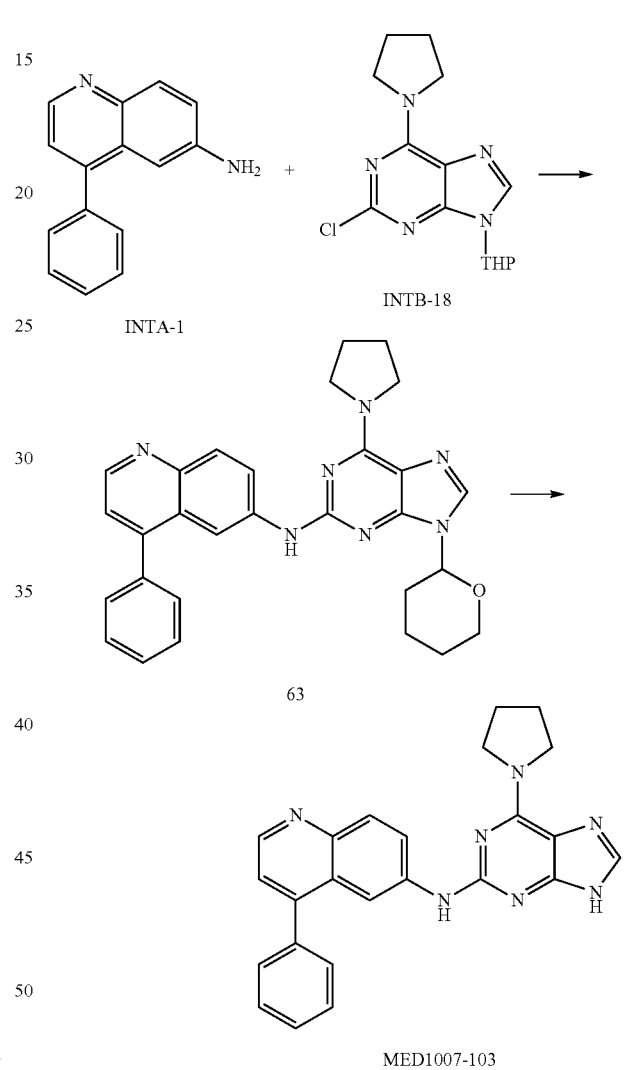

The preparation method of the compound of the example includes the following steps:

1) Compound INTA-1 (220 mg, 1 mmol), compound INTB-18 (307 mg, 1 mmol), palladium acetate (44.8 mg, 0.2 mmol), BINAP (124.4 mg, 0.2 mmol) and potassium phosphate (789 mg, 3 mmol) are dissolved in toluene (15 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=20:1) to obtain yellow solid compound 63 (80 mg, yield 47%).

2) Compound 63 (80 mg) is dissolved in methanol (10 mL) saturated with HCl, and stirred overnight at room temperature, concentrated to dryness and purified by Pre-HPLC to obtain yellow solid compound MED1007-103 (40 mg, yield 56%).

Molecular formula: $C_{24}H_{21}N_7S$, Molecular weight: 407.

$^1$H-NMR: 1H-NMR (400 MHz, DMSO 1.649-1.899 (m, 4H), 2.867 (t, 2H), 3.941 (s, 2H), 7.621-7.737 (m, 6H), 8.133 (s 1H), 8.244 (s, 2H), 8.766 (s, 1H), 8.985 (d, J=4.8 Hz, 1H), 9.940-9.948 (m, 1H)

MS (ESI) m/z: MS (ESI) m/z: 408 [M+1]+

Example 53

Preparation of N-(6-isopropoxy-9H-purine-2-yl) quinoline-6-amine

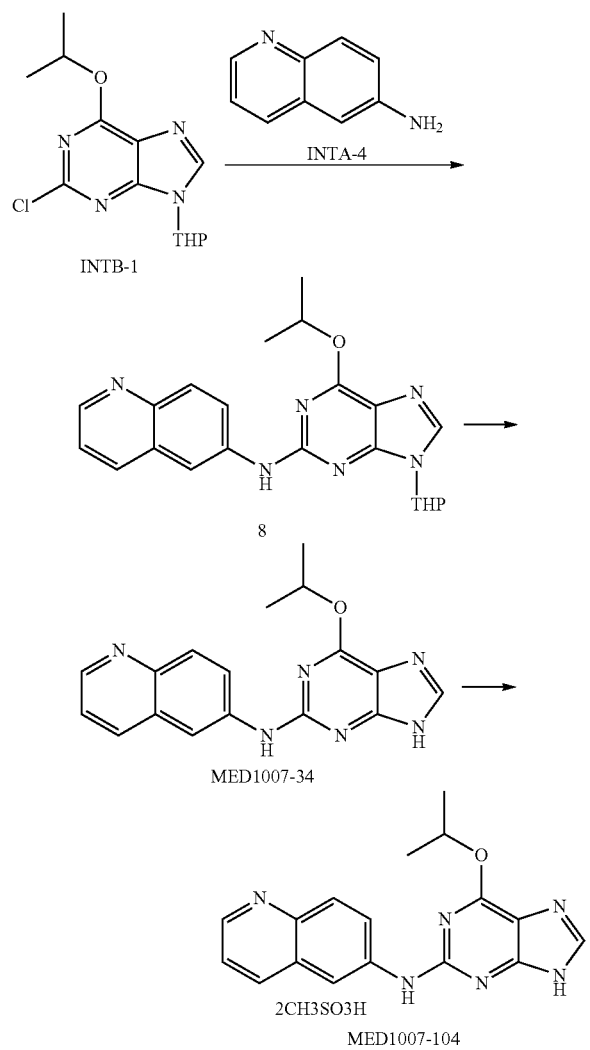

cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=20:1) to obtain yellow solid compound 8 (80 mg, yield 49%).

2) Compound 8 (80 mg) is dissolved in methanol (10 mL) saturated with hydrogen chloride, and stirred overnight at room temperature, concentrated to dryness and purified by Pre-HPLC to obtain yellow solid compound MED1007-34 (40 mg).

3) B is slowly added dropwise to compound MED1007-34 (40 mg) dissolved in ethanol and two drops of water and stirred at room temperature to form a reaction mixture. The reaction mixture is filtrated and concentrated to obtain yellow solid compound MED1007-104 (29 mg, yield 68%).

Molecular formula: $C_{24}H_{21}N_7S$, Molecular weight: 512.

$^1$H-NMR (400 MHz, DMSO 1.499 (d, J=6 Hz, 6H), 2.505 (m, 6H), 5.674 (t, 1H), 8.011 (dd, J=8.0 Hz, 1H), 8.217 (d, J=8.8 Hz, 1H), 8.327-8.351 (m, 1H), 8.749 (s, 1H), 8.900 (s, 1H), 8.977 (d, J=8.8 Hz 1H), 9.096 (d, J=4.8 Hz 1H), 10.396 (s, 1H)

MS (ESI) m/z: 321 [M+1]$^+$.

Example 54

Preparation of N-(6-(pentyl-3-yl oxyl)-9H-purine-2-yl)-4-phenyl quinoline-6-amine

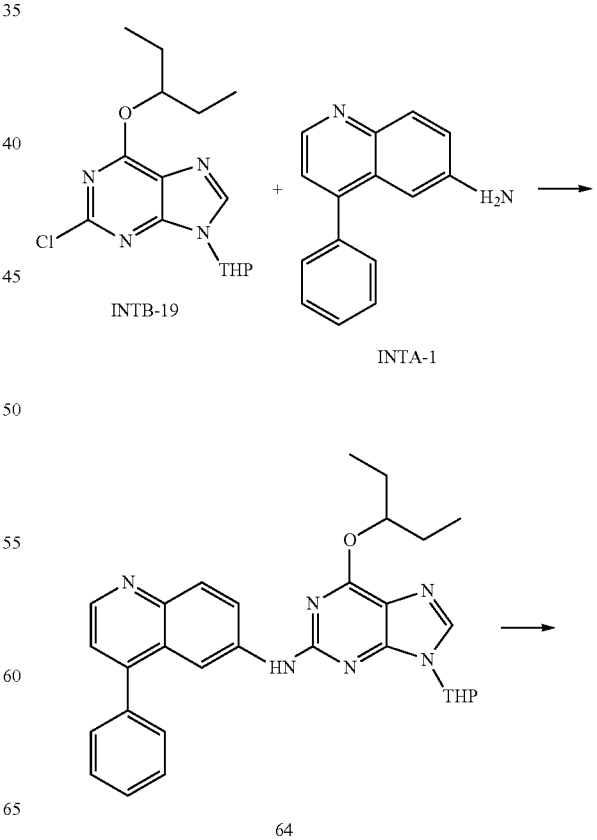

The preparation method of the compound of the example includes the following steps:

1) Compound INTA-4 (144 mg, 1 mmol), compound INTB-1 (296 mg, 1 mmol), palladium acetate (44.8 mg, 0.2 mmol), BINAP (124.4 mg, 0.2 mmol) and potassium phosphate (789 mg, 3 mmol) are dissolved in toluene (15 mL), and stirred under reflux overnight to form a reaction mixture,

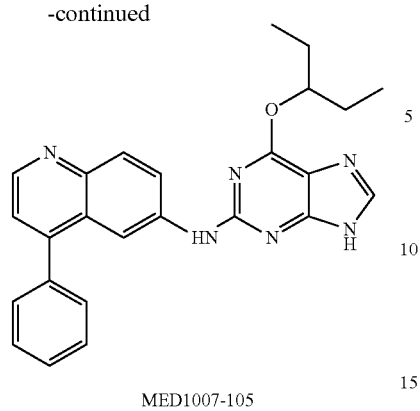

MED1007-105

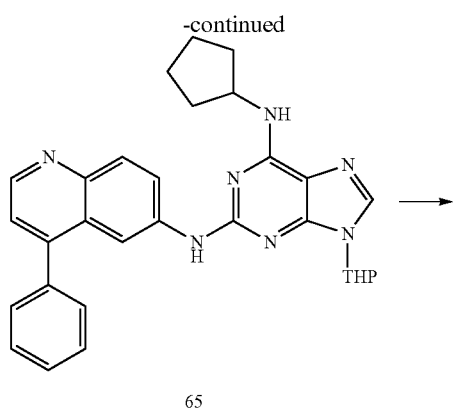

The preparation method of the compound of the example includes the following steps:

1) Compound INTB-19 (322 mg, 1 mmol), palladium acetate (45 mg, 0.2 mmol), BINAP (124 mg, 0.2 mmol) and potassium phosphate (630 mg, 3 mmol) are added to compound INTA-1 (220 mg, 1 mmol) dissolved in toluene (15 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 64 (280 mg, yield: 55%).

2) Compound 64 (280 mg, 0.55 mmol) is dissolved in methanol (10 mL) and 4N hydrochloric acid methanol (10 mL), and stirred overnight at room temperature to form a reaction mixture. The reaction mixture is filtered, the filter cake is dried under vacuum condition to obtain compound MED1007-105 (140 mg, yield 60%).

Molecular formula: $C_{25}H_{24}N_6O$, Molecular weight: 424.50.

$^1$H-NMR (400 MHz, DMSO-d6): δ 12.712 (s, 1H), 9.607 (s, 1H), 8.748 (d, J=4 Hz, 1H), 8.315 (d, J=8 Hz, 1H), 8.181 (s, 1H), 8.006 (m, 2H), 7.618 (m, 5H), 7.350 (d, J=4.8 Hz, 1H), 5.049 (m, 1H), 1.630 (m, 4H), 0.847 (m, 6H).

MS (ESI) m/z: 425.4 [M+1]$^+$.

Example 55

Preparation of N6-cyclopentyl-N2-(4-phenylquinoline-6-yl)-9H-purine-2, 6-diamine

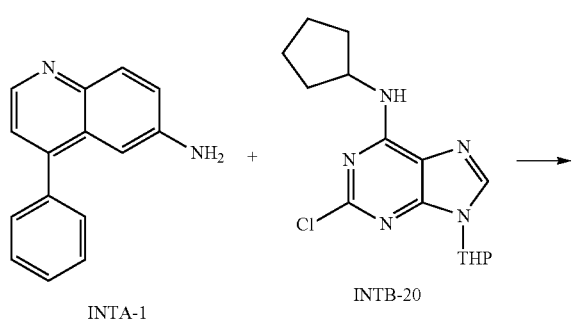

INTA-1      INTB-20

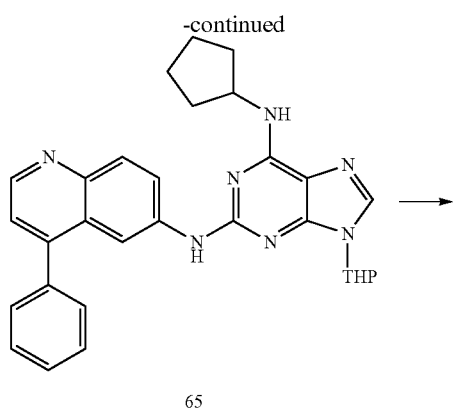

MED1007-106

The preparation method of the compound of the example includes the following steps:

1) Compound INTA-1 (220 mg, 1 mmol), compound INTB-20 (321 mg, 1 mmol), palladium acetate (44.8 mg, 0.2 mmol), BINAP (124.4 mg, 0.2 mmol) and potassium phosphate (789 mg, 3 mmol) are dissolved in toluene (15 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=20:1) to obtain yellow solid compound 65 (40 mg, yield 29%).

2) Compound 65 (40 mg) is dissolved in methanol (10 mL) saturated with hydrogen chloride, and stirred overnight at room temperature, concentrated to dryness and purified by Pre-HPLC to obtain yellow solid compound MED1007-106 (19 mg, yield 42%).

Molecular formula: $C_{24}H_{21}N_7S$, Molecular weight: 420.

$^1$H-NMR (400 MHz, DMSO-d6): δ 1.176-1.777 (m, 8H), 3.936-4.021 (m, 1H), 7.568-7.828 (m, 8H), 8.151 (d, J=8.8 Hz, 1H), 8.348-8.443 (m, 3H), 8.950 (d, J=4.8 Hz, 1H), 9.898 (s, 1H).

MS (ESI) m/z: 421 [M+1]$^+$.

Example 56

Preparation of N-(6-cyclohexyloxy-9H-purine-2-yl)-4-phenyl quinoline-6-amine

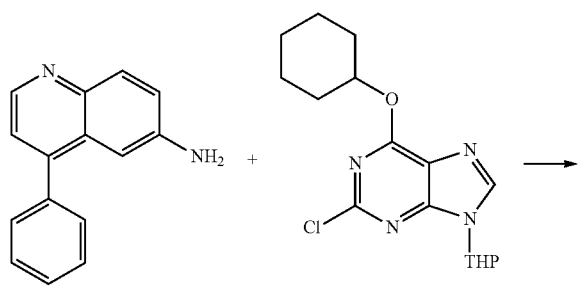

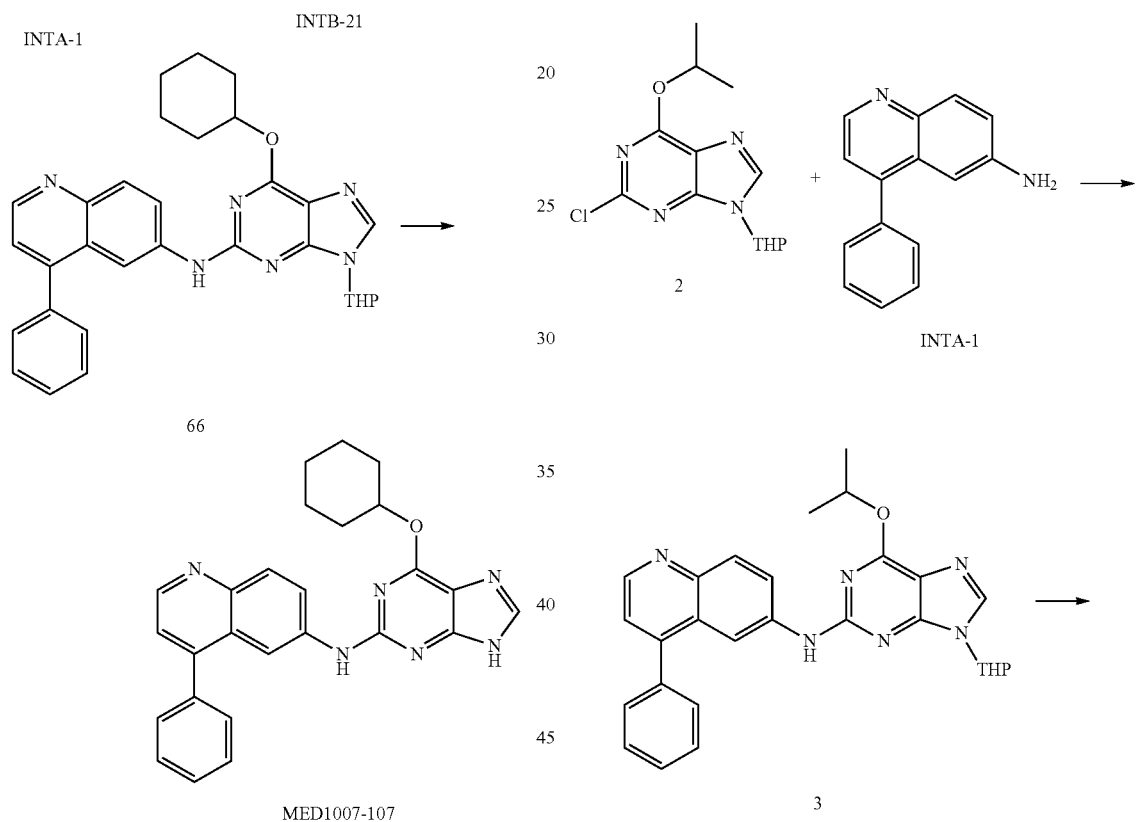

The preparation method of the compound of the example includes the following steps:

1) Compound INTA-1 (220 mg, 1 mmol), compound INTB-21 (420 mg, 1 mmol), palladium acetate (44.8 mg, 0.2 mmol), BINAP (124.4 mg, 0.2 mmol) and potassium phosphate (789 mg, 3 mmol) are dissolved in toluene (15 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=20:1) to obtain yellow solid compound 66 (100 mg, yield 49%).

2) Compound 66 (100 mg) is dissolved in methanol (10 mL) saturated with hydrogen chloride, and stirred overnight at room temperature, concentrated to dryness and purified by Pre-HPLC to obtain yellow solid compound MED1007-107 (60 mg, yield 58%).

Molecular formula: $C_{24}H_{21}N_7S$, Molecular weight: 436.

$^1$H-NMR (400 MHz, DMSO-d6): 1.181-1.986 (m, 10H), 5.139 (t, 1H), 7.585-7.675 (m, 6H), 8.136-8.325 (m, 2H), 8.510 (s, 1H), 8.532-8.542 (m, 1H), 8.926 (s, 1H), 9.861 (s, 1H).

MS (ESI) m/z: 437 [M+1]$^+$.

Example 57

Preparation of N-(6-isopropoxy-9H-purine-2-yl)-4-phenyl quinoline-6-amine dihydrate di-methanesulfonate

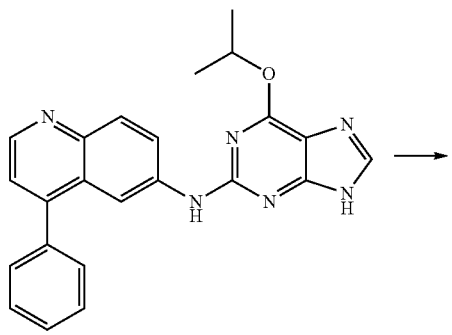

-continued

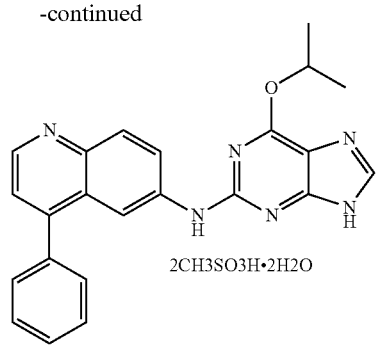

MED1007-108

The preparation method of the compound of the example includes the following steps:

1) Compound 2 (296 mg, 1 mmol), palladium acetate (44.8 mg, 0.2 mmol), BINAP (124.4 mg, 0.2 mmol) and potassium phosphate (636 mg, 3 mmol) are added to compound INTA-1 (220 mg, 1 mmol) dissolved in toluene (10 mL), and stirred under reflux overnight to form a reaction mixture, cooled to room temperature, and ethyl acetate and water are added to the reaction mixture to form an organic layer. The organic layer is separated, dried by anhydrous sodium sulfate, filtrated, concentrated and purified by Pre-TLC (ethyl acetate:methanol=15:1) to obtain brown solid compound 3 (400 mg, yield 83%).

2) Compound 3 (200 mg, 0.48 mmol) is dissolved in methanol (5 mL) and 4N hydrochloric acid methanol (5 mL), and stirred overnight at room temperature to form a reaction mixture, the reaction mixture is diluted with water, extracted with ethyl acetate, and washed with sodium bicarbonate and brine to form an organic phase. The organic phase is dried with anhydrous sodium sulfate, concentrated to dryness, and then purified by Pre-TLC (dichloromethane:methanol=10:1) to obtain brown solid MED1007-51 (140 mg, yield 73%).

3) Methanesulfonic acid (152 mg, 1.69 mmol) is added to compound MED1007-51 (140 mg, 0.35 mmol) dissolved in ethanol (5 mL) and water at temperature of 0° C., and stirred overnight at room temperature to form a reaction mixture. The reaction mixture is filtered, the filter cake is dried under vacuum condition to obtain compound MED1007-108 (100 mg, yield 45%).

Molecular formula: $C_{23}H_{20}N_6O \cdot 2CH_3SO_3H \cdot 2H_2O$, Molecular weight: 396.44.

$^1$H-NMR (400 MHz, DMSO-d6): δ 9.193 (s, 1H), 9.046 (d, J=5.6 Hz, 1H), 8.679 (m, 2H), 8.304 (d, J=10 Hz, 1H), 7.988 (d, J=6 Hz, 1H), 7.745 (m, 5H), 5.355 (m, 1H), 2.727 (s, 6H), 1.401 (d, J=6 Hz, 6H).

MS (ESI) m/z: 397.2 [M+1]$^+$.

Example 58

Preparation of N-(6-morpholine-9H-purine-2-yl)-4-phenyl quinoline-6-amine

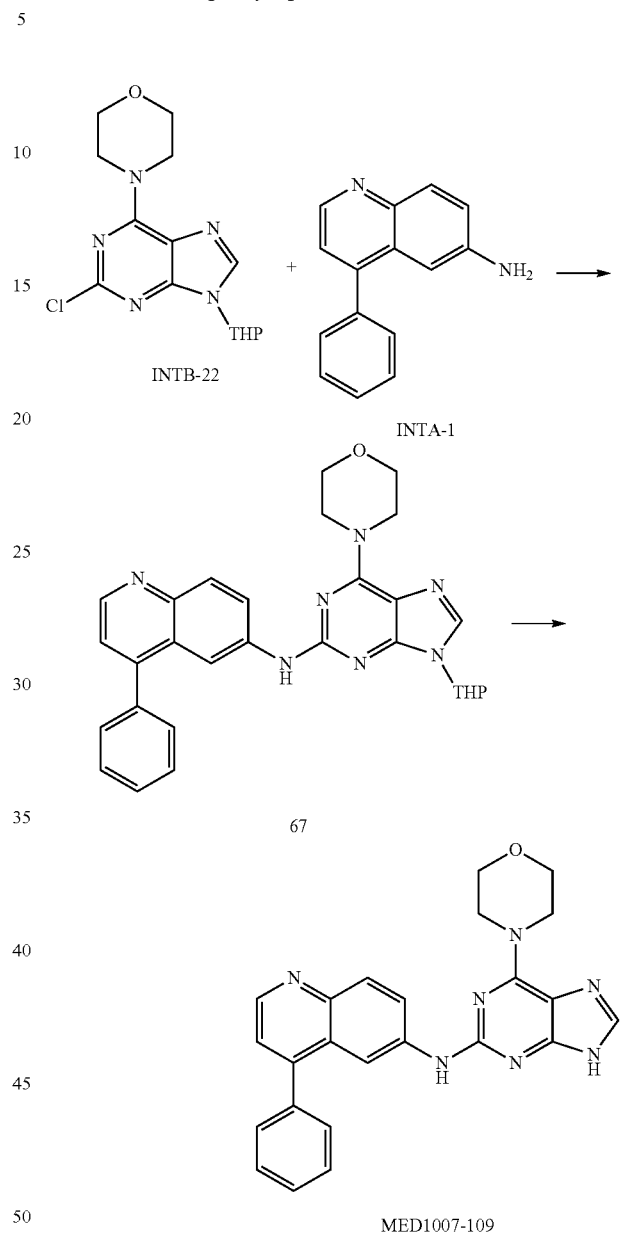

The preparation method of the compound of the example includes the following steps:

1) Compound INTB-22 (146 mg, 0.45 mmol), palladium acetate (20 mg, 0.1 mmol), BINAP (56 mg, 0.1 mmol) and potassium phosphate (355 mg, 1.35 mmol) are added to compound INTA-1 (100 mg, 45 mmol) dissolved in toluene (10 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 67 (180 mg, yield: 78%).

2) Compound 67 (180 mg, 0.35 mmol) is dissolved in methanol (5 mL) and 4N hydrochloric acid methanol (5 mL), and stirred overnight at room temperature to form a reaction mixture. The reaction mixture is diluted water, extracted with ethyl acetate, washed with sodium bicarbonate and brine to form an organic phase. The organic phase is dried with sodium sulfate, concentrated to dryness and purified by Pre-TLC (dichloromethane:methanol=10:1) to obtain yellow solid compound MED1007-109 (100 mg, yield 66%).

Molecular formula: $C_{24}H_{21}N_7O$, Molecular weight: 423.47.

1H-NMR (400 MHz, DMSO-d6): δ 10.077 (b, 1H), 9.067 (d, J=2 Hz, 1H), 8.566 (s, 1H), 8.466 (s, 2H), 8.183 (b, 1H), 7.887 (d, J=5.6 Hz, 1H), 7.693 (m, 5H), 3.863 (b, 4H), 3.587 (d, J=4 Hz, 4H)

MS (ESI) m/z: 424.4 [M+1]+

Example 59

Preparation of N-(6-morpholine-9H-purine-2-yl)-4-phenyl quinoline-6-amine dihydrate di-methanesulfonate

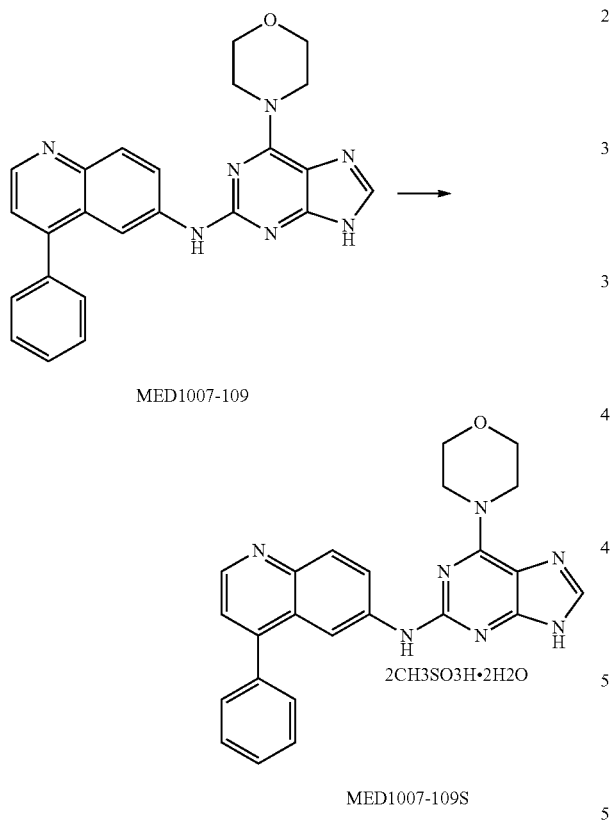

The preparation method of the compound of the present example includes the following steps:

Methanesulfonic acid (40 mg, 0.42 mmol) is added to compound MED1007-109 (60 mg, 0.14 mmol) dissolved in ethanol (5 mL) and water at the temperature of 0° C., and stirred overnight at room temperature to form a reaction mixture. The reaction mixture is filtered, the filter cake is dried under vacuum condition to obtain compound MED1007-109S (40 mg, yield 44%).

Molecular formula: $C_{24}H_{21}N_7O$ $2CH_3SO_3H.2H_2O$, Molecular weight: 423.47.

¹H-NMR (400 MHz, DMSO-d6): δ 9.083 (d, J=5.6 Hz, 1H), 8.671 (d, J=2.4 Hz, 1H), 8.473 (m, 2H), 8.325 (d, J=9.2 Hz, 1H), 8.000 (d, J=5.6 Hz, 1H), 7.755 (m, 5H), 3.894 (s, 4H), 3.710 (m, 4H), 2.746 (s, 6H).

MS (ESI) m/z: 424.5 [M+1]+

Example 60

Preparation of 2-(4-phenyl quinoline-6-yl amino)-9H-purine-6-ol

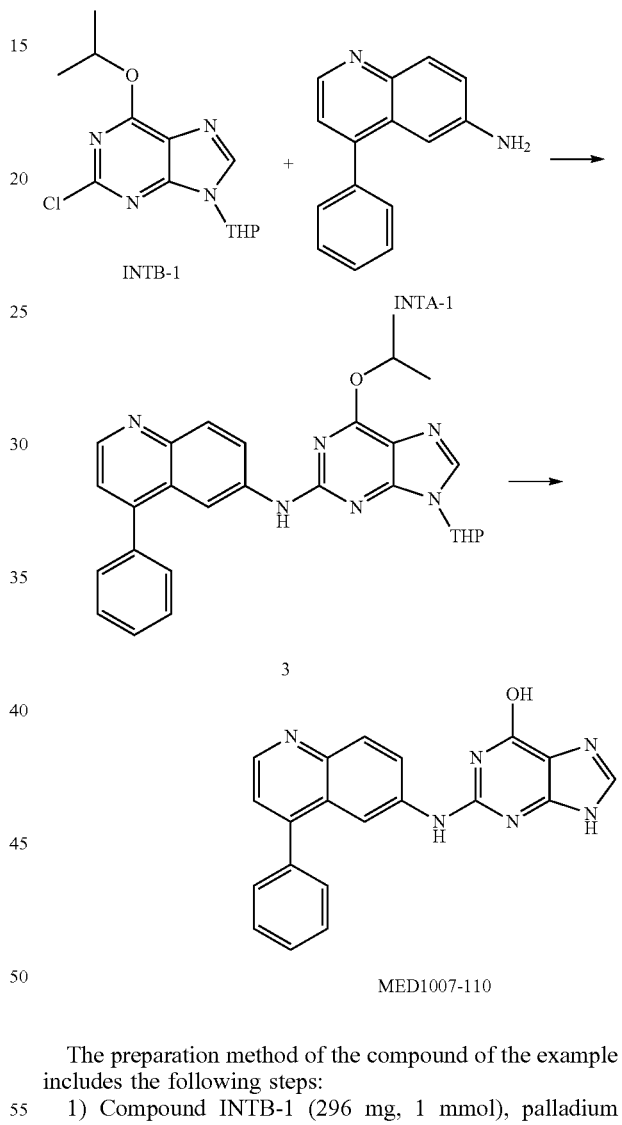

The preparation method of the compound of the example includes the following steps:

1) Compound INTB-1 (296 mg, 1 mmol), palladium acetate (44.8 mg, 0.2 mmol), BINAP (124.4 mg, 0.2 mmol) and potassium phosphate (636 mg, 3 mmol) are added to compound INTA-1 (220 mg, 1 mmol) dissolved in toluene (10 mL), and stirred under reflux overnight to form a reaction mixture, cooled to room temperature, and ethyl acetate and water are added to the reaction mixture to form an organic layer. The organic layer is separated, dried with anhydrous sodium sulfate, filtrated, concentrated and purified by Pre-TLC (ethyl acetate:methanol=15:1) to obtain brown solid compound 3 (400 mg, yield: 83%).

2) Trifluoroacetic acid (1.5 mL) is added to compound 3 (200 mg, 0.42 mmol) dissolved in dichloromethane (5 mL)

at 0° C., and stirred for 30 hours at 35° C. to form a reaction mixture. The reaction mixture is diluted with water, extracted with ethyl acetate, washed with sodium bicarbonate and brine to form an organic phase. The organic phase is dried with sodium sulfate, concentrated to dryness and purified by Pre-TLC (dichloromethane:methanol=10:1) to obtain yellow solid compound MED1007-110 (120 mg, yield 80%).

Molecular formula: $C_{20}H_{14}N_6O$, Molecular weight: 354.36.

$^1$H-NMR (400 MHz, DMSO-d6): δ 12.551 (b, 1H), 10.822 (b, 1H), 9.559 (b, 1H), 8.818 (d, J=3.2 Hz, 1H), 8.090 (m, 9H), 7.392 (m, 1H).

MS (ESI) m/z: 355.4 $[M+1]^+$.

Example 61

Study on Antitumor Cell Proliferation In Vitro of the Compounds of Present Invention The half inhibitory concentration IC50 of proliferation of three kinds of tumor cell strain (U87MG, PC-3, BT474) for 12 candidate compounds of the present invention is detected by CCK-8 detection kits.
Materials and Methods
Cell Strain:
U87MG human glioblastoma Multiforme cell strain (cell bank of Chinese Academy of Sciences)
PC-3 human prostate cancer cell strain (cell bank of Chinese Academy of Sciences)
BT474 human breast cancer cell strain (cell bank of Chinese Academy of Sciences) Reagents and materials:
Cell Counting Kit-8 (Cat#CK04-13, Dojindo)
96 well culture plates (Cat#3599, Corning Costar)
Fetal calf serum (Cat#10099-141, GIBCO)
Culture medium (Invitrogen)
Table model microplate reader SpectraMax M5 Microplate Reader (Molecular Devices)
Candidate compounds: provided by chemical department of Medicilon Experimental procedure
3.1 Reagent Preparation
Culture medium preparation

| Cell line | Culture medium |
|---|---|
| U87MG | EMEM + 1 mM sodium pyruvate + 1.5 g/L NaHCO3 + 10% FBS |
| PC-3 | F12 K + 10% FBS |
| BT474 | Hybri care + 10% FBS |

The studied compounds are dissolved by DMSO to make the final concentration 10 mM.
3.2 Cell Culture
  a) Collecting the cells in logarithmic phase, counting, and resuspending the cells with complete medium.
  b) Adjusting the concentration of cells to a suitable concentration, inoculating in 96 well plates, each well is inoculated to 100 µl cell suspension.
  c) incubating cells for 24 hours in a 5% CO2 incubator at temperature of 37° C., under the condition of 100% relative humidity.
3.3 IC50 Experiment
  a) The cells in logarithmic phase is collected, counted, resuspended with complete medium. The concentration of cells is adjusted to a suitable concentration (determined in accordance with the optimizable test results of cell density), and the cells is inoculated in 96 well plates, wherein each well is inoculated 100 µl cell suspension, Cells are incubated for 24 hours in 5% CO2 incubator at temperature of 37° C. under the condition of 100% relative humidity.
  b) The test compounds are diluted to 500 µM with culture medium, then diluted in series eight times. Cells are added as 25 µl/well. The final concentrations of the compounds are diluted from 100 µM to 0 µM, with 4 times dilution, and there are a total of 10 concentration points.
  c) Cells are incubated for 72 hours in 5% CO2 incubator at temperature of 37° C. under the condition of 100% relative humidity.
  d) The culture medium is aspirated and discarded, and complete medium containing 10% CCK-8 is incubated in a incubator at 37° C. for 2~4 hours.
  e) After shocking gently, the absorbance of the culture medium is measured at 450 nm wavelength on SpectraMax M5 Microplate Reader, with the absorbance at 650 nm as reference, to calculate the inhibition rate.
3.4 Data Processing
The tumor cell growth inhibition rate %=$[(A_c-A_s)/(A_c-A_b)] \times 100\%$ Wherein, $A_s$: OA of sample (cell+CCK-8+test compound);
  $A_c$: OA of negative control (cell+CCK-8+DMSO);
  $A_b$: OA of positive control (culture medium+CCK-8+DMSO);
Experimental Results Compounds of MED1007 series include-51, -63, -91, -101, -104, -105, -108, -109s, -115, XC-302 and Wortmannin. As an effect for U87MG, PC-3 & BT474 cytotoxic, the IC50s (µM) results are shown in table 1.

TABLE 1

|  | PC-3 cells | U-87MG cells | BT-474 cells |
|---|---|---|---|
| MED1007-51 | 0.0662 (1$^{st}$ test) | 15.65 (1$^{st}$ test) | 0.0814 (1$^{st}$ test) |
|  | 0.1729 (2$^{nd}$ test) | 4.424 (2$^{nd}$ test) | 0.1138 (2$^{nd}$ test) |
| MED1007-91 | 0.6542 | 8.150 | 0.5229 |
| MED1007-101 | 0.6162 | 8.604 | 0.4409 |
| MED1007-104 | 1.696 | 18.11 | 1.362 |
| MED1007-105 | 1.025 | 40.95 | 0.4202 |
| MED1007-108 | 0.0716 (1$^{st}$ test) | 12.33 (1$^{st}$ test) | 0.0630 (1$^{st}$ test) |
|  | 0.1131 (2$^{nd}$ test) | 5.467 (2$^{nd}$ test) | 0.0350 (2$^{nd}$ test) |
| MED1007-109S | 0.6965 | 18.30 | 0.6123 |
| MED1007-115 | 1.567 | 7.356 | 1.949 |
| XC-302 | 14.96 | 17.80 | 5.874 |
| Wortmannin | 21.57 | Re-test needed | 5.210 |

It can be seen from Table 1 that compounds of the present invention have the effect of inhibiting tumor cell proliferation Example 62

Study on Inhibitory Activity of Compounds of Present Invention to PDGFR β Enzyme Inhibition efficiency is detected, the Staurosporine is choosed as a positive control drug to study the inhibitory activity of test compounds of MED1007 series to PDGFRβ enzyme at the concentration of 10 µM and 1 µM, wherein, each study group is detected by setting triplicate wells.

The half inhibitory concentration of staurosporine to PDGFR β and the inhibition rate of ten test compounds to the enzyme activity of PDGFR β at 10 µM and 1 µM is detected by HTRF kinEASE TK kit. The experimental results are shown in Table 3: The inhibition rate of test compounds to PDGFR β at 10 μM and 1 μM.

Materials and Equipments

2104 EnVision® Multilabel Reader (PerkinElmer)
OptiPlate-384, White Opaque 384-well MicroPlate (Cat.6007290, PerkinElmer)
HTRF kinEASE TK (Cat.62TK0PEC, Cisbio)
PDGFR β enzyme (Cat.P3082, Invitrogen)
ATP 10 mM (Cat.PV3227, Invitrogen)
DTT 1 M (Cat.D5545, Sigma)
MgCl$_2$ 1 M (Cat.M8266 Sigma)
MnCl$_2$ 1 M
Detecting Compounds Experimental Procedure 1. Reagent Preparation

TABLE 2

|  |  | PDGFR β |
|---|---|---|
| Concentration of enzyme | Final concentration of enzyme reaction steps (10 μL) | 0.2 ng/well |
| ATP (μM) |  | 30 μM |
| TK-Substrate |  | 1 μM |
| Time of enzyme reaction |  | 10 min |
| Sa-XL665 | Final concentration in complete reaction (20 μL) | 125 nM |
| TK-Ab-Cryptate |  | 1:100 dilution |

1×PDGFR β Enzymatic Buffer:

1 mL 1×Kinase Buffer 中含有 200 μL 5×Enzyme buffer, 5 μM MgCl$_2$, 1 μL 1M DTT, 1 μL 1M MnCl$_2$, 20 μL 2500 nM SEB, 773 μL ddH$_2$O.

1 mL 1×Kinase Buffer includes 200 μL 5×Enzyme buffer, 5 μL 1M MgCl$_2$, 1 μL 1M DTT, 1 μL 1M MnCl$_2$, 20 μL 2500 nM SEB, 773 μL ddH$_2$O.

Mixed solution of 2.5×TK-Substrate/ATP

Concentrations of TK-Substrate and ATP are shown in Table 2.

TK-Substrate and ATP are diluted to 2.5 times of reaction concentration with 1×PDGFR β Kinase Buffer.

5×Enzyme working solution

5×PDGFR β enzyme working solution is prepared with 1×PDGFR β kinase buffer.

4×Sa-XL665 Working Solution

Concentration of Sa-XL665 in reaction is shown in Table 1. 4×Sa-XL665 working solution is prepared with Detection Buffer.

4×TK-Ab-Cryptate Working Solution

TK-Ab-Cryptate is diluted 100 times with Detection Buffer to use as working solution.

Experimental results are shown in Table 3.

TABLE 3

|  | 10 μM | | 1 μM | |
|---|---|---|---|---|
|  | Inhibition rate % | SD | Inhibition rate % | SD |
| MED1007-15 | 93.52 | 2.99 | 31.22 | 10.80 |
| MED1007-31 | 26.16 | 8.17 | 13.84 | 5.70 |
| MED1007-32 | 24.48 | 3.39 | 9.16 | 7.71 |
| MED1007-33 | 25.64 | 5.41 | 4.71 | 2.98 |
| MED1007-34 | 98.81 | 0.46 | 53.82 | 0.58 |
| MED1007-35 | 98.99 | 0.27 | 54.84 | 4.93 |
| MED1007-51 | 33.56 | 6.25 | 11.90 | 8.34 |
| MED1007-54 | 43.66 | 9.04 | 7.30 | 6.78 |
| MED1007-58 | 29.50 | 5.74 | 3.93 | 5.03 |
| MED1007-59 | 0.93 | 5.95 | 4.39 | 7.18 |
| MED1007-60 | 10.59 | 8.43 | −0.63 | 9.55 |
| MED1007-61 | 55.00 | 6.51 | 4.72 | 15.97 |
| MED1007-63 | 28.00 | 3.86 | −0.31 | 10.29 |
| MED1007-64 | 20.07 | 5.02 | −3.26 | 16.10 |
| MED1007-65 | 13.99 | 7.93 | 21.49 | 4.50 |
| MED1007-66 | 14.49 | 6.06 | 16.99 | 5.66 |
| MED1007-67 | 18.74 | 9.64 | 22.24 | 2.60 |
| MED1007-68 | 11.74 | 13.32 | 18.74 | 2.41 |
| MED1007-69 | 31.76 | 3.88 | 11.74 | 19.27 |
| MED1007-70 | 73.01 | 1.02 | 33.37 | 3.77 |
| MED1007-71 | 4.50 | 15.44 | 9.74 | 15.37 |
| MED1007-72 | 2.50 | 8.69 | 7.25 | 20.83 |
| MED1007-73 | 35.03 | 19.70 | 16.99 | 12.72 |
| MED1007-75 | 8.74 | 7.90 | 13.24 | 9.54 |
| MED1007-83 | 7.60 | 9.50 | 4.50 | 2.74 |
| MED1007-84 | 13.42 | 3.14 | −8.59 | 1.15 |
| MED1007-85 | 29.83 | 9.04 | −3.44 | 7.56 |
| MED1007-86 | −3.13 | 5.06 | −5.49 | 7.58 |
| MED1007-87 | −4.13 | 2.09 | −7.60 | 6.81 |
| MED1007-88 | 2.89 | 3.14 | −5.37 | 8.17 |
| MED1007-91 | 13.82 | 5.30 | −10.96 | 8.66 |
| MED1007-97 | 99.45 | 0.62 | 98.42 | 0.98 |
| MED1007-98 | 37.83 | 1.68 | 38.13 | 9.81 |
| MED1007-99 | 9.88 | 5.88 | 33.06 | 6.25 |
| Staurosporine | 98.52 | 0.84 | 99.82 | 2.44 |
| XC-302 | 96.53 | 1.31 | 51.15 | 5.21 |

It can be seen from Table 3 that, the compounds of present invention have the role of inhibiting PDGFR β enzyme.

Example 63

Study on the Inhibitory Activity of Compounds of Present Invention to the Phosphorylation Level of PC-3 Cell Akt (Ser473)

The inhibitory activity of the compounds of present invention to the phosphorylation level of PC-3 cell Akt (Ser473) is studied by using Cisbio HTRF phospho Akt (Ser473) cell-based assay test kit.

Materials and Methods

Cell strain: PC-3 prostate cancer cells line (cell bank of Chinese Academy of Sciences) is cultured by using culture medium (F12K+10% FBS).

Reagents and Consumables

2104 EnVision® Multilabel Reader (PerkinElmer)
OptiPlate-384, White Opaque Low Volume 384-well MicroPlate (Cat.3674, CORNING)
HTRF Phospho Akt (Ser473) cell-based assay kit (Cat.64AKSPEG, 500test, CISBIO)
96 well culture plate (Cat#3599, Corning Costar)
fetal calf serum (Cat#10099-141, GIBCO)
F12K culture medium (Invitrogen)
hEGF (Cat.9644-0.2 mg, SIGMA)

Experimental Steps 3.1 Reagent Preparation a) Preparation of Irritant:

hEGF is prepared as stock solution of 100 ug/ml with 10 mM acetic acid, and the stock solution is diluted to 200 ng/ml with serum-free medium, added 50 ul to each well to be stimulated.

b) Preparation of Complete Lysate

4×Lysis Buffer is diluted 4 times with ddH$_2$O to prepare 1×Lysis Buffer.

100×Blocking Reagent is diluted 100 times with 1×Lysis Buffer.

c) Preparation of Detection Liquid

20×Anti-Phospho-Akt is diluted 20 times with Detection Buffer.

20×Anti-Akt is diluted 20 times with Detection Buffer.

d) Preparation of Test Compounds

The compounds are diluted with DMSO, and the working concentration of compounds is 100 times of detection concentration.

Experimental Methods

Cell Culture

Cells in logarithmic growth phase are collected, counted, and resuspended with complete culture medium;

The cell concentration is adjusted to appropriate concentration, and cell suspension is inoculated into 96 well plates at 50 μl per well;

Cells are incubated for more than 4 h in the 5% $CO_2$ incubator at temperature of 37° C., relative humidity of 100%;

Cell plate is removed from the incubator. The cell suspension is aspirated gently, and 50 ul serum-free F12K medium is quickly added, then the cell plate is placed into the incubator to culture overnight.

Medicate Treatment

The compounds are diluted in a linear gradient with DMSO.

0.5 ul compounds is added into the test well, mixed on oscillators, and incubated at room temperature for 2 hours.

Activating Stimulus Treatments

Proportioned hEGF solution is added to test well at 50 μl per well, and the final concentration is 100 ng/ml. serum-free medium is added into The negative control well at 50 μl per well.

The solution is mixed on oscillator and incubated at room temperature for 2 hours.

Lysis of Cells:

The liquid in 96 well plates is aspirated by multichannel pipette or the supernatant is discarded gently. The proportioned complete lysate is added quickly at 50 μl per well.

The solution is mixed on oscillator and lysed at room temperature for 30 min.

Transferring Feeding

16 μl cell lysate is transferred from the 96 well plates to white low volume 384 well plates, and the proportioned two pairs of detection antibody are added. The solution is mixed on oscillator, and incubated at room temperature for 4 hours to detect the readings. The experimental results are shown in Table 4.

TABLE 4

| Compounds | IC50 (nM) |
| --- | --- |
| MED1007-31 | 111.5 |
| MED1007-35 | 74.50 |
| MED1007-46 | 261.4 |
| MED1007-51 | 1.140 (1$^{st}$ test); 0.6831 (2$^{nd}$ test) |
| MED1007-63 | 62.22 |
| MED1007-91 | 73.96 |
| MED1007-101 | 66.96 |
| MED1007-103 | 276.4 |
| MED1007-108 | 3.827 (1$^{st}$ test); 6.513 (2$^{nd}$ test) |
| MED1007-109S | 116.4 |
| MED1007-115 | 259.5 |
| XC-302 | 10.05 (1$^{st}$ test); 33.60 (2$^{nd}$ test) |
| Wortmannin | 7.406 |

It can be seen from Table 4 that the compounds of present invention have the inhibitory effects to phosphorylation levels of PC-3 cells Akt (Ser473), especially MED1007 and MED1007-108-51.

Example 64

Study on Inhibitory Activity of the Compounds of Present Invention to PI 3κα, PI3κδ and PI3κγ

Study on the inhibitory activity of the compounds of present invention to PI 3κα, PI3κδ and PI3κγ. Two or three concentrations of the compounds are selected to preliminary screening to calculate respectively the activity inhibition rate of the compounds of corresponding concentrations to enzyme, then the compounds with better activity are selected by preliminary screening for IC50 test.

Materials and Equipments

EnVision Multilabel Plate Reader (PerkinElmer)

The 384-well opaque black board (Cat.6007279, PerkinElmer)

PI 3-Kinase (human) HTRF™ Assay kit (Cat.33-017, Millipore)

4× Reaction Buffer (Cat.33-002, Millipore)

PIP2 1 mM (Cat.33-004, Millipore)

Stop A (Cat.33-006, Millipore)

Stop B (Cat.33-008, Millipore)

DM A (Cat.33-010, Millipore)

DM B (Cat.33-012, Millipore)

DM C (Cat.33-014, Millipore)

PI 3k γ (Biology, Medicilon)

PI 3k α (Cat.14-602, Millipore)

PI 3k δ (Cat.14-604, Millipore)

ATP 10 mM (Cat. PV3227, Invitrogen)

DTT 1M (cat. D5545, Sigma)

Test Compounds

Reagents Preparation 1.33× Reaction Buffer

4× Reaction Buffer (Cat.33-002, Millipore) is diluted with ddH2O to 1.33×, and 1M DTT is added to make the final concentration as 6.67 mM. For example, 10 μL DTT is added into 500 μL 4× Reaction Buffer, and water is added to 1.5 mL.

4× Compound Working Liquid

The Test compounds are dissolved with DMSO to 1 mM as storage liquid. 2 μL of each of storage liquid is added into 48 μL ddH$_2$O, to obtain the 40 μM compounds solution containing 4% DMSO. After mixing, 3 μL of each of the solution is added into 27 μL 4% DMSO (in ddH$_2$O) to obtain the 4 μM compounds solution. 5 μL of each dilute solution is added into 384-well plates, then the final concentration of the compounds in the 20 μL final kinase reaction system is 10 μM and 1 μM respectively contained 1% DMSO. The dilution methods of compounds are similar to the preliminary screening in IC50 test.

2×PIP2 Working Fluid

2×PIP2 working fluid is prepared with 1.33× reaction buffer to the final concentration of 20 μM.

2×PIP2/Kinase Working Solution

The concentration optimization of two enzymes has been completed in the previous work, The screening concentration of PI 3k γ kinase: 80 ng/well, The screening concentration of PI 3k α kinase: 8 ng/well, The screening concentration of PI 3k δ kinase: 2 ng/well, Kinase is diluted with 2×PIP2 operating fluid, the concentration of kinase operating fluid is 2 times of screening concentration.

No contrast kinase (considered as 100% inhibition)
Namely 2×PIP2 working solution.
4×ATP working solution
10 mM ATP is diluted with 1.33× reaction buffer to 400 μM. The concentration of ATP is 100 μM in 20 μL kinase reaction system.
Stop Solution
Stop A and Stop B are mixed according to the proportion of 3:1, and are placed for 2 hours at room temperature to obtain the stop solution available.
Detection Solution
DM C, DM A and DM B are mixed according to the proportion of 18:1:1, and are placed for 2 hours at room temperature to obtain the detection solution available.
Experimental Results
The inhibition rate of the test compounds to PI3K alpha at 10 μM and 1 μM, can be seen in Table 5. The inhibition rate of the determining compounds to PI3K gamma at 10 μM and 1 μM. Please refer to Table 6. The inhibition rate of the determining compounds to PI3K delta at 10 μM and 1 μM. Please refer to Table 7~8.

TABLE 5

Inhibition rate of the compounds of the present invention to PI3K α

|  | 10 μM | | 1 μM | |
|---|---|---|---|---|
|  | % Inhibition Rate | SD | % Inhibition Rate | SD |
| MED1007-65 | 10.16 | 3.24 | 0.69 | 3.33 |
| MED1007-66 | -4.35 | 3.44 | -2.28 | 2.60 |
| MED1007-67 | 37.24 | 5.99 | 3.77 | 1.27 |
| MED1007-68 | 51.93 | 7.89 | 7.74 | 5.81 |
| MED1007-69 | 78.19 | 2.00 | 38.81 | 1.27 |
| MED1007-70 | 62.53 | 13.41 | 26.60 | 3.41 |
| MED1007-71 | 75.01 | 4.56 | 10.38 | 2.89 |
| MED1007-72 | 65.93 | 10.25 | 8.78 | 4.14 |
| MED1007-73 | 66.06 | 3.86 | 29.68 | 8.53 |
| MED1007-75 | 51.31 | 6.47 | 11.07 | 4.73 |
| MED1007-83 | 87.58 | 13.37 | 36.18 | 5.41 |
| MED1007-84 | 99.19 | 6.55 | 58.69 | 9.60 |
| MED1007-85 | 90.10 | 8.98 | 66.25 | 2.16 |
| MED1007-86 | 39.60 | 7.57 | 19.17 | 2.97 |
| MED1007-87 | 60.58 | 11.46 | 13.77 | 5.82 |
| MED1007-88 | 109.90 | 3.38 | 46.17 | 2.72 |
| MED1007-91 | 123.67 | 12.67 | 97.03 | 9.40 |
| MED1007-97 | 114.22 | 10.91 | 56.26 | 15.28 |
| MED1007-98 | 117.55 | 9.60 | 102.16 | 25.20 |
| MED1007-99 | 88.30 | 8.37 | 23.31 | 3.06 |
| MED1007-101 | 126.00 | 4.56 | 49.53 | 9.31 |
| MED1007-103 | 82.17 | 11.55 | 55.28 | 5.82 |
| MED1007-104 | 106.40 | 5.35 | 60.32 | 7.07 |
| MED1007-105 | 110.74 | 15.85 | 60.41 | 5.51 |
| MED1007-106 | 97.43 | 9.31 | 24.37 | 5.18 |
| MED1007-107 | 65.78 | 14.86 | 29.88 | 4.55 |
| wortmamnnin | 104.86 | 11.68 | 109.45 | 2.58 |

TABLE 6

Inhibition rate of the compounds of the present invention to PI3 K γ

|  | 10 μM | | 1 μM | |
|---|---|---|---|---|
|  | Inhibition rate % | SD | Inhibition rate % | SD |
| MED1007-15 | 19.09 | 8.95 | 10.38 | 7.55 |
| MED1007-31 | 52.59 | 4.55 | 11.33 | 6.12 |
| MED1007-32 | 4.28 | 3.61 | -13.71 | 7.68 |
| MED1007-33 | 20.00 | 9.75 | 20.99 | 8.94 |
| MED1007-34 | 57.33 | 4.76 | 24.44 | 10.18 |
| MED1007-35 | 53.05 | 3.70 | 19.18 | 0.99 |
| MED1007-51 | 56.18 | 15.01 | 1.16 | 2.65 |

TABLE 6-continued

Inhibition rate of the compounds of the present invention to PI3 K γ

|  | 10 μM | | 1 μM | |
|---|---|---|---|---|
|  | Inhibition rate % | SD | Inhibition rate % | SD |
| MED1007-54 | -4.67 | 4.95 | -6.81 | 3.58 |
| MED1007-58 | -0.98 | 1.10 | -0.29 | 4.12 |
| MED1007-59 | 4.97 | 0.93 | 0.83 | 1.60 |
| MED1007-60 | 4.45 | 4.85 | -2.59 | 3.93 |
| MED1007-61 | 20.40 | 4.76 | -8.18 | 2.00 |
| MED1007-63 | 14.73 | 15.73 | 0.96 | 1.65 |
| MED1007-64 | 15.93 | 4.27 | -4.23 | 4.17 |
| MED1007-65 | 37.22 | 5.52 | 1.54 | 4.44 |
| MED1007-66 | -2.46 | 3.49 | 1.48 | 3.84 |
| MED1007-67 | 10.21 | 7.20 | 0.71 | 6.12 |
| MED1007-68 | 10.85 | 9.88 | -0.02 | 4.68 |
| MED1007-69 | 21.13 | 8.31 | 1.27 | 2.04 |
| MED1007-70 | 10.85 | 3.20 | 5.26 | 2.89 |
| MED1007-71 | 47.43 | 6.15 | 2.55 | 6.12 |
| MED1007-72 | 42.71 | 7.31 | 2.15 | 4.11 |
| MED1007-73 | 28.41 | 7.23 | 5.49 | 3.04 |
| MED1007-75 | 10.92 | 4.32 | 6.93 | 5.85 |
| MED1007-83 | 23.98 | 3.52 | 5.93 | 3.06 |
| MED1007-84 | 34.17 | 1.76 | 26.57 | 2.85 |
| MED1007-85 | 41.94 | 3.67 | 16.79 | 1.75 |
| MED1007-86 | 23.06 | 4.68 | 8.35 | 3.48 |
| MED1007-87 | 29.49 | 1.24 | -3.76 | 5.33 |
| MED1007-88 | 41.52 | 2.75 | 7.02 | 2.82 |
| MED1007-91 | 81.29 | 1.76 | 29.82 | 5.14 |
| MED1007-97 | 77.03 | 8.34 | 74.69 | 11.34 |
| MED1007-98 | 105.26 | 8.04 | 32.83 | 9.84 |
| MED1007-99 | 39.93 | 7.59 | 4.68 | 1.71 |
| wortmamnnin | 100.51 | 10.99 | 104.58 | 11.89 |
| XC-302 | 49.31 | 11.50 | 18.27 | 11.54 |

TABLE 7

Inhibition rate of the compounds of present invention to PI3Kδ

|  | 10 μM | | 1 μM | |
|---|---|---|---|---|
|  | Inhibition rate % | SD | Inhibition rate % | SD |
| MED1007-15 | 8.64 | 8.12 | 1.25 | 6.17 |
| MED1007-31 | 97.80 | 4.37 | 40.16 | 4.04 |
| MED1007-32 | 42.08 | 10.18 | 30.97 | 6.64 |
| MED1007-33 | 62.98 | 4.66 | 21.44 | 5.31 |
| MED1007-34 | 69.84 | 11.17 | 40.16 | 6.69 |
| MED1007-35 | 87.40 | 12.33 | 44.42 | 4.09 |
| MED1007-51 | 75.53 | 12.27 | 39.62 | 3.85 |
| MED1007-54 | 42.35 | 5.37 | 13.29 | 11.60 |
| MED1007-58 | 35.00 | 7.28 | 2.11 | 1.15 |
| MED1007-59 | 59.00 | 11.29 | 17.98 | 3.23 |
| MED1007-60 | 34.08 | 9.10 | -2.33 | 2.61 |
| MED1007-61 | 102.25 | 8.51 | 16.67 | 5.77 |
| MED1007-63 | 122.21 | 0.16 | 37.50 | 5.09 |
| MED1007-64 | 88.73 | 6.17 | 14.14 | 1.23 |
| MED1007-65 | 38.36 | 2.96 | 7.48 | 2.68 |
| MED1007-66 | 19.84 | 6.82 | 4.75 | 2.46 |
| MED1007-67 | 32.02 | 4.75 | 11.27 | 7.44 |
| MED1007-68 | 42.27 | 5.89 | 20.71 | 3.54 |
| MED1007-69 | 36.42 | 2.73 | 28.94 | 3.84 |
| MED1007-70 | 51.56 | 11.53 | 41.00 | 8.43 |
| MED1007-71 | 64.36 | 10.65 | 24.37 | 6.54 |
| MED1007-72 | 89.46 | 6.27 | 33.92 | 2.32 |
| MED1007-73 | 66.45 | 4.33 | 6.41 | 8.13 |
| MED1007-75 | 42.60 | 7.49 | 10.92 | 6.19 |
| MED1007-83 | 68.47 | 5.63 | 22.69 | 3.39 |
| MED1007-84 | 101.02 | 9.19 | 71.75 | 0.89 |
| MED1007-85 | 113.38 | 11.47 | 54.15 | 11.86 |
| MED1007-86 | 66.43 | 3.10 | 27.31 | 4.01 |
| MED1007-87 | 79.97 | 4.73 | 23.00 | 1.11 |
| MED1007-88 | 102.74 | 4.98 | 30.99 | 3.17 |
| MED1007-91 | 115.45 | 6.14 | 96.32 | 9.56 |
| MED1007-97 | 88.46 | 1.49 | 72.30 | 6.62 |
| MED1007-98 | 105.16 | 6.79 | 71.13 | 11.27 |

TABLE 7-continued

Inhibition rate of the compounds of present invention to PI3Kδ

|  | 10 μM | | 1 μM | |
|---|---|---|---|---|
|  | Inhibition rate % | SD | Inhibition rate % | SD |
| MED1007-99 | 88.11 | 2.47 | 7.67 | 0.95 |
| MED1007-101 | 95.57 | 6.39 | 75.71 | 9.72 |
| MED1007-103 | 87.50 | 4.65 | 68.04 | 6.21 |
| MED1007-104 | 85.86 | 7.71 | 57.14 | 1.69 |
| MED1007-105 | 104.61 | 4.14 | 74.20 | 7.59 |
| MED1007-106 | 89.10 | 3.54 | 32.93 | 11.47 |
| MED1007-107 | 119.10 | 0.19 | 29.34 | 1.62 |
| wortmamnnin | 107.83 | 4.35 | 95.38 | 9.07 |
| xc-302 | 67.42 | 5.07 | 22.84 | 10.45 |

TABLE 8

Inhibition rate of the test compounds to PI3K delta

| PI3K delta | 10 μM | | 2 μM | | 0.4 μM | |
|---|---|---|---|---|---|---|
|  | Inhibition rate % | SD | Inhibition rate % | SD | Inhibition rate % | SD |
| MED1007-108 | 89.03 | 6.37 | 78.59 | 0.33 | 40.49 | 6.40 |
| MED1007-109 | 91.58 | 2.02 | 44.05 | 8.43 | 22.64 | 4.21 |
| MED1007-109S | 94.36 | 7.36 | 57.34 | 4.49 | 30.22 | 3.83 |
| MED1007-110 | 12.60 | 8.28 | 2.94 | 1.14 | 6.26 | 1.75 |
| MED1007-113 | 68.86 | 1.23 | 37.71 | 1.94 | 29.98 | 2.20 |
| MED1007-114 | 78.94 | 1.15 | 49.15 | 7.43 | 28.36 | 6.12 |
| MED1007-115 | 94.59 | 0.33 | 60.20 | 6.38 | 36.79 | 5.34 |
| MED1007-132 | 54.97 | 5.37 | 8.54 | 4.96 | −0.76 | 1.74 |
| MED1007-133 | 83.41 | 9.01 | 69.00 | 1.91 | 20.77 | 2.59 |
| MED1007-135 | 83.41 | 4.19 | 59.60 | 2.40 | 27.17 | 6.82 |
| MED1007-136 | 80.51 | 5.37 | 44.84 | 6.69 | 15.66 | 3.82 |
| MED1007-137 | 99.14 | 5.60 | 63.30 | 0.14 | 27.62 | 3.09 |
| MED1007-139 | 20.12 | 2.74 | 15.01 | 5.98 | 4.29 | 3.87 |
| Wortmannin | 104.91 | 0.82 | 109.43 | 5.90 | 93.43 | 7.66 |

It can be seen from Table 5, 6, 7, 8 that 1007 series of compounds of the present invention are effective PI3K inhibitor, and the selectivities of different compounds to PI3K subtype are different. It can be seen from the results that the compound of the present invention can select specific PI3K inhibitors and extensive PI3K inhibitors, with good antitumor activity and selectivity.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A compound of Formula (I) or a pharmaceutically acceptable salt or a hydrate thereof, wherein the compound of Formula (I) is:

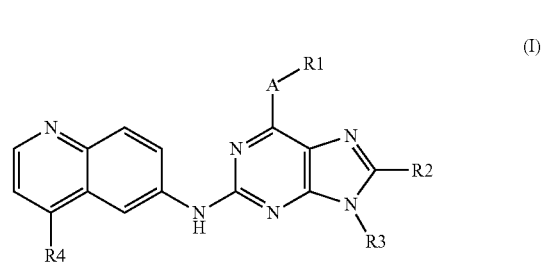

wherein, R1 represents unsubstituted C1~C6 straight or branched alkyl; or C1~C6 straight or branched alkyl substituted by methoxyl, C3~C6-cycloalkyl, hydroxyl or amino; or unsubstituted C3~C6-cycloalkyl; or C3~C6-cycloalkyl substituted by carboxylic carbomethoxy or carboxylic; or phenyl substituted by methoxy; unsubstituted morpholinyl; unsubstituted piperazinyl; unsubstituted piperidyl; piperidyl substituted by hydroxyl or acylamino; unsubstituted pyrrolidinyl;

R2 is H;

R3 represents H, tetrahydropyrane, trifluoroethyl, piperidyl;

R4 represents H, unsubstituted C1~C6 straight alkyl; unsubstituted C3~C6 cycloalkyl; unsubstituted phenyl, phenyl substituted by carboxylic carbomethoxy, C1~C6 straight alkoxy, bis-C1~C6 straight alkoxy, C1~C6 straight alkyl sulphanyl or halogen atoms; 1,3-benzodioxol; unsubstituted morpholinyl; unsubstituted piperazinyl; piperazinyl substituted by methyl; cyclopentylmethyl;

A represents N or O; when A is N, R4 is not equal to H.

2. The compound of Formula (I) or a pharmaceutically acceptable salt or a hydrate thereof according to claim 1, wherein R4 represents methyl, ethyl, cyclopropyl, phenyl, p-methylbenzoatyl, m-methylbenzoatyl, o-methoxyphenyl, m-methoxyphenyl, p-methoxyphenyl, m-ethoxyphenyl, dimethoxyphenyl, o-methylthiophenyl, m-methylthiophenyl, m-fluorophenyl, p-fluorophenyl, 1,3-benzodioxol, morpholinyl, piperazinyl and methylpiperazinyl.

3. The compound of Formula (I) or a pharmaceutically acceptable salt or a hydrate thereof according to claim 1, wherein the compounds of formula (I) are selected from the following compounds:

1) N6-cyclopropyl-N2-(4-morpholinyl quinoline-6-yl)-9H-purine-2,6-diamine;
2) N6-cyclopropyl-N2-(4-(piperazin-1-yl) quinoline-6-yl)-9H-purine-2, 6-diamine;
3) N-(6-isopropoxy-9H-purine-2-yl) quinoline-6-amine;
4) N-(6-Cyclopentyloxy-9H-purine-2-yl) quinoline-6-amine;
5) N-(6-isopropoxy-9H-purine-2-yl)-4-(phenyl-1-yl) quinoline-6-amine;
6) N-(6-isopropoxy-9H-purine-2-yl)-4-(phenyl-1-yl) quinoline-6-amine-methanesulfonate;
7) N6-cyclopropyl-N2-(4-methylquinoline-6-yl)-9H-purine-2, 6-diamine dihydrate dimethanesulfonate;
8) N6-cyclopropyl-N2-(4-ethylquinoline-6-yl)-9H-purine-2, 6-diamine dihydrate dimethanesulfonate;
9) N6-cyclopropyl-N2-(4-cyclopropyl quinoline-6-yl)-9H-purine-2, 6-diamine dihydrate dimethanesulfonate;
10) 2-(4-(4-methoxyphenyl) quinoline-6-yl amino)-9H-purine-6-ol-methanesulfonate;
11) 4-[1, 3] benzodioxol-5-yl)-N-(6-isopropoxy-9H-purine-2-yl) quinoline-6-amine-methanesulfonate;

12) 2-(4-(3-methoxy phenyl) quinoline-6-yl amino) 9H-purine-6-ol-methanesulfonate;
13) 4-(3-fluorophenyl)-N-(6-isopropoxy-9H-purine-2-yl) quinoline-6-amine-methanesulfonate;
14) 4-(4-fluorophenyl)-N-(6-isopropoxy-9H-purine-2-yl) quinoline-6-amine-methanesulfonate;
15) 4-(3, 4-dimethoxy phenyl)-N-(6-isopropoxy-9H-purine-2-yl) quinoline-6-amine-methanesulfonate;
16) 2-(4-([1, 3] benzodioxol-5-yl) quinoline-6-yl amino)-9H-purine-6-ol-methanesulfonate;
17) N-(6-isopropoxy-9H-purine-2-yl)-4-(piperazine-1-yl) quinoline-6-amine-methanesulfonate;
18) N-(6-isopropoxy-9H-purine-2-yl)-4-(4-methyl piperazine-1-yl) quinoline-6-amine-methanesulfonate;
19) 1-(2-(4-phenyl quinoline-6-yl amino)-9H-purine-6-yl) piperidine-4-ol;
20) 1-(2-(4-phenyl quinoline-6-yl amino)-9H-purine-6-yl) piperidine-3-amide;
21) 1-(2-(4-phenyl quinoline-6-yl amino)-9H-purine-6-yl amino) cyclopropane carboxylic acid methyl ester;
22) 1-(2-(4-phenyl quinoline-6-yl amino)-9H-purine-6-yl amino) cyclopropane carboxylic acid;
23) N6-cyclopropyl-N2-(4-phenyl quinoline-6-yl)-9H-purine-2,6 diamine;
24) N-(6-phenoxy-9H-purine-2-yl)-4-(piperazine-1-yl) quinoline-6-amine;
25) N-(6-isopropoxy-9H-purine-2-yl)-4-(piperazine-1-yl) quinoline-6-amine;
26) 4-(6-(6-(cyclopropyl amino)-9H-purine-2-yl amino) quinoline-4-yl) p-methyl benzoate;
27) 4-(6-(6-(cyclopropyl amino)-9H-purine-2-yl amino) quinoline-4-yl) m-methyl benzoate;
28) N6-cyclopropyl-N2-(4-(3-methoxy phenyl) quinoline-6-yl)-9H-purine-2,6-diamine;
29) N6-cyclopropyl-N2-(4-(4-methoxy phenyl) quinoline-6-yl)-9H-purine-2,6-diamine;
30) N6-cyclopropyl-N2-(4-(3-fluorophenyl) quinoline-6-yl)-9H-purine-2,6-diamine;
31) N6-cyclopropyl-N2-(4-phenyl quinoline-6-yl)-9-(2, 2, 2-trifluoroethyl)-9H-purine-2, 6-diamine;
32) N6-cyclopropyl-N2-(4-phenyl quinoline-6-yl)-9-(piperidine-4-yl)-9H-purine-2,6-diamine;
33) N6-(3-methoxy propyl)-N2-(4-phenyl quinoline-6-yl)-9H-purine-2, 6-diamine;
34) N6-(2-methoxy ethyl)-N2-(4-phenyl quinoline-6-yl)-9H-purine-2, 6-diamine;
35) 2-(2-(4-phenyl quinoline-6-yl amino)-9H-purine-6-yl amino) ethanol;
36) N6-(2-aminoethyl)-N2-(4-phenyl quinoline-6-yl)-9H-purine-2, 6-diamine;
37) N6-cyclobutyl-N2-(4-(3-methoxy phenyl) quinoline-6-yl)-9H-purine-2,6-diamine;
38) N6-cyclobutyl-N2-(4-(4-fluorophenyl) quinoline-6-yl)-9H-purine-2,6-diamine;
39) 3-(2-(4-phenyl quinoline-6-yl amino)-9H-purine-6-yl amino) propyl-1-ol;
40) N6-cyclobutyl-N2-(4-phenyl quinoline-6-yl)-9H-purine-2, 6-diamine;
41) N6-cyclopropyl-N2-(4-(3-ethoxy phenyl) quinoline-6-yl)-9H-purine-2,6-diamine;
42) N6-cyclopropyl-N2-(4-(3, 4-dimethoxy phenyl) quinoline-6-yl)-9H-purine-2, 6-diamine;
43) N2-(4-(benzo [1, 3] dioxole-5-yl) quinoline-6-yl)-N6-cyclopropane-9H-purine-2, 6-diamine;
44) N6-cyclopropyl-N2-(4-(2-methoxy phenyl) quinoline-6-yl)-9H-purine-2, 6-diamine;
45) N6-cyclopropyl-N2-(4-(2-(methylthio) phenyl) quinoline-6-yl)-9H-purine-2, 6-diamine;
46) N6-cyclopropyl-N2-(4-(3-(methylthio) phenyl) quinoline-6-yl)-9H-purine-2,6-diamine;
47) N6-cyclopropyl-N2-(4-phenyl quinoline-6-yl)-9H-purine-2, 6-diammonium salt dihydrate dimethanesulfonate;
48) N-(6-cyclobutyl-9H-purine-2-yl) quinoline-6-amine;
49) N-(6-cyclobutyl-9H-purine-2-yl)-4-phenyl quinoline-6-amine;
50) N6-(cyclopentyl methyl)-N2-(4-phenyl quinoline-6-yl)-9H-purine-2, 6-diamine;
51) N6-isopropyl-N2-(4-phenyl quinoline-6-yl)-9H-purine-2, 6-diamine;
52) 4-phenyl-N-(6-(pyrrolidine-1-yl)-9H-purine-2-yl) quinoline-6-amine;
53) N-(6-isopropoxy-9H-purine-2-yl) quinoline-6-amine;
54) N-(6-(pentyl-3-yl oxyl)-9H-purine-2-yl)-4-phenyl quinoline-6-amine;
55) N6-cyclopentyl-N2-(4-phenyl quinoline-6-yl)-9H-purine-2, 6-diamine;
56) N-(6-cyclohexyloxy-9H-purine-2-yl)-4-phenyl quinoline-6-amine;
57) N-(6-isopropoxy-9H-purine-2-yl)-4-phenyl quinoline-6-amine dihydrate dimethane-sulfonate;
58) N-(6-morpholine-9H-purine-2-yl)-4-phenyl quinoline-6-amine;
59) N-(6-morpholine-9H-purine-2-yl)-4-phenyl quinoline-6-amine dihydrate dimethanesulfonate; and
60) 2-(4-phenyl quinoline-6-yl amino)-9H-purine-6-ol.

4. A pharmaceutical composition, wherein the pharmaceutical composition consists of the compounds or pharmaceutically acceptable salts or hydrates thereof according to claim 1 and a pharmaceutical acceptable excipient.

5. The pharmaceutical composition according to claim 4, wherein the salt is an acidic addition salt produced by an organic acid or inorganic acid, or the salt is an alkaline addition salt produced by an organic alkali or inorganic alkali; wherein the acid is selected from hydrochloric acid, sulfuric acid, hydrobromic acid, methanesulfonic acid, benzenesulfonic acid, p-toluenesulfonic acid, maleic acid, fumaric acid, lactic acid, and citric acid.

6. The pharmaceutical composition according to claim 4, wherein the pharmaceutical composition is in the form of a tablet, a capsule, a pill, an oral liquid preparation, a granule, a powder, an injection, an implant or an external preparation.

7. A pharmaceutical composition, wherein the pharmaceutical composition consists of the compounds or pharmaceutically acceptable salts or hydrates thereof according to claim 2 and a pharmaceutically acceptable excipient.

8. A pharmaceutical composition, wherein the pharmaceutical composition consists of the compounds or pharmaceutically acceptable salts or hydrates thereof according to claim 3 and a pharmaceutically acceptable excipient.

9. A preparation method of a compound or a pharmaceutically acceptable salt or a hydrate thereof according to claim 1, wherein the method includes the following steps:
1) reacting compound (a) with R3 under catalysis of catalyst p-toluene sulfonic acid or pyridine salt of p-toluene sulfonic acid, and then condensating with HA-R1 to obtain compound (b) at temperature of 20~100□ in the presence of depickling solvent such as triethylamine, sodium carbonate, potassium carbonate or sodium bicarbonate;

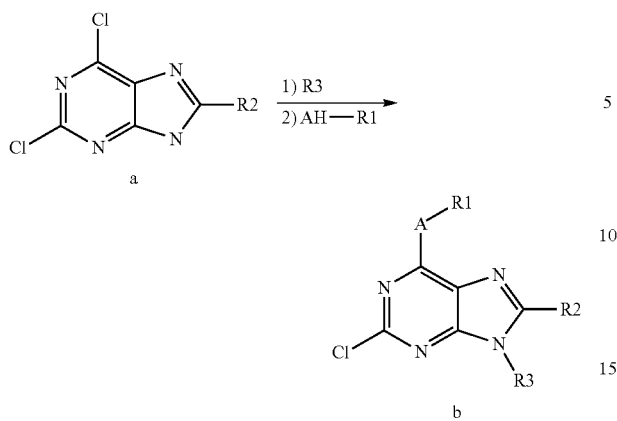

2) undergoing catalytic coupling reaction of compounds (b) and (c) with catalyst, ligand, alkali, aprotic solvent at temperature of 15~150□ and then forming salts with acids to obtain compound (d),

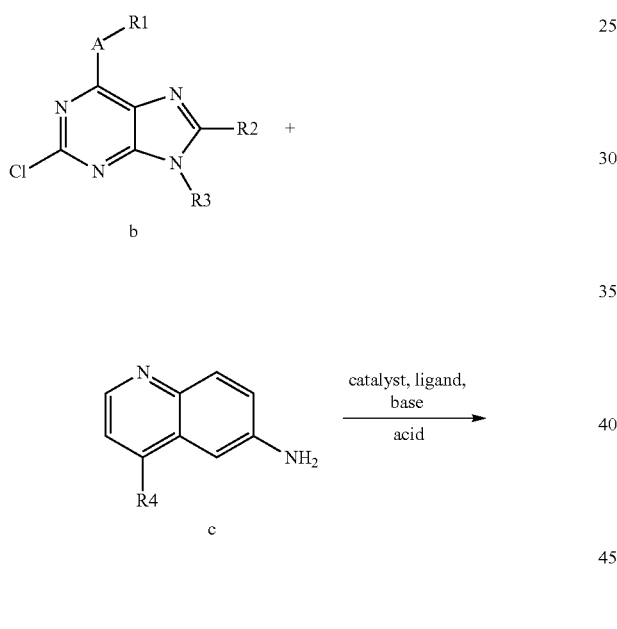

wherein, in the catalytic coupling reaction, the ligand is selected from any one of tri-o-tolylphosphine (P(o-tolyl)3), tri-tert-butylphosphine (P(Bu-t)3), 2,2'-diphenylphosphine-1,1'-binaphthalene (BINAP), 1,1'-diphenylphosphine-ferrocene (DPPF), bis(2-diphenylphosphinophenyl) ether (DPEphos), 9,9-dimethyl-4,5-diphenylphosphine xanthone (Xantphos), compounds of ligand formula (1), (2), (3), (4), (5), (6), (7), (8), (9), (10) or (11),

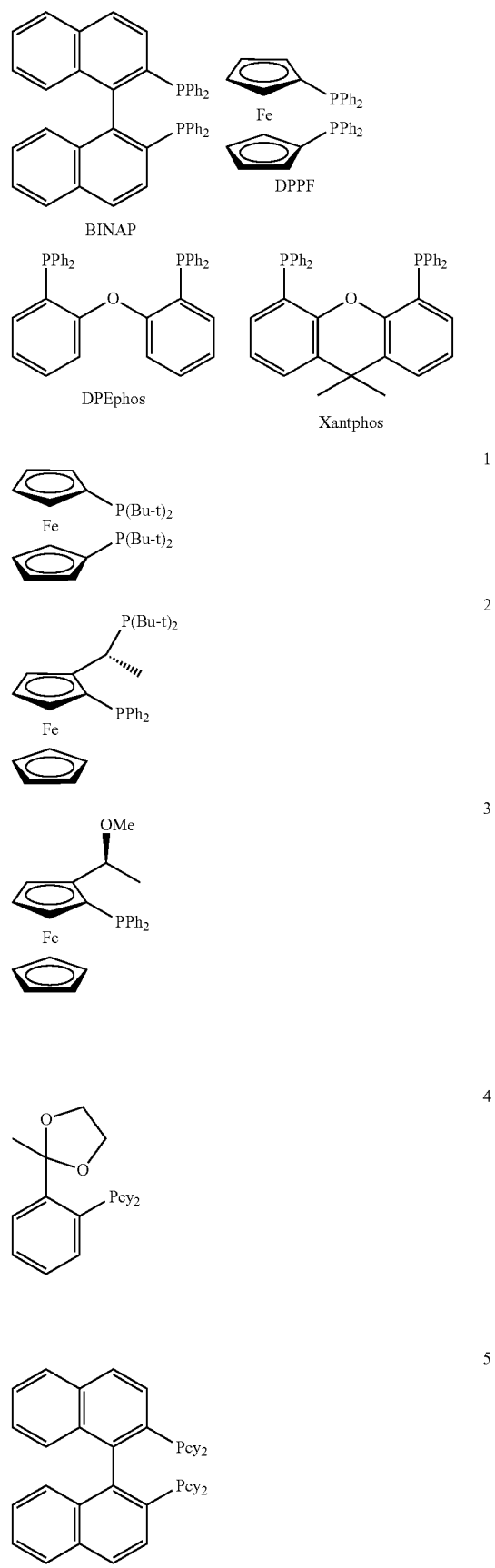

-continued

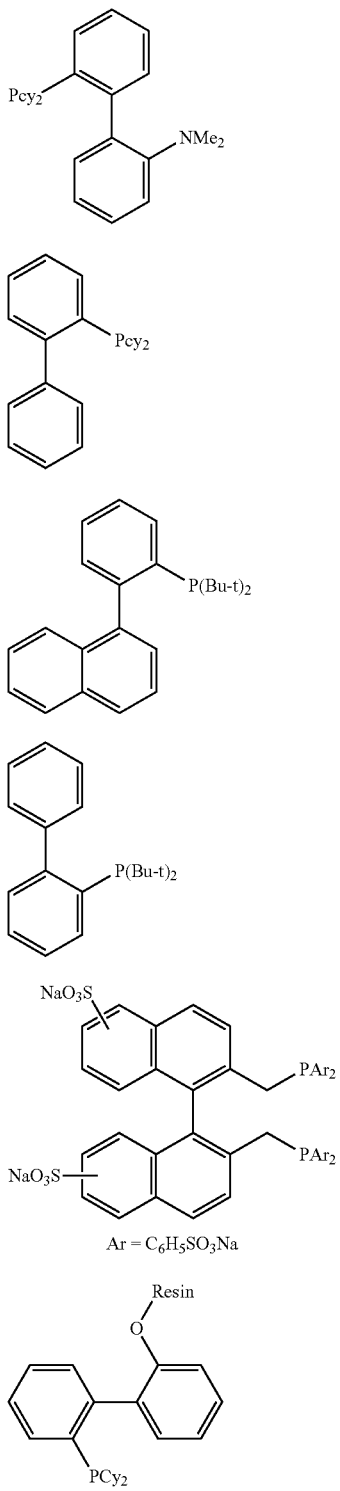

the catalyst is transition metal catalysts palladium or nickel such as PdCl$_2$, Pd(OAc)$_2$, Pd$_2$(dba)$_3$, Ni (OAc)$_2$ or Ni/C;
the alkali is sodium tert-butoxide, potassium tert-butoxide, potassium carbonate, cesium carbonate and tripotassium phosphate;
the acid in salt-forming with acids is selected from any one or its combination of hydrochloric acid, sulphuric acid, hydrobromic acid, methanesulfonic acid, benzenesulfonic acid, paratoluenesulfonic acid, maleic acid, fumaric acid, lactic acid, citric acid;

3) neutralizing compound (d) with sodium carbonate, potassium carbonate, sodium hydroxide or potassium hydroxide to produce the compound (I);

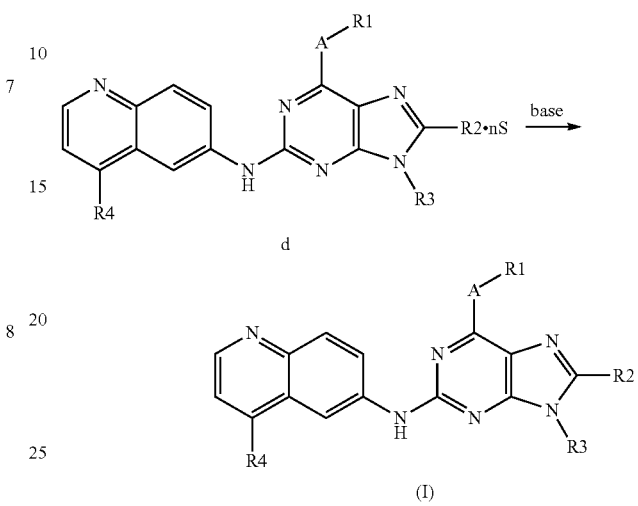

wherein, R1 represents unsubstituted C1~C6 straight or branched alkyl; or C1~C6 straight or branched alkyl substituted by methoxyl, C3~C6-cycloalkyl, hydroxyl or amino; or unsubstituted C3~C6-cycloalkyl; or C3~C6-cycloalkyl substituted by carboxylic carbomethoxy or carboxylic; or phenyl substituted by methoxy; unsubstituted morpholinyl; unsubstituted piperazinyl; unsubstituted piperidyl; piperidyl substituted by hydroxyl or acylamino; unsubstituted pyrrolidinyl;
R2 is H;
R3 is H, 2,3-dihydropyrane, trifluoroethyl or piperidyl;
R4 represents H, unsubstituted C1~C6 straight alkyl; unsubstituted C3~C6 cycloalkyl; unsubstituted phenyl, phenyl substituted by carboxylic carbomethoxy, C1~C6 straight alkoxy, bis-C1~C6 straight alkoxy, C1~C6 straight alkyl sulphanyl or halogen atoms; 1,3-benzodioxol; unsubstituted morpholinyl; unsubstituted piperazinyl; or piperazinyl substituted by methyl;
A represents N or O; when A represents N, R4 is not equal to H.

10. The preparation method of a compound or a pharmaceutical acceptable salt or a hydrate thereof according to claim 9, wherein the reacting molar ratio of compound (a) to R3 is 1:1~5, the molar ratio of the compound (a) to compound HA-R1 is 1:1~5, the temperature of condensation reaction is 40~60☐.

11. The preparation method of a compound or a pharmaceutically acceptable salt or a hydrate thereof according to claim 9, is characterized in that, the molar ratio of compound (b) to compound (c) is 1:0.5~2; the temperature of catalytic coupling reaction is 55~120☐ or using microwave heating; the aprotic solvent is selected from any one or its combination of tetrahydrofuran, isopropyl ether, glycol dimethyl ether, dioxane, pyridine, 1-methyl-2-pyrrolidone (NMP), 1,3-dimethyltrimethylene urea (DMPU), toluene or xylene.

12. The preparation method of a compound or a pharmaceutically acceptable salt or a hydrate thereof according to claim 9, wherein the molar ratio of compound (b) to acid is 1:1~10, wherein the acid is hydrochloric acid, sulfuric acid, hydrobromic acid, methanesulfonic acid, benzenesulfonic acid, paratoluenesulfonic acid, maleic acid, fumaric acid, lactic acid, citric acid.

* * * * *